United States Patent
Gruenbacher et al.

(10) Patent No.: US 7,021,848 B1
(45) Date of Patent: Apr. 4, 2006

(54) SEMI-ENCLOSED APPLICATOR HAVING A TEMPERATURE CHANGING ELEMENT

(75) Inventors: Dana Paul Gruenbacher, Fairfield, OH (US); James Herbert Davis, Middletown, OH (US); Kevin Joe Fields, Cincinnati, OH (US); Thomas James Manske, Jr., Mason, OH (US); Piyush Narendra Zaveri, Mason, OH (US); Gary Curtis Joseph, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/089,351

(22) PCT Filed: Oct. 10, 2000

(86) PCT No.: PCT/US00/27967

§ 371 (c)(1),
(2), (4) Date: Mar. 27, 2002

(87) PCT Pub. No.: WO01/26499

PCT Pub. Date: Apr. 19, 2001

Related U.S. Application Data

(63) Continuation-in-part of application No. 09/415,866, filed on Oct. 8, 1999, now abandoned, and a continuation-in-part of application No. 09/451,536, filed on Dec. 1, 1999, now Pat. No. 6,508,602.

(60) Provisional application No. 60/209,062, filed on Jun. 2, 2000, provisional application No. 60/217,172, filed on Jul. 10, 2000.

(51) Int. Cl.
*A47L 13/19* (2006.01)
*A61M 35/00* (2006.01)

(52) U.S. Cl. .............. 401/1; 62/4; 126/263.08; 126/263.09; 401/7; 401/132; 604/291; 604/306

(58) Field of Classification Search .............. 401/201; 62/4; 126/263.01, 263.08, 263.09; 604/291
See application file for complete search history.

(56) References Cited

U.S. PATENT DOCUMENTS

| | | | |
|---|---|---|---|
| 2,209,914 A | 7/1940 | Gerber et al. | |
| 2,707,581 A | 5/1955 | Kaplan et al. | |
| 2,790,982 A | 5/1957 | Schneider | |
| 2,945,250 A | 7/1960 | Worthington | |
| 2,961,677 A | 11/1960 | Zecchini et al. | |
| 3,053,385 A | 9/1962 | Spees | |
| 3,060,486 A | 10/1962 | Lewis | |
| 3,116,732 A * | 1/1964 | Cahill | 604/292 |
| 3,298,368 A * | 1/1967 | Charos | 604/292 X |
| 3,324,500 A | 6/1967 | Fuller et al. | |

(Continued)

FOREIGN PATENT DOCUMENTS

DE 3535926 A1 7/1987

(Continued)

*Primary Examiner*—Justine R. Yu
*Assistant Examiner*—Kathleen J. Prunner
(74) *Attorney, Agent, or Firm*—Bridget Murray; Peter D. Meyer

(57) ABSTRACT

A semi-enclosed applicator (10) for distributing a substance onto a target surface is disclosed having a first side (24) having a first internal surface (32) and a first external surface (31); a second side (26) having a second internal surface (34) and a second external surface (33); an internal cavity (29) between the first and second internal surfaces that is externally accessible, and a temperature changing element. The flexible film pouch (30) contains a product located proximately to the first side (24).

19 Claims, 24 Drawing Sheets

U.S. PATENT DOCUMENTS

| | | | |
|---|---|---|---|
| 3,485,562 A | 12/1969 | Hidden et al. | |
| 3,608,708 A | 9/1971 | Storandt | |
| 3,636,922 A | 1/1972 | Ketner | |
| 3,638,786 A | 2/1972 | Borecki et al. | |
| 3,757,782 A | 9/1973 | Aiken | |
| 3,768,916 A | 10/1973 | Avery | |
| 4,087,675 A * | 5/1978 | Sansonetti | 604/292 |
| 4,148,318 A | 4/1979 | Meyer | |
| 4,430,013 A | 2/1984 | Kaufman | |
| 4,510,640 A | 4/1985 | Omori | |
| 4,537,819 A | 8/1985 | Schortmann et al. | |
| 4,563,103 A | 1/1986 | Van Overloop et al. | |
| 4,596,481 A | 6/1986 | Tanaka | |
| 4,600,620 A | 7/1986 | Lloyd et al. | |
| 4,696,593 A | 9/1987 | Bayless | |
| 4,759,472 A | 7/1988 | Strenger | |
| 4,762,124 A | 8/1988 | Kerch et al. | |
| 4,893,955 A | 1/1990 | Zielinski | |
| 4,902,283 A | 2/1990 | Rojko et al. | |
| 4,958,881 A | 9/1990 | Piros | |
| 5,008,969 A | 4/1991 | Jarrett | |
| 5,090,832 A | 2/1992 | Rivera et al. | |
| 5,100,028 A | 3/1992 | Seifert | |
| 5,127,127 A | 7/1992 | Jarosinski | |
| 5,195,658 A | 3/1993 | Hoshino | |
| 5,380,110 A | 1/1995 | Festa | |
| 5,411,178 A | 5/1995 | Roders et al. | |
| 5,441,355 A | 8/1995 | Moore | |
| 5,454,207 A | 10/1995 | Storandt | |
| 5,490,736 A | 2/1996 | Habert et al. | |
| 5,558,874 A | 9/1996 | Haber et al. | |
| 5,616,201 A | 4/1997 | Finch et al. | |
| 5,636,406 A | 6/1997 | Strong | |
| 5,681,574 A | 10/1997 | Haber et al. | |
| 5,829,089 A | 11/1998 | Steadman | |
| 5,957,605 A | 9/1999 | Cohen et al. | |
| 6,141,801 A * | 11/2000 | Helenick | 2/159 |
| 6,305,044 B1 | 10/2001 | James et al. | |

FOREIGN PATENT DOCUMENTS

| | | | |
|---|---|---|---|
| EP | | 0 294 189 | 12/1988 |

* cited by examiner

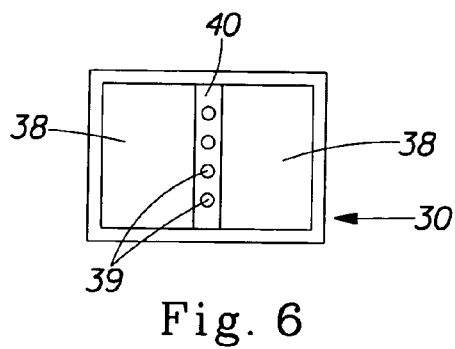
Fig. 6
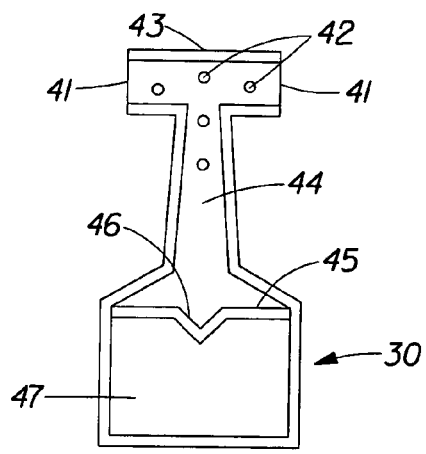
Fig. 7
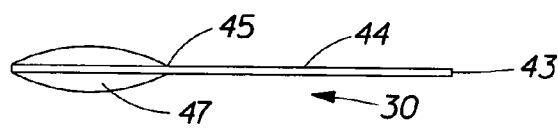
Fig. 8
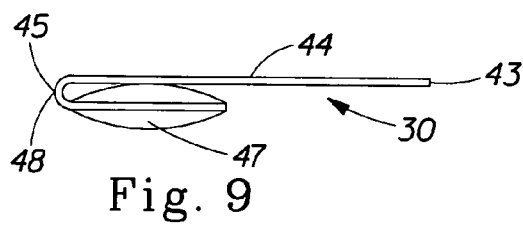
Fig. 9
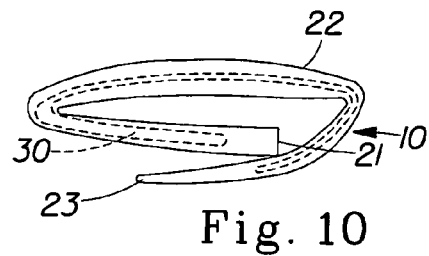
Fig. 10
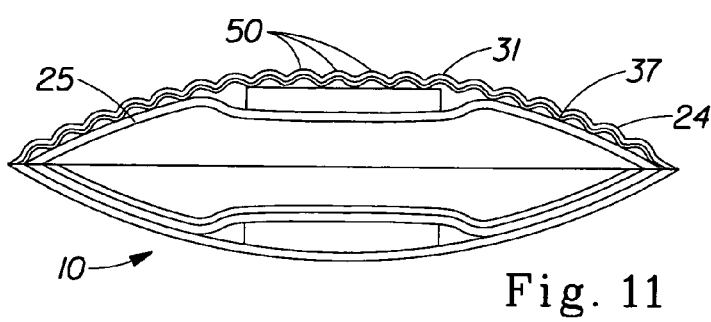
Fig. 11
Fig. 12
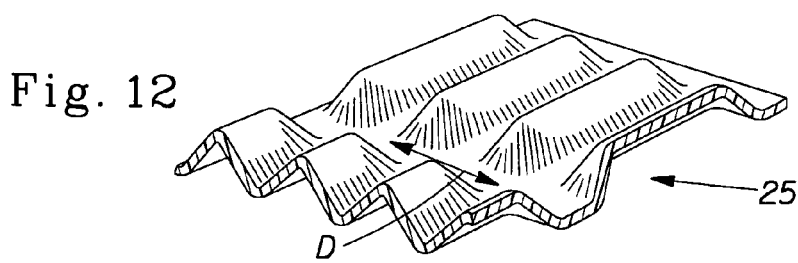

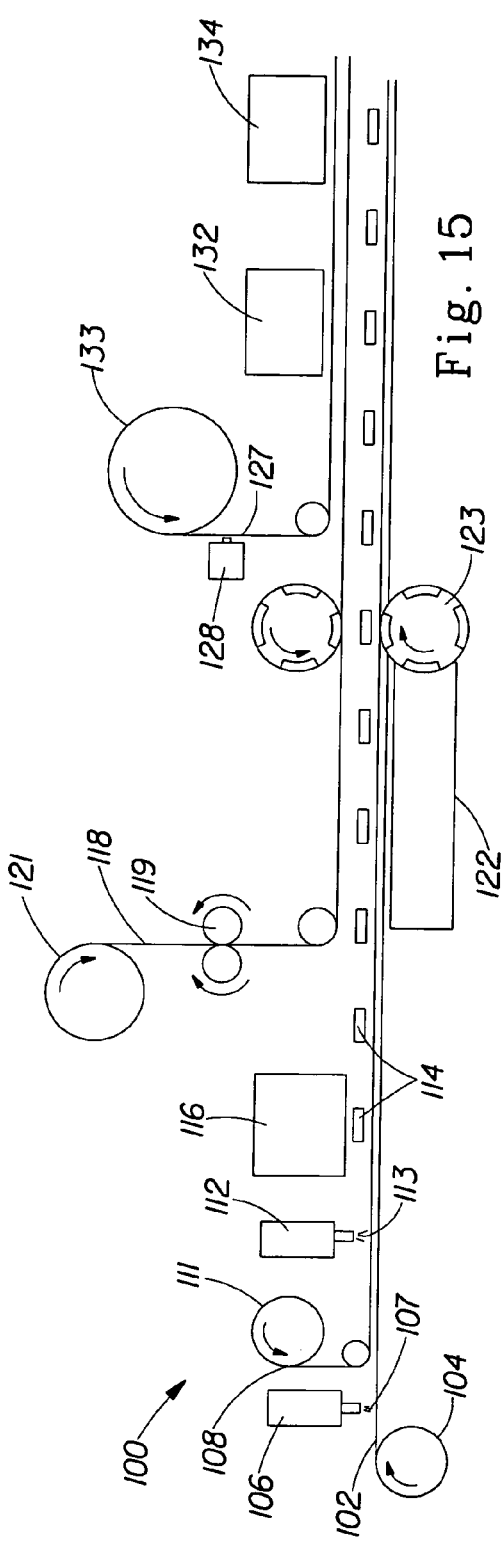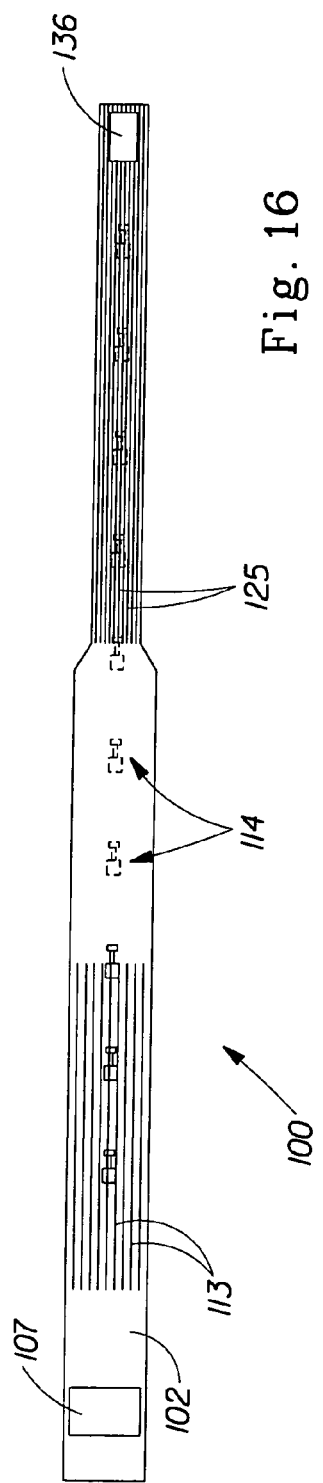

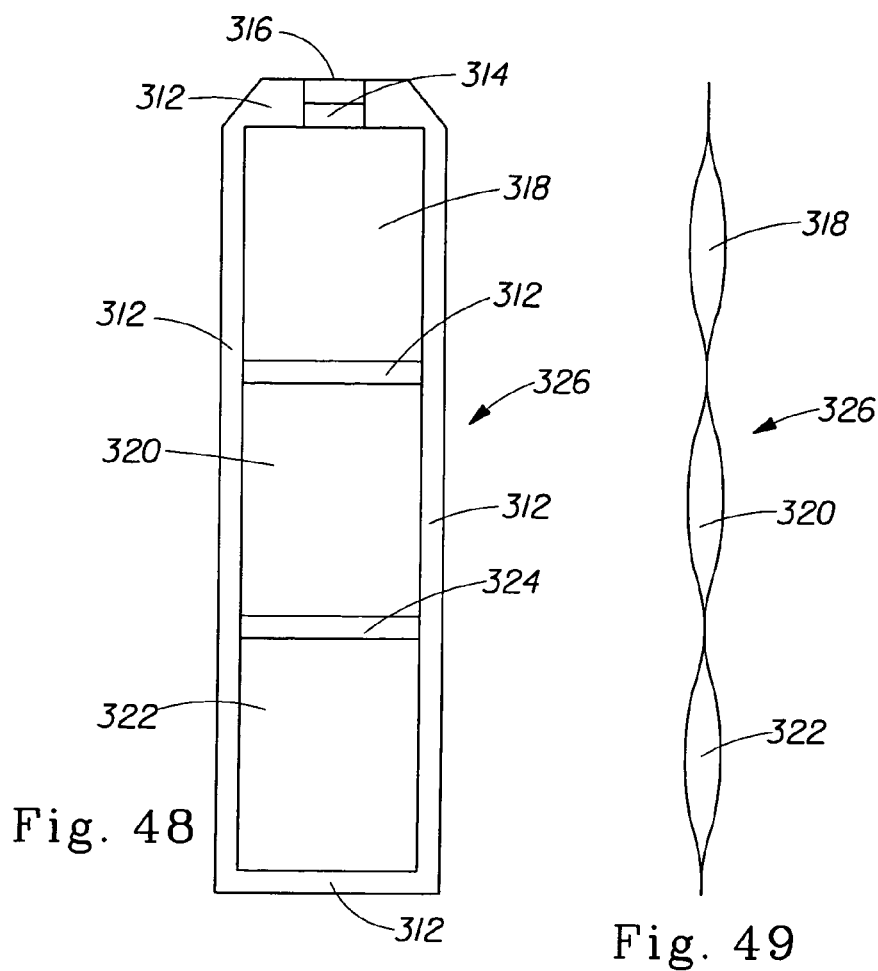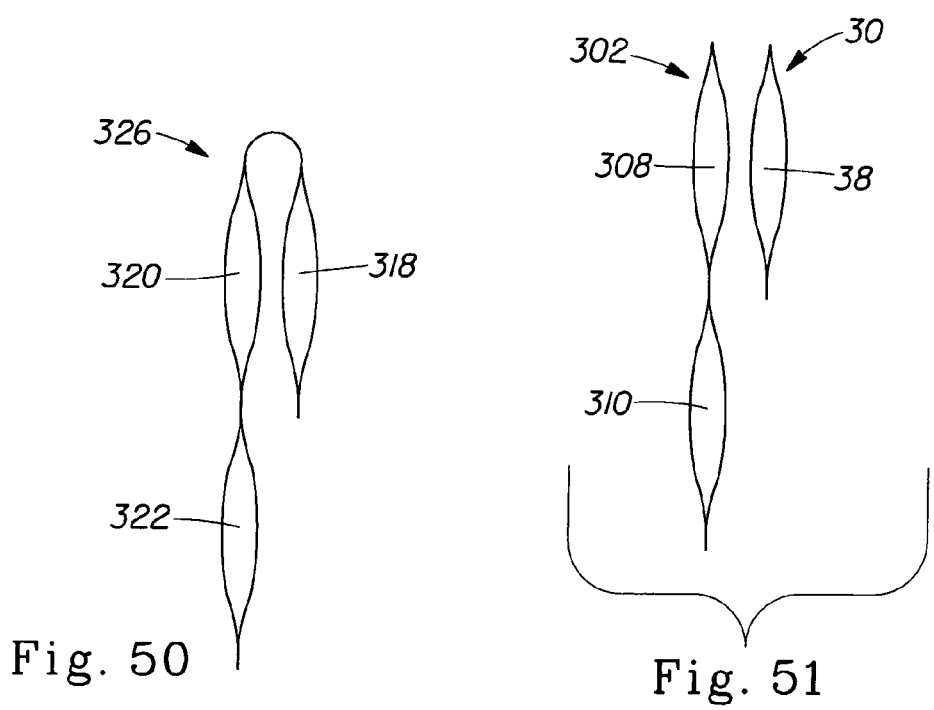
Fig. 48　Fig. 49　Fig. 50　Fig. 51

US 7,021,848 B1

SEMI-ENCLOSED APPLICATOR HAVING A TEMPERATURE CHANGING ELEMENT

CROSS-REFERENCE TO PRIOR APPLICATIONS

This application is PCT Application No. PCT/US00/27967 filed on Oct. 10, 2000 and published in English, which is a Continuation-In-Part of U.S. application Ser. No. 09/415,866, filed on Oct. 8, 1999, now abandoned, and is a Continuation-In-Part of U.S. application Ser. No. 09/451,536, filed Dec. 1, 1999, now U.S. Pat. No. 6,508,602, and claims the benefit of U.S. Provisional Application No. 60/209,062, filed on Jun. 2, 2000, and claims the benefit of U.S. Provisional Application No. 60/217,172, filed on Jul. 10, 2000.

FIELD OF THE INVENTION

The present invention relates to a semi-enclosed applicator useful for distributing substances onto target surfaces. More particularly, the present invention also relates to such an applicator that also contains a substance for application to the surface of a target object.

BACKGROUND OF THE INVENTION

In the art of dispensing, articles have been developed which are coated or impregnated with useful substances intended to be utilized when the article is contacted with a target surface. While there are advantages with having the substance present on or near the surface of such articles, there is often the drawback that the useful substance is unprotected and is subject to inadvertent contact before intended use. Inadvertent contact may lead to contamination of the substance, loss of the substance onto surfaces other than the desired target surface, and/or contamination of such other surfaces with the substance. Moreover, the use of such articles to manually apply a substance to a surface of an object frequently results in exposure of a user's hands to the substance. At the very least such a scenario results in a waste of product and is undesirable from an aesthetic standpoint and, at worst, results in excessive exposure of the user to potentially harmful, toxic, or otherwise undesirable substances.

Other common approaches involve dispensing a substance such as a cleaner or protectant from a bottle or other closed vessel onto the target surface, then utilizing a sponge, towel, brush, or other implement to distribute the product on the surface and, if desired, absorb any excess product, potentially with another implement or substrate. Such practices are commonplace with surfaces such as glass, countertops, and other kitchen and bathroom surfaces. While such practices are widely accepted, they often result in inefficient use of product and/or contact with the substances involved. Moreover, utilizing such an implement typically only provides one type of material surface for use in contacting the substance and the target surface. Applying the substance to the applicator from a vessel at the point of use likewise often results in inefficient use of product and/or contact with the substances involved.

A common approach to cleaning glass or other surfaces, for example, is to spray cleaning solution onto the surface and then wipe the surface with a paper towel. Spraying the cleaning solution usually wastes some of the cleaning solution due to over-spray landing on areas not intended to be cleaned. This over-spray is often undesirable since some surfaces can be harmed by this cleaning solution or at a minimum requires additional surfaces to be cleaned. The paper towel is used to both spread the cleaning solution on the surface as well as absorbing any excess. The paper towel has a difficult time spreading the cleaning solution since it is typically designed to be highly absorbent. To compensate, a disposable paper towel can be made partially saturated making it easier to spread the cleaner. This however typically makes the towel weaker due to a paper towel's lack of wet strength. Then a separate dry paper towel can be used to buff the glass dry and to absorb any excess cleaner. This approach requires more cleaning solution to be applied and requires more paper towels than desired. To compensate for this approach some consumers use newspaper quality paper or low absorbency paper towels. This type of paper has a lower absorbency level and naturally does a better job of spreading the cleaning solution instead of absorbing the cleaner into the paper towel. Also these types of towels have a stiffer and harder furnish which tend to aid in buffing the glass to a streak-free shine. However, this approach is less desired because special paper towels are required and a lot of buffing is required to get the desired end result.

Accordingly, it would be desirable to provide an applicator for applying a substance to a target surface that permits greater control by the user during the application process.

It would also be desirable to provide such an applicator that permits the user to apply a substance to a target surface with reduced messiness and waste of the substance.

It would further be desirable to provide such an applicator that provides multiple surfaces of diverse materials and/or multiple substances for use in multiple tasks.

It would further be desirable to have an implement that had one side suitable for spreading cleaning solution with minimal effort and good wet strength and another side suitable for quickly absorbing any excess cleaner and buffing a surface to a streak-free shine. It would also be desirable to have an applicator that eliminates over spray and avoids wasting cleaning solution.

SUMMARY OF THE INVENTION

A semi-enclosed applicator for distributing a substance onto a target surface is disclosed having a first side having a first internal surface and a first external surface; a second side having a second internal surface and a second external surface; an internal cavity between the first and second internal surfaces that is externally accessible, and a temperature changing element. The flexible film pouch contains a product located proximately to said first side.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements, reference numerals with the same final two digits identify corresponding elements, and wherein:

FIG. 6 is a plan view of a further embodiment of a rupturable reservoir suitable for use in accordance with the present invention;

FIG. 7 is a plan view of a further embodiment of a rupturable reservoir suitable for use in accordance with the present invention;

FIG. 8 is an elevational view of the rupturable reservoir of FIG. 7;

FIG. 9 is an elevational view of the rupturable reservoir of FIG. 8 folded in the vicinity of the rupturable seal;

FIG. 10 is an elevational view of an applicator similar to that of FIG. 3 which is folded in the vicinity of the rupturable seal of the rupturable reservoir;

FIG. 11 is a cross-sectional view of an applicator similar to that of FIGS. 1 and 2, but illustrating the use of rugosities on at least one surface;

FIG. 12 is a partial perspective view of one material useful in forming the rugosities of FIG. 11;

FIG. 15 is a schematic illustration of an applicator manufacturing process in accordance with the present invention;

FIG. 16 is a plan view of the process of FIG. 13;

FIG. 48 is a plan view of one embodiment of a rupturable two component heating or cooling reservoir with an integral product dispensing reservoir suitable for use in accordance with the present invention;

FIG. 49 is an elevational view of the rupturable heating, cooling, and dispensing reservoir of FIG. 48;

FIG. 50 is an elevational view of the rupturable heating, cooling, and dispensing reservoir of FIG. 48 folded as when assembled into a mitt;

FIG. 51 is an elevational view of the rupturable heating or cooling reservoir of FIG. 46 adjacent to the rupturable reservoir of FIG. 4;

DETAILED DESCRIPTION OF THE INVENTION

As used herein, the term "hand article" refers to a covering for the hand or portion of the hand such as a finger or thumb. The term "disposable" is used herein to describe hand articles that are not intended to be restored or reused (i.e., they are intended to be discarded after a single use or a limited number of uses, and preferably, to be recycled, composted or otherwise disposed of in an environmentally compatible manner). As used herein the term "glove" refers to a covering for the hand having separate sections for each finger. As used herein, the term "mitt" refers to a covering for the hand having an enclosure that leaves some or all of the fingers partially or wholly unseparated and that may include space for the thumb in the main enclosure or may provide space for the thumb in a separate enclosure for the thumb or may not include a thumb enclosure at all. This term is also applicable to an apparatus which covers only one or more digits of a user, such as in the case of a "finger mitt" as described below. While the terms "glove" and "mitt" have been defined with respect to the human hand, similar structures could be utilized to cover or enclose other elements of human anatomy, such as foot coverings, or other items for which coverings of a particular shape are preferred. As used herein, the term "absorb" refers to the penetration of one substance into the mass of another. ASTM D2654-89a "Standard Test Methods for Moisture in Textiles" should be used to determine the percentage of a liquid, such as water, absorbed and retained. An absorbent fiber for the purposes of the present invention has a moisture regain according to ASTM D2654-89a of greater than about 5% (e.g., a cellulose acetate fiber having a moisture regain of about 6.5%). A non-absorbent fiber for the purposes of the present invention, however, has a moisture regain of less than about 5% (e.g., a polyester fiber having a moisture regain of about 4%). As used herein the term "substantially non-absorbent" is defined as a material composed of a majority of non-absorbent fibers or webs. As used herein the term "substantially absorbent" is defined as a material composed of a majority of absorbent fibers or webs. As used herein the term "extension force" refers to forces applied by hand movements to a surface to extend and/or bend that surface linearly and/or curvilinearly. The term "pouch" or "sachet" is intended to refer to a reservoir made from flexible film that is bonded to create one or more enclosed compartments for containing a substance.

The term "semi-enclosed applicator" is intended to refer to an applicator device having at least one externally-accessible internal cavity for receiving a portion of human anatomy such as a hand or finger so that the applicator device may be used as an implement. A glove, mitt or finger mitt would be an example of such a semi-enclosed applicator in the context of the present invention.

Figure 1:
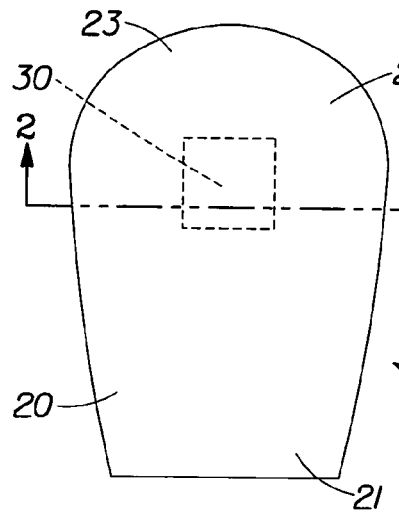
FIG. 1 is a plan view of a preferred embodiment of a semi-enclosed applicator in accordance with the present invention, in the form of a mitt.

Applicator Construction and Operation:

A representative embodiment of a semi-enclosed applicator of the present invention in the form of a hand article is the disposable mitt 10 shown in FIG. 1. FIG. 1 is a plan view of the mitt 10 of the present invention in its flat-out state illustrating the body portion 20, cuff portion 21, central portion 22, distal portion 23, and reservoir 30. In general terms, the mitt 10 has an internal cavity that is accessible through at least one opening in the cuff portion and that extends inwardly toward the distal end that is closed.

Figure 2:
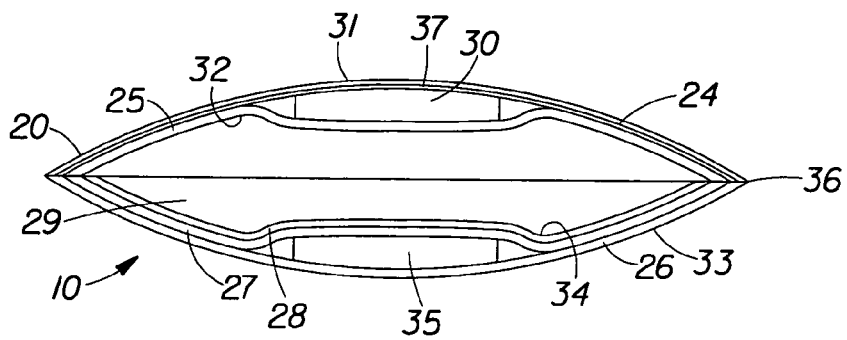
FIG. 2 is a cross-sectional view of the mitt of FIG. 1 taken along line 2—2.

FIG. 2 shows the construction details of the mitt 10 more specifically. The mitt 10 has a front outer surface 31, a front inner surface 32, a back outer surface 33, and a back inner surface 34. The front and back inner surfaces define a hollow interior 29 into which a hand may be inserted through an opening in the cuff portion 21. The mitt 10 includes a front panel (or first side) 24, which defines the front outer surface 31, and a back panel (or second side) 26, which defines the back outer surface 33. The front and back panels are connected along their periphery to form a seam 36. The seam 36 can be straight or may be tapered. For example, the seam 36 in may be inwardly tapered in the area of the cuff region to allow the applicator to stay on the hand of the user better. In addition to, or in place of, tapered seams, elastic material may be added in the cuff region to keep the applicator on the hand of the user.

A semi-enclosed applicator of the present invention may be constructed for many different uses. Unlike conventional cleaning implements, the applicators are ideally suited for cleaning curved or other surfaces with jagged edges or tough to reach areas. As a result, the product form provides convenience not only because it may comprise multiple different surfaces that may perform complementary tasks such as wetting, cleaning, drying and/or buffing surfaces, but also because it provides a means of doing the job on tough to reach areas or surfaces. Such a combination of benefits is lacking in present day cleaning systems. The mitts can be stored individually, or placed and stacked in containers, folded or unfolded. As such, they occupy little space and can be stored in small areas, which improves convenience for the users. The combination of easy storage and ability to clean tough to reach areas such as the interior of car windows, dashboards steering wheels and mirrors, makes them ideal for use in the car (glove compartment storage), where conventionally employed glass cleaning processes are awkward, ineffective and potentially hazardous.

Reservoir

The reservoir 30 contains a product that may be dispensed and/or dispersed from the reservoir 30 to one or more of the outer surfaces of an applicator, such as outer surface 31, for delivery to a target surface. The fluid reservoir 30 may be of any suitable size, configuration, and composition for the intended product to be dispensed and dispersed. The product may be a liquid, a gel, a lotion, a cream, a powder or even a solid. A solid such as a wax, for example, may be heated to provide a flowable product that may be dispensed and/or dispersed from the reservoir 30. One aspect of the reservoir 30, which is believed to be important to the overall functionality of the mitt 10, is the ability of a sealed, fully-enclosed reservoir to rupture or otherwise dispense the product contained therein when "activated" by the user and yet resist premature dispensing during manufacture, packaging, and shipment. In alternate embodiments, the reservoir may be located at least partially outside of the applicator 10. For example, chamber 47 of reservoir 30 of FIG. 7 might extend outwardly from an applicator for improved visual and manual access, as desired. The ability of the reservoir to survive intact until the point of use preserves the quality and quantity of the liquid until the time of use. As will be understood, external accessibility to a reservoir might also facilitate the provision of crimping devices, folding of a reservoir or other protection of the reservoir against premature dispensing, as will be discussed further below. Alternatively, the reservoir 30 may be a separate article that can be inserted into the mitt 10 by the user. For example, the reservoir 30 may be inserted inside of the front panel 24 or the back panel 26 of the mitt 10 or may be inserted into one or more pockets located between the front outer surface 31 and the front inner surface 32 that are designed to receive the reservoir 30. This allows the user to replace reservoirs 30 as needed and provides for reuse of the mitt 10 if it retains sufficient absorbency, wet strength, etc.

In one embodiment, the reservoir can be designed to burst or rupture to release the product contained within the reservoir at a comparatively low force when desired by the consumer. This may be accomplished by having a sealed pouch with permanent seals and also seals that are "frangible", i.e., rupturable. When the pouch is squeezed, the frangible seal will yield or fail first since it has a lower peel force to break the seal apart than the permanent seals. In one embodiment, the frangible seal will ideally rupture with 1–3 lbs of force when applied by the consumer. Adding stress concentrators in the seal geometry that will localize forces at a particular location can optimize the location of rupture. These stress concentrators can be shaped like a V, a notch, a half circle or a variety of other shapes depending upon the desired burst level. These stress concentrators will help control the force required to burst the pouch as well as the location of where the seal will rupture. Such stress concentrators thereby focus or concentrate external pressure or mechanical forces imposed on the reservoir and its contents. For example, pressurizing a pouch having a V-notch seal such as shown in FIG. 7 will localize forces first at the apex of the V, causing that region to rupture first. Such an arrangement can help reduce potential variability in rupture or dispensing forces and the location where the rupture occurs. Additionally, other seal angles and geometries of the seal can also be used to tailor dispensing forces for particular applications.

Figure 3:
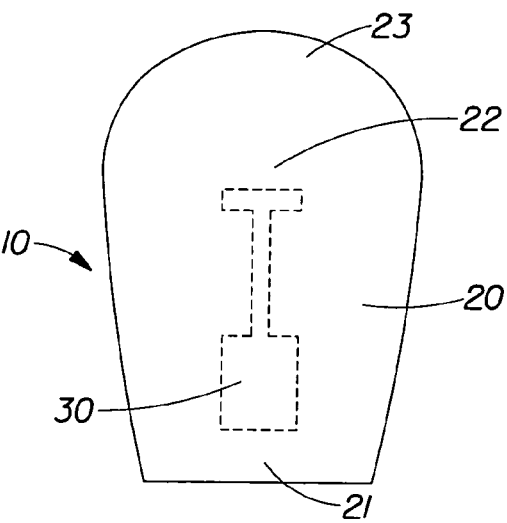
FIG. 3 is another embodiment of a semi-enclosed applicator in accordance with the present invention, also in the form of a mitt.

In the embodiment of FIG. 1, the reservoir 30 is positioned in the central portion 22 of the mitt 10. In this location, the reservoir 30 can be subjected to sufficient force to rupture the reservoir and dispense the liquid by making a fist with the user's hand, by applying force with the opposite hand, or by pressing the palm against the target surface. This location of the reservoir 30 in the applicator is convenient for applications where it is desired for the product to be dispensed all at once or while rubbing a surface. It may also be desired to have the reservoir located in a portion of the applicator that is spaced or remote from a location where forces are applied during cleaning or rubbing. In this manner, pressure applied to the mitt during cleaning or rubbing will not cause premature dispensing or dosing of the product in the reservoir 30. FIG. 3, for example, depicts an alternative embodiment of a mitt 10 wherein the reservoir 30 is positioned closer to the cuff region 21. In this location, the reservoir 30 is not located in a region of the mitt that would typically encounter forces in use (the application or pressure region), and the reservoir 30 would require activation by specifically applying force to the cuff region. Such an embodiment may be particularly advantageous where progressive dispensing of discrete quantities of the product is desired rather than an "all at once" dispensing upon application of an initial force.

The use of a reservoir to contain a product allows the applicator to become wet on the desired side only when wanted by the person using the applicator. In some cases a person would like to store a single applicator in a remote site such as a glove box in a car or in a separate drawer in a bathroom. The hermetically sealed reservoir(s) in the applicator preferably use sufficient barrier materials to allow these individual applicators to have multi-year shelf life even when stored as individual units. Separately, the reservoirs can be placed on one or both sides of the applicator or in multiples on the same side. This allows one side to be kept dry or to have different products on the different sides. In contrast, pre-moistened wet wipes that have been individually wrapped are traditionally placed in a foil pouch. This foil pouch material is expensive and more of it is needed to enclose the entire wipe to prevent moisture loss (with the individually enclosed reservoir, foil film is only needed to enclose the liquid or substance). This approach of putting the entire pre-moistened applicator (wipe) in a foil pouch also makes it difficult for the wipe to have a dry surface or from having surfaces with two different substances since cross-contamination is likely to occur.

Figure 4:
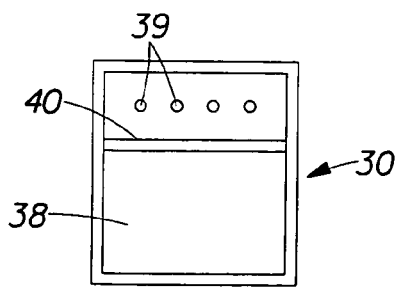
FIG. 4 is a plan view of one embodiment of a rupturable reservoir suitable for use in accordance with the present invention.

FIG. 4 illustrates one suitable configuration for a rupturable reservoir 30 suitable for use with applicators according to the present invention, such as the applicator of FIG. 1. In the embodiment of FIG. 4, the reservoir 30 includes a chamber 38, a frangible seal 40, and at least one dispensing aperture 39. The embodiment of FIG. 4 may be made by peripherally joining two similarly-sized and shaped pieces of fluid-impervious material with substantially permanent seals, forming the dispensing apertures in one portion of at least one of the pieces of material, introducing the product through one of the apertures, and then forming a frangible seal of limited strength to separate the chamber 38 from the apertures 39. Other forming techniques, such as folding a single piece of material double upon itself and sealing, or rolling and sealing a piece of material to form a sleeve, may also be utilized.

Figure 5:
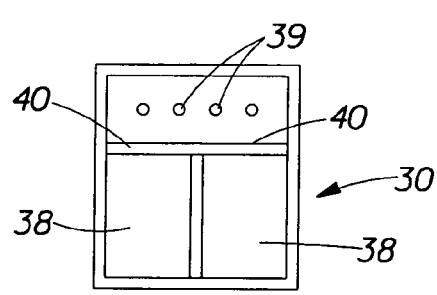
FIG. 5 is a plan view of another embodiment of a rupturable reservoir suitable for use in accordance with the present invention.

FIG. 5 depicts another embodiment of a reservoir 30 that is functionally similar to that of FIG. 4, but including a plurality of chambers 38 for containing liquid. Respective chambers 38 may include product(s) of the same, similar, or diverse compositions, and may be designed to be ruptured sequentially or simultaneously depending on how pressure or squeezing is applied by the user. FIG. 6 is a further embodiment having a plurality of chambers 38, but wherein the chambers are themselves separated from one another by the rupturable seal 40. In such an embodiment, the chambers would typically be released concurrently, such as to mix the products from respective compartments at the time of dispensing.

The mitts of the present invention may have a burstable reservoir that has multiple chambers for mixing incompatible products. This would allow the ability to deliver superior cleaning performance as an example at an affordable cost. For instance, a chamber could have a bleach formula suitable for killing mildew, and germs and the other chamber could contain surfactants and cleaning solutions suitable for removing dirt and soap scum. The ideal formulas for these two different tasks are incompatible for a long period of time (like on a store shelf), but can be mixed right before use (like in the mitt) or can be dosed sequentially to deliver superior cleaning performance of nearly any type of bathroom stain. The same could be done for a variety of other uses like a disposable finger toothbrush that dispenses baking soda and peroxide on a "finger" mitt that allows these two products to be mixed to deliver superior teeth cleaning in a disposable package for away from home occurrences. The back side of the mitt could have a post-treatment for whitening the teeth.

Figure 20:
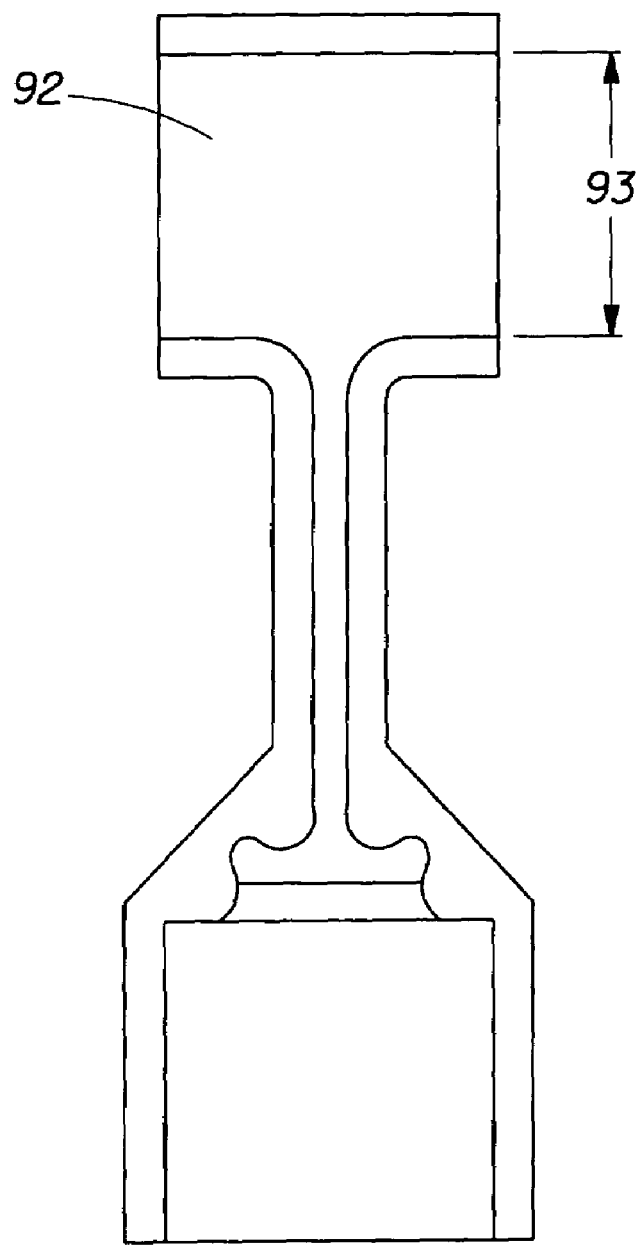
FIG. 20 is a plan view of a further embodiment of a rupturable reservoir suitable for use in accordance with the present invention.
Figure 21:
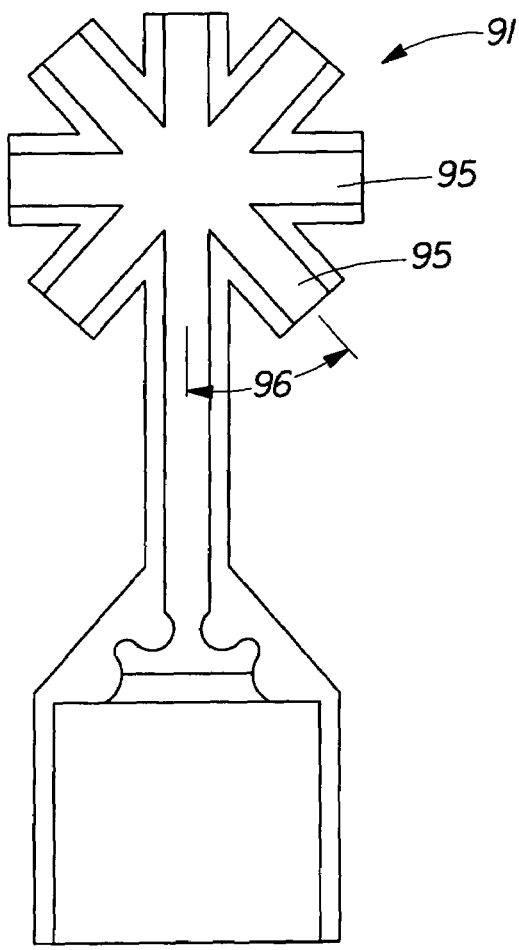
FIG. 21 is a plan view of a further embodiment of a rupturable reservoir suitable for use in accordance with the present invention.
Figure 24:
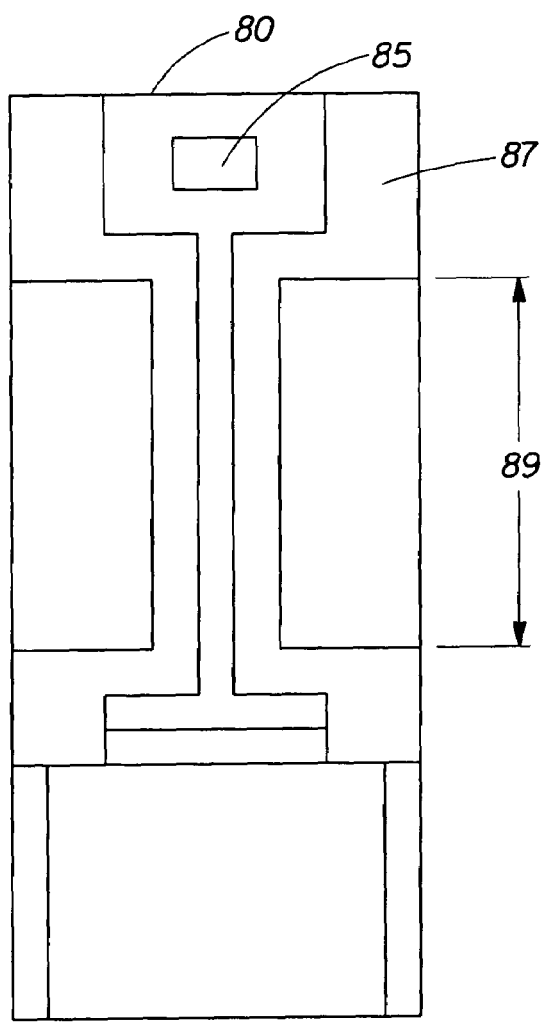
FIG. 24 is a plan view of a further embodiment of a rupturable reservoir suitable for use in accordance with the present invention.

More advanced product distribution functionality may be designed into the reservoir and/or to the applicator. The bursting pouch may also have an integral distribution head (such as illustrated as channel 44 of FIG. 7) that allows the product to be dispensed and dosed to different portions of the mitt. This distribution head is ideally an extension of the pouch material that has been sealed in a way to form channels for the product to flow to another region. The distribution head may have holes in the sides for the product to exit or may have several seals that force the product to chance direction minimizing the velocity of the product exiting and thus eliminating or reducing uncontrolled spraying of the product out of the mitt. Other arrangements, such as the inclusion of baffling structure to divert or control the fluid might be desirable as well, such as where products of low viscosity are dispensed. FIG. 20 shows one alternative embodiment of a distribution head 92. In this embodiment, the sides are slit the entire length 93 and are thus coupled with the large area allowing product to spread greatly within the head before releasing onto the mitt. Thus, this distribution head embodiment maximizes wicking and allows product to slowly weep out. The distribution head can be modified greatly to match desired product delivered. FIG. 21, for example, shows several "fingers" 95 protruding from the dosing head 91 thus allowing product to be delivered directly to various locations. The number of fingers 95, the angle 96 with respect to the dosing head 91, and the length of each finger 95 can be modified independently to achieve the desired delivery pattern. FIG. 24 shows another example of a distribution head that aids in delivering a desired dosing effect. Similar to some versions of the distribution head that slow product release by changing the direction of the product flow and providing exit locations larger than the delivery channel, such as shown in FIGS. 20 and 21, this particular embodiment utilizes a seal 85 in the center that acts as a baffle to prevent-product from exiting too quickly or with too much force and running off the substrate. The end 80 is not sealed and serves as the exit location. The side seals 87 force the fluid forward as it is released from the pouch; thus, directing fluid to the desired location. For example, this reservoir would be useful in delivering product near the fingertips in a mitt while still allowing the delivery channel length 89 to be minimized. Alternatively, one or more of the sides may not be sealed and serve as an alternate or as an additional exit location for the fluid.

FIG. 7 is one example of a more complex reservoir design. The reservoir 30 of FIG. 7 includes a plurality of outlet ducts 41, a plurality of distribution apertures 42, and an elongated channel 44 which separates the chamber 47 from the distal end 43 of the assembly. Fluid flow between the chamber 47 and the channel 44 is controlled by the frangible or rupturable seal 45, which illustrates the use of a stress-concentration notch 46. The channel 44 may be of a material and configuration such that it is "self-sealing" and collapses shut to restrict, if not preclude, fluid flow except when the chamber is substantially pressurized. For example, a channel may be formed by making two substantially parallel seals along facing layers of a pouch, where the space between these seals becomes a channel for fluid to move from the reservoir to the distribution aperture(s). The channel will naturally lay flat (and thereby closed) due to the seals, but will become almost tubular when the reservoir is pressurized and filled with fluid traveling through the channel. Upon release of the pressure, the channel will tend to naturally return to its flat state, causing a sealing effect to prevent further product delivery. The dimensions of the channel may be optimized based upon the viscosity of the product being dispensed from the reservoir. For example, a reservoir designed for dispensing a powder or a relatively thick lotion or cream product will preferably have a wider channel than a reservoir designed for dispensing a relatively lower viscosity product such as a predominantly water or alcohol based product. In one embodiment, for example, the channel width is preferably in the range from about 0.125 inches to about 0.5 inches wide, more preferably about 0.25 inches, to allow "resealing" of the channel while not requiring excessive force on the pouch to pressurize the channel. Resealing of the channel may provide for dosing or progressive fluid dispensing. The outlet ducts and/or the apertures may be used as desired, with one or the other being employed or both in combination. Other approaches to provide dosing capability (i.e., multiple discrete dispensing cycles) include providing multiple reservoirs on either or both sides of the applicator.

Figure 19:
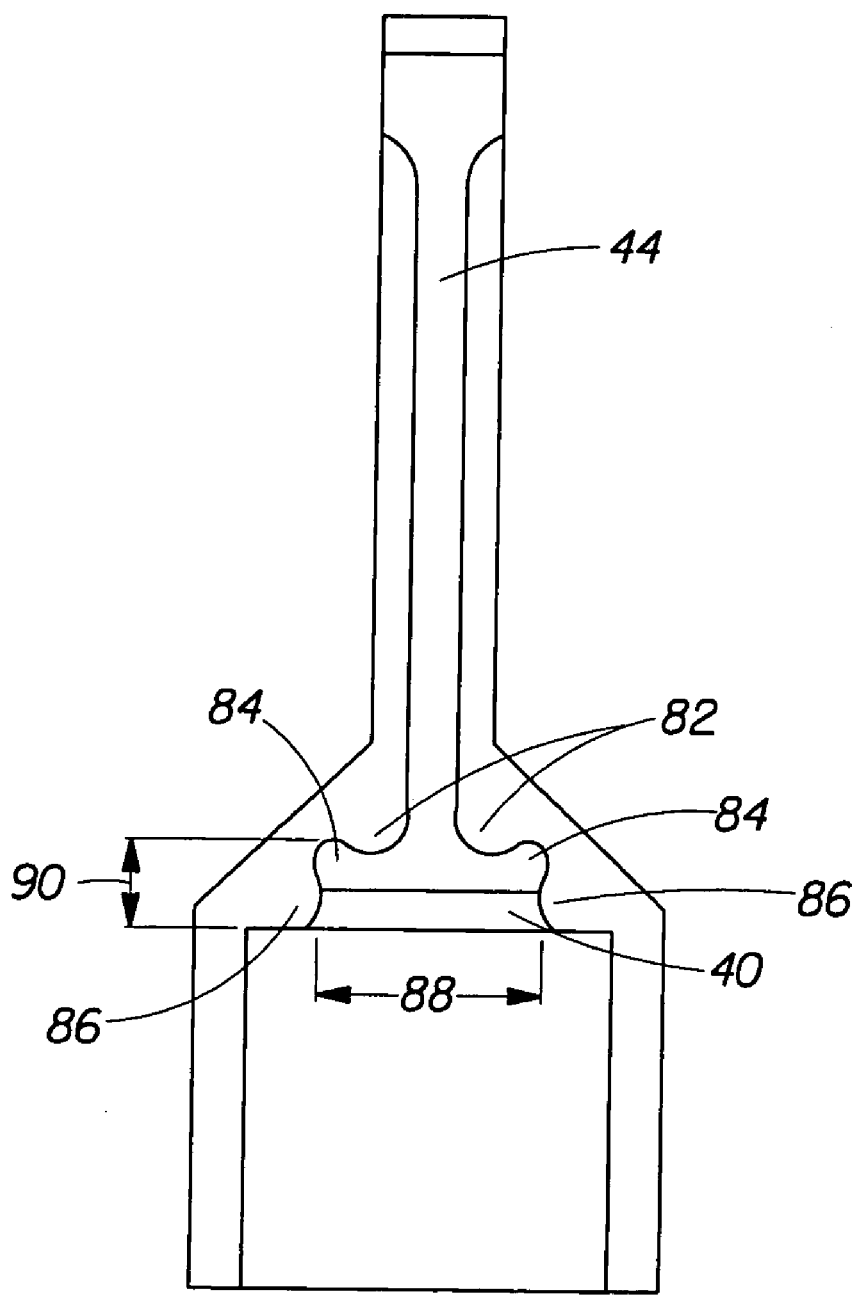
FIG. 19 is a plan view of a further embodiment of a rupturable reservoir suitable for use in accordance with the present invention.

Additional functionality may be added by providing dosing. FIG. 19, for example, shows one such embodiment with additional features for controlling dosing. Areas 82 of the lock up seal aid in the prevention of over-dosing by inhibiting fluid flow through the dosing channel once activated. Thus, the user feels an increase in resistance when squeezing or pressing the pouch. Areas 84 are preferably not sealed and extend beyond the end of the dosing channel. Once the cell is pressurized, these areas 84 fill and provide a more rigid three-dimensional structure to the cell and prevent the channel from folding and clamping shut. Areas 86 of lock up seal can be added to provide a "target zone" for the frangible seal. Thus, burst force consistency is improved by limiting the width 88 of the frangible seal 40 and manufacturing is made easier by having a larger zone 90 where the frangible seal can be located. Area 86 also aids in forming a natural fold line for protecting the frangible seal.

Dosing may alternatively be accomplished without the use of a dosing reservoir or distibution channel. For example, a rupturable reservoir such as shown in FIG. 4 may be combined with a flow restriction layer. The flow restriction layer may be a separate layer in the mitt 10 such as the front panel surface 24, the layer 37, or be an additional layer that is between layer 37 and the reservoir 30. Nonwovens, apetured films, thermoformed films, and other materials, for example, can be created to have a target porosity and thus fluid flow rate. Controlling the mean pore size of openings and the number of openings in the flow restriction layer can determine how fast a fluid or product will be dispensed through the front or back panel. The fluid flow rate can be controlled by incorporating the desired porosity in the front or back panel materials or can be accomplished by having a separate layer or layers between the reservoir 30 and the application surface of the mitt 10. An example of a flow restriction layer is a 100 mesh hydroapetured film made from low density polyethylene. The apertures in this structure are approximately 100 micron in diameter and may be suitable for controlling the fluid rate of creams and lotions, for example. The number and size of the holes can be adjusted depending upon the viscosity of the fluid being dispensed and the desired application rate.

Figure 18:
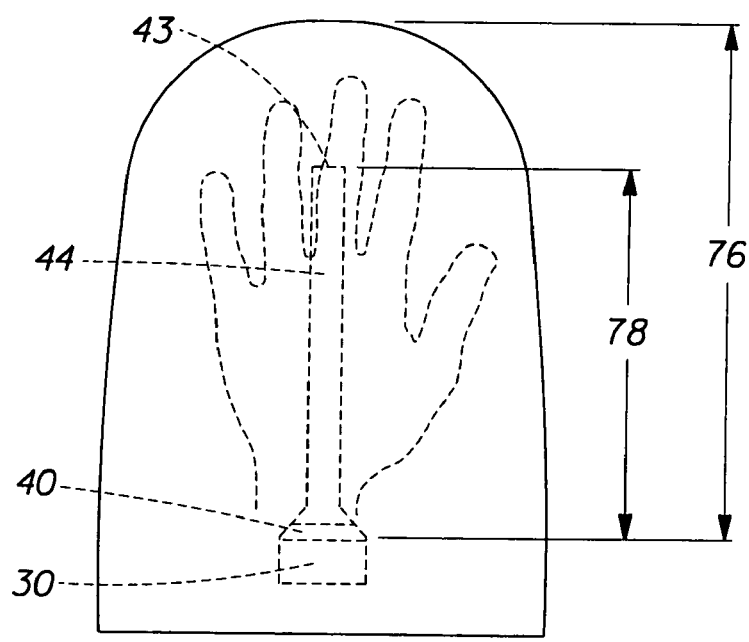
FIG. 18 is a plan view of a further embodiment of a semi-enclosed applicator in accordance with the present invention, also in the form of a mitt.

A reservoir 30 having a frangible seal connected to a distribution channel 44 such as shown in FIG. 7, for example, can provide fluid communication with one or more distribution apertures located in a region or application surface of the mitt removed from the location of the reservoir 30 itself. As shown in FIG. 18, for example, a reservoir 30 can be located near a cuff region of the mitt such that the reservoir 30 and the frangible seal 40 are located below the palm of the wearer's hand and the distribution channel 44 provides fluid communication to a portion of the mitt corresponding to the position of a user's fingers in use. In one embodiment, the distance 76 from the tip of the closed side of the mitt 10 where the fingers of the wearer's hand are located to the frangible seal 40 can be in the range from about 6.5 inches to about 8.5 inches thus allowing the frangible seal to remain clear of the pressure applied by the palm of the wearer's hand of about the 97.5 percentile of women (7.5 inches) and of the 97.5 percentile of men (8.2 inches). See, e.g., Dreyfuss, Henry, "The Measure of Man", New York; Whitney Library of Design (1969). This location, for example, can space the reservoir away from the region of the mitt that would typically encounter application and scrubbing forces in use, and may allow for sequential dosing of the product in the reservoir by requiring activation by specifically applying force to the cuff region for selectively dispensing the fluid. In this embodiment, the fluid would travel through the channel to the distribution head where the fluid is released on the desired location of the mitt, such as near the fingers in the preferred embodiment. The channel length 78, e.g., the distance from frangible seal 40 to the distribution head 43 shown in FIG. 18, is preferably in the range from about 0.5 inches to about 8.5 inches long, more preferably in the range from about 3.5 inches to about 5 inches long.

The reservoir preferably uses a laminate film that contains either metallized PET, aluminum foil, $SiO_2$ or some other high barrier material that will provide an adequate moisture and/or oxygen barrier to allow the product to have a reasonable shelf life. In one embodiment, for example, the reservoir may have a shelf life in the range from about 2 years to about 3 years. Smaller reservoirs with small amounts of a product require even a higher barrier since the surface area to volume of fluid is significantly higher resulting in higher levels of moisture loss due to transport and diffusion.

The reservoirs can be made rupturable or "frangible" by a number of different techniques. One preferred technique is to make a pouch on a vertical or horizontal form/fill/seal machine that has the ability to make different seals on the pouch at different temperatures, pressures or seal times. This allows one side of a pouch to have different sealing conditions that in turn can allow one side to have a weaker seal strength. A suitable sealant material for this type of "frangible" seal would be Surlyn® made by Dupont or a blend of Polybutylene with Ethylene Vinyl Acetate or ultra low density ethylene copolymers, polyolefin plastomers, and/or Polyethylene. Sealant layers made with either of these resins or blends will result in a sealant layer that will have significantly different seal strengths depending upon the seal temperature. The blend provides a "contaminant" to the base polymer material that allows the resulting seal to be selectively frangible under certain sealing conditions. For example, at 200 degree F. the sealant layer will deliver a seal force of 200–400 grams/linear inch of seal width and at 300 degree F. the seal force will deliver a seal force closer to 3000 grams/linear inch of seal width. This variation in seal strength allows a pouch to be "welded" shut in one portion and easily burstable in a second portion just by adjusting the seal temperature, the seal time and/or the seal pressure used when making the pouch seals (e.g., the pouch may be welded along all or a portion of one, two, three or more sides and easily burstable along a portion of one, two, three or more sides). A preferable film structure for this type of frangible reservoir would be Surlyn sealant/tie layer/metallized PET. Other techniques for making the consumer activated rupturable reservoirs include delaminating seals, weak regions in the film structure such as created by embossing, laser scoring, mechanical scoring or other known methods of weakening a film structure, and small thermoformed cells with thin regions that rupture when squeezed (similar to bubble wrap). Alternatively, a reservoir 30 may have other opening means such as tear-off strips, pull tabs, release liners and the like.

Front Panel

In accordance with one embodiment of the present invention, the front panel 24 preferably comprises a porous, such as a fibrous nonwoven, material through which the product within the reservoir 30 can be dispensed. Another applicable material would include an open cell polyethylene or polyurethane foam, such as available from Sentinel Products Corporation of Hyannis, Mass. In embodiments in which the product is a liquid, the material utilized for the front panel 24 is preferably substantially non-absorbent and/or preferably substantially hydrophobic when utilized with water-based liquids, in order to provide for residence time of the liquid upon the target surface. Non-absorbent fibers in a nonwoven, for example, do not absorb water and thus do not swell when exposed to an aqueous based product. Exemplary fibers that may be used, in a nonwoven include polyolefin, such as polyethylene and polypropylene, and polyester fibers. An acceptable nonwoven can be made, for example, by known methods such as spunlace, spunbond, meltblown, carded, air-laid, hydroentangled, and the like. Alternatively to a porous nonwoven, an apertured film or web can also be used as a porous non-absorbent material for the front panel 24. Suitable materials for use as a front panel 24 can also provide sufficient strength and texture characteristics so as to provide a scrubbing action upon the target surface and to maintain web integrity when exposed to the product. In embodiments such as where the product within the reservoir 30 is a liquid or where the front panel is exposed to a liquid during use, the front panel 24 preferably comprises a material that has a good wet strength, durability for scrubbing, low product retention characteristics, and that will not scratch or damage the target surface. A thermoplastic-based non-woven substrate such as a polypropylene, polyethylene, or polyester based non-woven substrate, for example, can effectively meet these criteria while also not absorbing water based product formulas. One such material sufficient in durability and strength to provide a cleaning surface, for example, is a spunbond polypropylene non-woven such as from BBA Nonwovens of Simpsonville, S.C. Other structures such as hydroentangled materials comprising cellulose, rayon, polyester, and any combination thereof may also be used. One such set of materials are made by Dexter Corporation of Windsor Locks, Conn. and sold under the trade name Hydraspun®. One skilled in the art will understand that a wide range of materials can be used as long as the material of interest provides the required durability to complete the particular task.

In one embodiment, the fiber diameter may be less than about 100 microns, alternatively less than about 50 microns and in yet another embodiment may be in the range from about 10 microns to about 35 microns. A higher number of smaller diameter fibers can aid in holding onto dirt via mechanical entanglement and can also yield a softer substrate. The basis weight of the front panel 24 may preferably be in the range from about 10 gsm to about 100 gsm, more preferably in the range from about 15 gsm to about 55 gsm, and even more preferably in the range from about 25 gsm to about 45 gsm. In some embodiments, the fibers can also hydrophobic, oleophillic, and positively charged that aid in holding onto dirt, oils and other contaminants that are desired to be removed from the surface. An oleophillic material that oils naturally attach themselves to is preferred.

Preferably, the fibers also maintain their positive charge even when wet. One approach to achieve this positive charge is to coat the fibers with a treatment of a cationic polymer such as polyacrylamide (PAM), polyethylenimine (PEI), polyvinylpyrrolidone (PVP), polyamide epichlorohydrin (PAE). A PAE resin, produced by Hercules under the tradename Kymene® is one such material. For example, in a glass cleaning and/or general multiple purpose surface cleaning embodiment, polypropylene or poylethylene nonwovens have been found to be good materials for applying a cleaning formula to glass, shiny surfaces and other surfaces.

Figure 60:
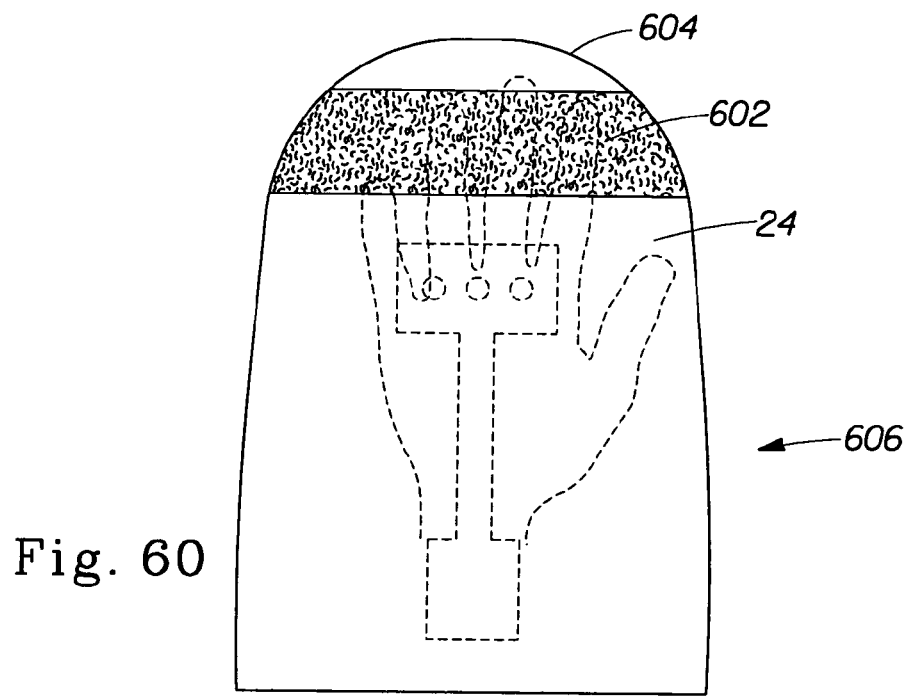
FIG. 60 is a top plan view of a mitt with an optional scrubbing strip attached to front panel.

Further, in one embodiment, the front panel can include fibers or porous materials that may provide additional strength and scrubbing capability. Fibers such as polyester (PET) fibers, for example, can be utilized. Alternatively, or in addition to such fibers, a strip of material for scrubbing can be formed directly on the front or back panels or may be added onto the front or back panels. One suitable material for additional scrubbing that may be used is a chemically bonded PET nonwoven with a binder that has a mild level of abrasiveness. The level of abrasiveness may be modified by changing the binder composition and amount as well as the fiber type and diameter. An exemplary material may include a 30 gsm chemically-bonded air-laid PET nonwoven having a formaldehyde based binder made by Stearns Technical Textiles of Cincinnati, Ohio. FIG. 60, for example, shows a strip 602 bonded to the front panel 24 near the top 604 of a mitt 606. In this example, the front panel 24 may be a 30 gsm polyethylene spunbonded nonwoven that may not have the desirable durability for a particular scrubbing application. The strip 602 may provide additional durability of the mitt and may be used for scrubbing such as removing difficult soils from a target surface such as dried bugs and other difficult soils on a car windshield.

A nonwoven typically does not swell with the product and releases the product when rubbing with minimal retention compared to a disposable paper based towel. Further, a thermoplastic nonwoven has good wet strength and adequate scrubbing capability yet will not scratch many target surfaces. The nonwoven also has a low coefficient of friction that allows the substrate to glide very easily across a target surface with minimal effort and allows good ease of spreading the product onto the target surface.

In view of the fact that polypropylene non-woven materials, and many other suitable materials for front panel 24, are highly porous and rapidly penetrated by liquid products, the mitts of the present invention designed for use with liquid and other low viscosity products may optionally include an absorbent layer, such as tissue paper layer 37, between the reservoir 30 and the front panel 24. The absorbent material can absorb and wick the product, distribute the product beyond the dimensions of the reservoir and supply the product to a larger surface area of the outer layer, e.g., front panel 24. Depending upon the viscosity of the product and the desired surface area to supply the liquid, absorbent layers with different capacities and wicking rates can be used to control product distribution. The basis weight of the absorbent layer may, for example, be less than about 60 gsm, preferably may be less than about 40 gsm, and more preferably may be in the range from about 10 gsm to about 30 gsm. One suitable material is a single ply of a disposable kitchen paper towel such as Bounty®, a product of the Procter & Gamble Company. If slower fluid transport is desired, higher capacity materials such as two ply Bounty® can be used. If faster fluid transport is desired, less absorbent materials such as Cellu Tissue 7020, a product of the Cellu Tissue Corporation of East Hartford, Conn. can be used as well as creped or other corrugated materials that aid in fluid transport. Those skilled in the art will understand that the absorbent material can be chosen from a wide range of absorbent materials so as to best meet the required capacity and wicking rate for a given embodiment.

Figure 22:
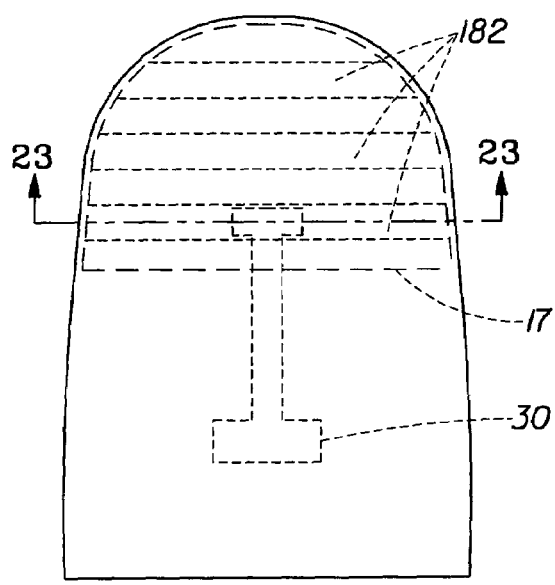
FIG. 22 is a plan view of a further embodiment of a semi-enclosed applicator in accordance with the present invention, in the form of a mitt.
Figure 23:
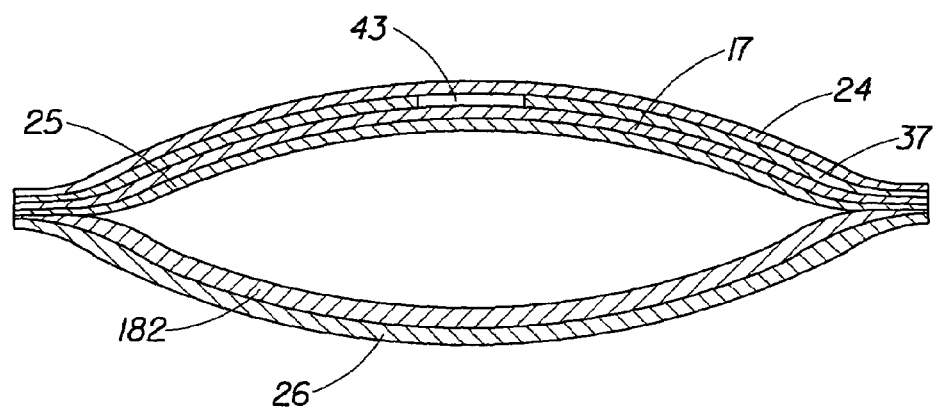
FIG. 23 is a cross-sectional view of the mitt of FIG. 22 taken along section line 23—23.

Another method to control liquid flow is to use a second absorbent layer, such as second layer of tissue 17, between the reservoir 30 and the internal fluid impervious barrier layer 25 as shown in FIGS. 22 and 23. Having layers 37 and 17 on both the front and back sides of the distribution portion of the reservoir 30 will help prevent fluid from running along the front sheet or the internal fluid impervious layer 25. If the absorbent layer is only on one side of the reservoir 30, the fluid may run along the internal fluid impervious barrier layer 25 away from the desired distribution portion of the mitt before the fluid comes into contact with the tissue paper layer 37. The tissue paper layers 17 and 37 may cover the entire surface of the mitt or may cover a portion of the surface of the mitt from the outlet of the reservoir to a region where it is desired to transport the fluid. For example, a two to six inch strip of tissue may comprise the second tissue paper layer 17 located between the fluid-impervious barrier layer 25 and the reservoir 30 and located from the top of the mitt to a region slightly below the reservoir outlet. The second tissue layer 17 will help prevent fluid from running along the fluid-impervious barrier layer 25 and will direct the fluid to the top of the mitt closer to the fingers.

Yet another method that can be employed to control liquid distribution onto the outer layer 24 is the patterning of adhesives into an array of lines, spirals, spots, or any other open pattern network of filaments to combine outer layer 24 to tissue paper layer 37, to combine tissue paper layer 37 to fluid impervious barrier layer 25, to combine tissue paper layer 37 to second tissue paper layer 17, and/or to connect second tissue paper layer 17 to fluid impervious barrier layer 25. In an embodiment in which the applicator contains vertical corrugations, described later, that the adhesive can be applied in an array of horizontal lines. These horizontal lines can be applied using slot coating hot melt equipment as well as spray hot melt applicators with the air turned off. While not wanting to be bound by theory, it is believed that the presence of horizontal adhesive beads channels the liquid in the horizontal direction while the vertical corrugations channel the liquid vertically. Thus, the combination of these channeling mechanisms allows liquid to be distributed at the same time in both the horizontal and vertical directions. Depending upon the desired liquid distribution for a given embodiment, the spacing of the adhesive lines can be changed. In a preferred embodiment, these adhesive lines are spaced from about 1 mm to about 10 mm apart, more preferably from about 2 mm to about 5 mm apart. The adhesive type and basis weight is dependent on the two materials being combined, compatibility with the liquid of interest, and the processing method. The adhesive basis weight will preferably be less than about 12 gsm, more preferably from about 0.1 µm to about 8 gsm. The adhesive type can be any of the type of water-based, solvent-based, hot melt, pressure sensitive, or others known in the art. For the preferred embodiment, a pressure sensitive adhesive made by Ato Findlay of Wauwatosa, Wis., product H2031, provides adhesion for combining layer 24 to tissue layer 37, tissue layer 37 to layer 25 and/or tissue layer 17 to layer 25. Other methods of patterning adhesives include gravure printing the adhesive into channels that direct the fluid flow. One such example is adhesive printed in the form of a star pattern originating at the tip of the fluid reservoir to direct fluid in a radial pattern onto the front panel 24 or in a partial radial pattern to direct fluid only in one direction. In combination or in place of adhesives, the attachment means to combine layers 24, 37, and 25 may comprise pressure bonds, ultrasonic bonds, mechanical bonds, or any other suitable attachment means oh combinations of these attachment means as are known in the art. In the same way adhesives can be applied to direct the fluid wicking, these bonding methods can create channels in the desired direction for fluid flow. While not wanting to be bound by theory, it is believed these channels are created when materials are heated in discrete areas effectively creating a seal that liquid cannot pass through and thus must flow around.

In order to protect the hand of the user from contact with the product during the dispensing and/or dispersing operation, the mitts of the present invention can include a barrier layer 25, the interior of which defines the front inner surface 32 that faces the wearer's hand during use. The barrier layer 25 is preferably impervious to the product contained in the reservoir 30. Suitable barrier materials include polymer films, such as polyethylene, polypropylene, EVA, and polymer blends or coextrusions, which may be rendered extensible by methods described below. Materials that are embossed, whether or not rendered extensible, provide improved tactile properties and greater control over the applicator in terms of contact and coefficient of friction with the hand. Preferably, the material and the surface alteration are made such that the coefficient of friction between the inner surface 32 and a wearer's hand is greater than the coefficient of friction between the outer surface 33 and the target surface. This reduces the likelihood that the mitt 10 may slip or rotate inadvertently in use. The barrier layer can also be combined with another "softness enhancing" material that provides additional comfort, softness and tactile feel to the user's hand on the front inner surface 32. Such materials can include, but are not limited to, fibrous (natural, synthetic or combinations thereof) and/or foamed materials.

Applicators such as mitts may be designed to deliver products to one or both surfaces, or be utilized independently with products applied via other sources to accomplish dispersion of the substance and, it desired, removal of the product from the surface by absorption. Applicators, however, may be similarly designed to direct products toward the opposite surfaces of the mitt after eversion, for example, if the mitt is used for one function, then turned inside out and then activated again to deliver fresh product from the former internal surface.

Figure 17:
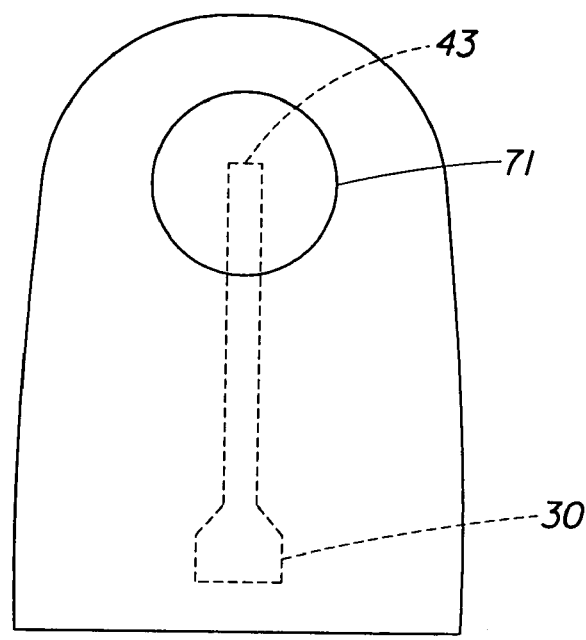
FIG. 17 is a plan view of a further embodiment of a semi-enclosed applicator in accordance with the present invention, also in the form of a mitt.

As fluid is released, it is often desirable for the user to be able to identify when the preferred amount of fluid has been released onto the front pane 24. This can be accomplished by incorporating a marking on the substrates to identify the surface area that would be covered by the preferred amount of dispensed product. This marking could be in the form of an ink mark, embossed pattern, or any means of visual identification on any or all layers of the substrates. In the embodiment shown in FIG. 17, for example, the marking 71 can be a circle centered around the distribution head 43 of the cell 30 such that when the preferred amount of product is dispensed, for example about 1–3 ml in some embodiments such as a window cleaning mitt, the diameter of the circle's perimeter corresponds to the surface area covered as the product wicks. The shape and size of the marking 71 could be varied based on the size and shape assumed: by the preferred amount of solution when dispensed within the particular embodiment of the mitt. For example, the use of different glue patterns that promoted faster wicking of the product in a particular direction could require that the shape be a larger elliptical pattern.

In some embodiments, the pouch is able to rupture at a relatively low force, such as in the range from about 1 pound to about 3 pounds, when the consumer is ready to use the mitt, but the pouch is able to survive relatively higher forces, such as in the range from about 10 pounds to about 40 pounds, when the mitt is in distribution to the store or handled in the box on the store shelf. This can be accomplished by folding the pouch on the frangible seal or between the frangible seal and the reservoir such that there is a mechanical advantage that occurs preventing the pouch from bursting and generally protects the pouch from undesired rupture and premature fluid dispensing. In some embodiments, for example, this technique has been shown to effectively raise the bursting force to a level in the range from about 30 pounds to about 40 pounds. This can be accomplished by folding the mitt into a compact unit, which also aids in packaging and shelf display. The mitt may be tri-folded such that the frangible seal is protected and the distribution head is also folded to provide an extra level of protection on the seal.

FIG. 8 is an elevational view of the reservoir of FIG. 7 and FIG. 9 illustrates the use of folding techniques to protect a frangible seal from premature rupture. FIG. 9 illustrates a reservoir 30 consistent with that of FIGS. 7 and 8 which has been folded at location 48 adjacent the rupturable seal 45. Folding the reservoir in effect crimps, or pinches off, the fluid pathway and is capable of withstanding significantly more internal pressure without leakage than would normally be desired for the frangible or rupturable seal relied upon for dispensing functionality.

FIG. 10 illustrates the tri-folding of an applicator 10 to isolate the fluid-containing reservoir 30. As shown in FIG. 10, the additional fold in the vicinity of the distal end of the reservoir 30 may serve to provide additional security against premature dispensing by isolating the fluid outlets from the remainder of the reservoir. Bi-fold, tri-fold, z-fold, or any suitable folding mechanism may be utilized to provide not only a more compact applicator, such as when a plurality of applicators are folded, stacked, and then placed within a carton, sleeve, or outer wrapper, but also provide desirable functionality in terms of providing enhanced resistance to premature activation via a higher dispensing threshold prior to the point of use.

Another means of reducing pre-mature bursting is the use of a secondary crimping device that "clamps" the frangible seal and prevents pre-mature bursting until the crimping device is removed. This crimping device could be a low cost injection molded part such as a flexible clip or paper clip-like structure. The crimping device should have enough biasing force to keep the pouch in a generally flat condition adjacent the frangible seal or any region where protection from bursting is needed. A third approach is to have a pouch that is only partially filled but when folded on the reservoir has the right fill volume that allows the pouch to be burst when squeezing. When flat, the pouch can be squeezed and not burst since the fluid can flow to other portions of the pouch before the two sides of the pouch touch each other and bottom-out when squeezing.

Back Panel

The back panel 26 may aid in keeping the mitt 10 on the hand or finger(s) of the user. The back panel 26 may further serve to enclose the hand or finger(s) of the user, and may even serve additional functions such as removing a product applied to a surface via the front panel 24. The back panel 26 may be constructed of materials such as one or more films, nonwovens, scrims, papers and/or the like.

After the product has been dispensed and dispersed onto the target surface, for example, it is sometimes desirable to absorb and remove excess product, contaminates and/or particles from the target surface while minimizing filming, streaking and/or residuals. Accordingly, the back panel 26 of the mitt 10 can be made from a material that is substantially absorbent for the product of interest. For example, the back panel 26 may be constructed of absorbent fibers that swell when exposed to the product of interest (e.g., liquids such as water, oils, etc.). Examples of absorbent fibers include man-made fibers derived from cellulose (e.g., rayon, cellulose acetate, cellulose triacetate) and natural cellulose fibers (e.g., from trees). Other examples of absorbent materials include particles and fibers made from superabsorbent polymers (e.g., crosslinked copolymers of acrylic acid) that can be incorporated into the back panel 26. Additionally, or in the alternative, the back panel 26 may be constructed of nonwovens, apertured films, absorbent or fibrous absorbent materials, super absorbent polymer fibers or powders, or laminates and/or combinations thereof. Absorbent nonwovens may be made by methods such as spunlace, spunbound, meltblown, carded, air-laid, and hydroentangled. In one embodiment, for example, the back panel 26 material preferably has sufficient capacity to absorb four or more times its own weight of a liquid product. For aqueous liquids, four plies of disposable kitchen paper towel such as BOUNTY®, a product of The Procter & Gamble Company, has been found suitable for use. This paper towel material typically has the capacity to absorb between about eight and about nine times its own weight in water and will naturally retain the liquid more so than a thermoplastic non-woven material, for example. The fibers in the absorbent paper towel material will absorb the liquid and will swell to some extent as the liquid is absorbed. If higher wet strength is desired, other structures, such as hydroentangled materials comprising cellulose, rayon and polyester may provide enhanced strength. One such set of materials are made by Dexter Corporation of Windsor Locks, Conn. and sold under the trade name Hydraspun®, can also be used. Further, absorbent foams such as those described in U.S. Pat. No. 5,571, 849 issued to DesMarais may also be suitable for use as the back panel 26. The back panel 26 preferably has sufficient absorbent capacity to absorb the quantity of liquid dispensed from the reservoir without oversaturation or substantial loss of web integrity. For example, the absorbent layer preferably has in the range of about two to about eight times, and more preferably in the range of about three to about five times, the absorbent capacity of the volume of the liquid within the reservoir 30. In one embodiment, if the reservoir 30 contained about 8 cc's of liquid product and the back panel 26 comprised a BOUNTY® paper towel that holds about eight times its weight in water, then to have two times the absorbent capacity a total of about 2 grams of the paper towel would be desired. Similarly, about 8 grams of the paper towel material would be required if an absorbent capacity of about eight times the capacity of the reservoir 30 cc's. The extra absorbency will further aid in achieving a streak-free shine because back panel 26 will be able to remove nearly all of the liquid on the target surface without leaving a film or streaks of cleaning solution. Further, as known in the art, certain materials may have a relatively higher capillary action to remove the liquid from the surface of the back panel 26 and may thus require less absorbent capacity versus the reservoir capacity, e.g., about two to about three times the capacity of the reservoir. In one embodiment, for example, a structure such as those described in U.S. Pat. No. 5,571,849 issued to Desmarais, which is incorporated by reference, can be used as the back panel 26, or may be used in the back panel 26. Further, due to evaporation, absorption into the target surface, and other effects, however, the back panel often is not expected to absorb the entire quantity of delivered fluid. Additional additives such as wet strength additives, dry strength additives, cationic treatments, cationic promoters, softeners and absorbency aids may be employed if desired.

As described above, one side of the applicator may be designed with a majority of non-absorbent fibers (termed "substantially non-absorbent") and the other side may be designed with a majority of absorbent fibers (termed "substantially absorbent"). In the context of the invention, these terms are relative to one another. Depending upon the specific application, the product to be spread, the environmental conditions, and the benefits sought, the amount of product that the substantially absorbent side absorbs and the amount of a product the substantially non-absorbent side absorbs will not be constant. Rather, the substantially absorbent side will have a relatively higher absorbent capacity than the substantially non-absorbent side for the particular product. The ratio of the absorbent capacity of the substantially absorbent side to the absorbent capacity of the substantially non-absorbent side is greater than one, preferably greater than two, and more preferably greater than four.

In some embodiments, the mitt 10 can have multiple layers on either the front panel 24 or the back panel 26 to provide additional absorbency and/or cleaning surfaces. Preferably additional layers can be heat sealed only to the perimeter and sealed in such a way that the layer is peelable. However, layers may be attached and removed by other methods such as perforations, peelable adhesives, and the like. The layers can be slightly offset at the cuff region (21), or additional material such as tabs may protrude from the layer, making it easier for the user to remove one layer at a time. Peelable heat seals may be accomplished by heat sealing the individual layers at a lower temperature or with less seal time such that a peelable seal occurs. These layers can also be made peelable by using a contamination layer or other methods known in the art. An example of how peelable layers can be used would be for a heavy-duty cleaning mitt where heavily soiled surfaces are cleaned. On heavily soiled surfaces, the mitt surfaces 24 and 26 may become soiled to an undesirable level before all the fluid in the reservoir is used. To overcome this, an extra layer(s) of a polypropylene non-woven could be used on the front panel 24 allowing the user to peel off a dirty layer as needed to deliver a fresh new clean wet scrubbing layer. The porous polypropylene nonwoven will allow the cleaning fluid to travel through multiple layers while the dirt tends to stay only on the outer surface in contact with the surface being cleaned. This would allow the user to continue using the mitt over more surfaces if additional cleaning fluid is still available in the reservoir. Similarly, the absorbent back panel 26 could have multiple layers of an absorbent paper towel such as Bounty® made by Procter & Gamble. The absorbent backside layers could be coated with a thin coating of a barrier material such as Polyethylene that prevents fluid from saturating other layers except for the outer layer that is being used. When this outer layer becomes too wet or too dirty, the outer layer can be removed exposing a new clean layer.

To protect the wearer's hand from contact with liquids absorbed by the back panel 26, it may be desirable for some applications to include an optional additional fluid impervious barrier layer 27, the interior of which defines the back inner surface 34 that faces the wearer's hand during use. The optional additional fluid impervious barrier layer 27 may be similar in construction and materials as the barrier layer 25 described above. Particularly when a second barrier layer 27 is employed, it may be desirable for some applications to include an optional secondary fluid reservoir 35 to deliver a second, possibly of diverse composition, liquid product to the target surface. One example of such a scenario would be the use of water or a neutralizing agent in the secondary reservoir after the liquid in the primary reservoir has been utilized.

The front inner surface 32 and the back inner surface 34 may be optionally provided with friction-enhancing elements or coatings 28 to prevent slippage between the wearer's hand and the back inner surface. The friction-enhancing elements or coating 28 on the back inner surface, for example, may reduce the likelihood of the mitt rolling or rotating of the mitt upon the hand when the frictional forces between the back panel and the increasingly dry target surface escalate. Suitable materials that can be used as the friction-enhancing elements include rubber, thermoplastic elastomers (e.g., KRATON® produced by Shell Chemical Company), polyolefins with ethylene vinyl acetate or alpha-olefin copolymers, and polyolefin plastomers (e.g., Affinity® produced by Dow Chemical of Midland, Mich. and Exact® polyolefin plastomers produced by Exxon Chemical of Houston, Tex.). In one embodiment, for example, a hot melt coating produced by Ato Findlay of Wauwatosa, Wis. under the designation of product 195–338, can be slot coated onto the back inner surface 34. The coating can also be applied in a foamed state such as by the addition of physical blowing agents such as nitrogen and/or carbon dioxide. In addition to slot coating, suitable materials can be applied (foamed or unfoamed) in one or more of an array of lines, spirals, spots and/or any other patterned network, by spraying, gravure printing, or by adhesively or otherwise securing separate pre-formed elements.

In one embodiment, an inner surface, such as the back inner surface 34, may have a friction-enhancing element that has a higher coefficient of friction between its surface and the wearer's hand than the coefficient of friction between the outer surface, such as the back outer surface 33, and the target surface. In a glass cleaning embodiment, for example, the back panel 26 may be an absorbent paper towel material used to absorb a liquid product and buff the target surface dry after it is cleaned. The coefficient of friction between a glass surface with Cinch® window cleaner, a product of The Procter & Gamble Company located in Cincinnati, Ohio, and a paper towel may be in the range from about 0.7 to about 0.9 as measured according to ASTM D1894-90, entitled "Standard Test Method for Static and Kinetic Coefficients of Friction of Plastic Film and Sheeting." A friction-enhancing element in this embodiment would preferably be a coating that delivers a higher coefficient of friction between a wearer's hand and the back inner surface 34 of the mitt 10 such that the mitt 10 does not slip or rotate on the hand when buffing the target surface with the back panel 26.

Figure 25:
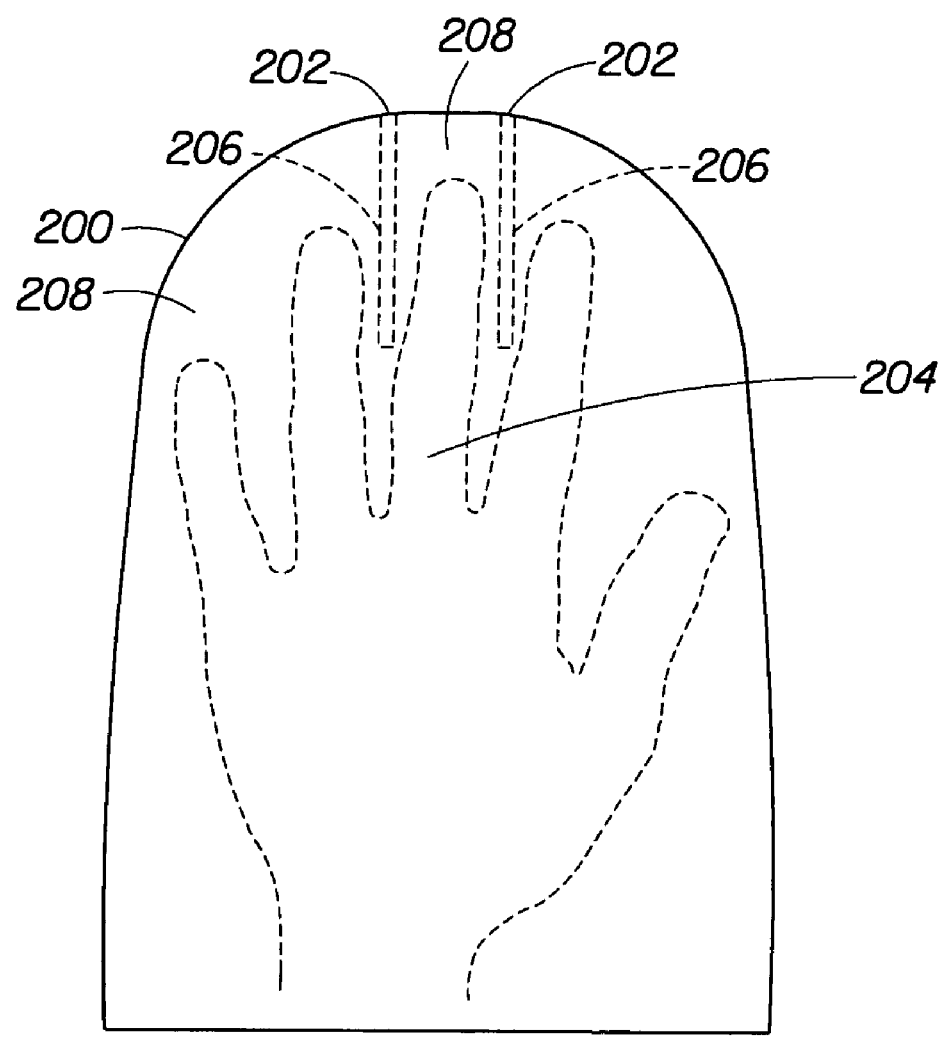
FIG. 25 is a plan view of a mitt with seal line elements to aid keeping the mitt from shifting on the hand during use.
Figure 26:
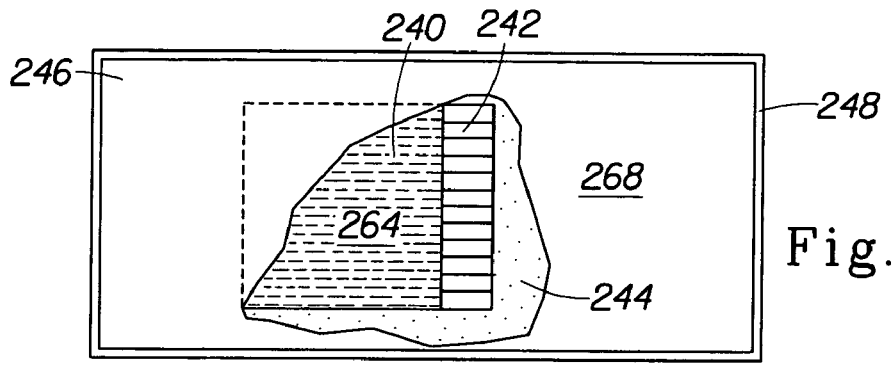
FIG. 26 is a top view of a temperature changing element of one embodiment of the present invention.
Figure 27:
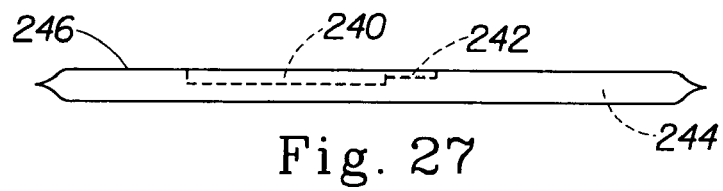
FIG. 27 is a side view of a temperature changing element of one embodiment of the present invention.

Alternatively, as shown in FIG. 25, the mitt 10 can be bonded or combined with one or more seals to provide a full or partial pocket for one or more fingers of the user. The line seal 206 may prevent the mitt 10 from rotating on the hand of the user, and may further provide a means for gripping the mitt when the fingers are pressed together during use. The line seal 206 may form a partial pocket 208 for one or more fingers and may, for example, extend from the outside perimeter 200 at the top 202 of mitt 10 towards the cavity 204. In one embodiment, the line seal may extend a distance from about 2 inches to about 4 inches from the outside perimeter 200 of the mitt 10.

In use, a wearer of the mitt 10 inserts a hand into the hollow interior through the provided opening at the cuff region 21 wherein the back panel contacts the back of the wearer's hand and the front panel contacts the wearer's palm. As the construction of the mitt 10 is more generic than a glove with defined anatomically-conforming geometry, the mitt may be used for either hand and/or may be appropriately sized to fit the foot of a wearer or any other bodily extremity.

If desired, at the end of its use, the mitt can be everted by making a fist with the mitt-hand, pulling the structure over the fist from the cuff region 21 of the mitt 10. Thus the layers are transposed, and the inner surface of the front panel and the inner surface of the back panel become the outer surfaces of the now waste article. More simply stated, the mitt is turned inside out after its use and then thrown away. That is, the wearer makes a fist, and with his or her other hand, grasps a point on the cuff region and carefully pulls the fisted hand toward the open mouth of the mitt, until the entire end of the mitt is pulled through the cuff.

In one embodiment, the mitt 10 may be a differentially extensible hand article wherein at least a portion of the mitt extends and/or contracts about a wearer's hand and/or wrist without the use of traditional elastic such as natural or synthetic rubber. By the term "differentially extensible" or "differential extensibility" it is meant herein to describe that quality of extensibility wherein portions of the glove extend or contract independently of other portions in response to varying hand sizes and motions. Preferably, this differential extensibility allows a range of hand sizes to fit comfortably within the mitt. The mitt 10 may be provided with differential extensibility by utilizing a structural elastic-like film web such as those described in commonly-assigned U.S. Pat. No. 5,518,801, issued to Chappell, et al. on May 21, 1996, and U.S. Pat. No. 5,650,214, issued Jul. 22, 1997 in the names of Anderson et al., and U.S. patent application Ser. No. 08/635,220, entitled "Fitted Glove", the disclosures of each of which are hereby incorporated herein by reference. Alternatively, differential extensibility to fit varying sized hands comfortably can be accomplished by various elastic-like materials, composite materials that produce elastic-like characteristics and/or processes to make a material(s) more elastic-like. Examples of suitable elastic-like materials include low density polyolefins such as low density polyethylene, linear low density polyethylene, ultra low density ethylene copolymers (copolymerized with alpha-olefins such as butene-1, octene-1, hexene-1, etc.), Affinity® polyolefin plastomers produces by Dow Chemical Company of Midland, Mich. and Exact® polyolefin plastomers produced by Exxon Chemical of Houston, Tex. As used herein, the term "elastic-like" describes the behavior of web materials such as web materials which, when subjected to an applied elongation, extend in the direction of applied elongation. Also, when the applied elongation is released the web materials return, to a substantial degree, to their untensioned condition. The term "web" as used herein refers to a sheet-like material comprising a single layer of material or a laminate of two or more layers.

The use of differentially extensible materials and suitable manufacturing processes, such as those described below, may be utilized to create a corrugation or pleating of at least one surface of the applicator, also characterized as a plurality of "rugosities". FIG. 11 illustrates a cross-sectional view of an applicator similar to that of FIGS. 1 and 2, but depicting the use of rugosities on an applicator surface. The applicator 10 of FIG. 1 is structurally similar to the cross-sectional view of FIG. 2, and therefore many of the reference numerals are omitted in the interest of clarity. However, as shown in FIG. 11, the fluid-impervious barrier layer 25 is provided with differentially extensible properties, preferably in accordance with the aforementioned commonly-assigned U.S. patents to Chappell, et al., and Anderson, et al., and therefore provides a plurality of rugosities 50 to the front outer surface 31 via the pleating or corrugation of the tissue layer 37 and front panel 24. The size and frequency of the corrugations and/or pleats can be controlled, in one embodiment, by the bonding pattern and the amount of stretch applied. The greater the stretch applied to the barrier layer 25, the greater the amount of material will be available for the corrugations and/or the pleats. In addition, the bonding pattern between a stretched material and the unstretched tissue layer 37 and/or the front panel 24 can be used to control the frequency and location of the corrugations and/or pleats. Such rugosities would be, in the embodiment of FIG. 11, parallel pleats or corrugations that extend in the direction into and out of the page. Without wishing to be bound by theory, it is believed that such corrugations or rugosities enhance the scrubbing and dispersing performance of the front outer surface and may provide built-in void space for trapping dust, dirt, and particulate material. The direction of the corrugations, for example, can be used to control liquid flow and have proven to be effective in preventing liquid from running off the mitt in cases of overdosing by the user. Liquid will naturally follow the direction of the corrugations preferentially versus spreading across the corrugations. Thus corrugations that run along the length of the mitt will tend to move the liquid along the length of the mitt. This also prevents the liquid from running off the narrower width side when the mitt is held at an angle. The corrugations can also act as baffles such that liquid sitting on the surface will not spread across the baffles but instead will tend to travel in the direction of the baffles. Consequently the pattern, direction, and frequency of these corrugations can be controlled and designed to spread the liquid as desired. The texture of the extensible film also provides a better aesthetic feel to the hand and provides an elastic fit desired in a glove or mitt.

FIG. 12 is a perspective view of one suitable material and structural configuration for a barrier layer 25 in accordance with FIG. 11, such material being consistent with the materials disclosed and claimed in the aforementioned commonly-assigned U.S. patents to Chappell, et al., and Anderson, et al. Such materials typically provide for extensibility, and (if applicable) elastic recovery, in a predominant direction illustrated via the use of the arrow labeled "D" in FIG. 12. When such a directional material is utilized in the construction of an applicator consistent with FIG. 11, the direction "b" would be oriented perpendicular to the direction in which it is desired for the rugosities to extend. Said differently, for the embodiment of FIG. 11 the direction "D" for the barrier layer 25 is left to right across FIG. 11 while the rugosities 50 extend in the direction into and out of the page. The embossed pattern of the film further provides better aesthetics and hand feel by allowing more air to circulate around a wearer's hand and thus deliver a cooling effect that is not available with a flat film.

The method to obtain rugosities described above results from an extensible web that is stretched, bonded to an unstretched web (either the front panel 24 or a laminate of front panel 24 and tissue layer 37) and allowed to relax to create rugosities. Another way of making either the first or second side of the applicator having more surface area without increasing the footprint of the applicator is to texture or reform the web into pleats, ribs, corrugations, and the like in any method known in the art. Such methods include but are not limited to embossing, ring-rolling, and incremental straining. The web can be a single layer of material or a lamination of several layers of material. For example, the front panel 24, such as a polypropylene nonwoven, and the tissue layer 37, such as a 1-ply of Bounty® paper towel, can be textured and made extensible in accordance to the approach described in the aforementioned Chappel patent. These layers can be bonded by, but not limited to, any of the following bonding methods: thermal bonding, sonic bonding, adhesive bonding (using any of the number of adhesives including but not limited to spray adhesives, hot melt adhesives, latex-based adhesives, water-based adhesives, and the like), and directly applying nonwoven fibers onto a substrate. In a preferred embodiment, the materials are adhesively bonded with a hot melt adhesive. One such adhesive is H2031, a product Ato Findlay of Wauwatosa, Wis. While not wanting to being bound by theory, it is believed that the thermoplastic elastomer properties of the adhesive aid in allowing the materials to deform to the desired shape and aid in setting the materials into the desired shape thus allowing thicker pleats and pleats more resistant to compressive forces.

To facilitate spreading or dispersal of the substance upon the target surface, particularly to counteract the tendency of the substance to remain in a localized distribution pattern given the localized orientation upon the deformable substance, it is presently preferred to utilize substances which are tailored so as to be wettable-on the target surface. Other factors which may aid in dispersion or distribution of the substance upon the target surface include the use of substances which exhibit a shear-thinning behavior, as well as mechanical spreading action provided by the user of the composite sheet material to impart a lateral mechanical motion after activation but prior to removal of the deformable material from the target surface. Such lateral mechanical action may also provide additional interaction with the substance such as for shear-thinning substances and may provide additional benefits such as lathering, foam generation, scrubbing/abrasive action, etc.

Successful dispersal occurs when a portion of the deposited or dispensed product subsequently coats a portion of the target surface where the substance was not originally deposited. Upon removal of the sheet material from the target surface, at least some of the substance remains located on the target surface, preferably in a substantially-uniform fashion.

The mitts of the present invention may be packaged in any suitable fashion. However, one method of packaging the mitts involves tri-folding them in a C-folded configuration, then stacking a plurality of folded mitts within an outer carton or wrapper. It is believed that the "cushioning" effect of the superposed folded portions of the mitts provides additional protection against premature rupture of the fluid reservoirs.

The mitts of the present invention may also allow users to clean without the usual concerns associated with conventional spray and wipe products. One such concern relates to the potential for irritation and/or inhalation of volatile chemicals. Most spray or aerosol cleaners include one or more volatile organic solvents, or propellants, which can cause irritation to the nose or skin. The architecture of the product form of the present invention may reduce or eliminate this problem. Lack of spraying also means greater efficiency in the use of the product, and avoidance of product reaching surfaces, such as wood or clear plastic panels, that are adjacent to or nearby a target surface and may be sensitive to a particular product composition such as a product including organic solvents. Lack of spraying may further reduce or eliminate streaks due to a sprayed product not being properly buffed. In particular, the mitts can eliminate or reduce performance and surface safety issues that may result from product runoff. Users may also benefit from not having to store or carry multiple products just to undertake a particular cleaning task. Additionally, judicious selection of substrate raw materials for the mitts can maximize the cleaning benefit. As such, the user is prevented or discouraged from using inappropriate combinations of substrate and cleaning composition for a particular cleaning task. Finally, by combining the product form and cleaning composition in one, the user saves time.

The mitts of the present invention have multiple possible methods of use. In one embodiment, the mitts are folded so as to protect the product reservoir from pressure. Users may conveniently remove the mitts from a container, unfold the mitt and fit one of their hands through the mitt aperture. The reservoir pouch can be actuated to release the product. This can be achieved by any suitable method such as pressing on the reservoir pouch with one or more fingers, with the palm of the free hand, or by pressing the pouch against a solid surface. The amount dosed can be controlled by instructing the user to press the reservoir pouch so as to release an amount of fluid consistent with parameters that are either printed on the instructions for use, or written or graphically illustrated directly on the front panel 24 side of the mitt. In a particular embodiment, instructions for use call for releasing fluid so as to wick an area that is demarcated around the orifice from which the fluid is drawn. The area to be wicked can be shown by means of any graphical representation or in words. In a preferred embodiment, the area to be wicked is shown via a circle or other geometric figure. The size of the geometric figure can reflect the optimum composition volume for the task at hand, and will be a function of the substrate raw material, wicking ability and basis weight. In most cases, the geometric figure may be a circle having a diameter from about 1 centimeter to about 15 centimeters, more preferably from about 2 centimeters to about 8 centimeters. Those skilled in the art will recognize that the mitts can be designed so that liquid preferentially wicks in one direction versus another direction. In such instances, for example, the graphical demarcation on the mitt can preferably consist of one or more non-circular geometric figures.

In the event that mitts are used without the benefit of the attached dosing reservoir, the two-sided mitt can be used together with a conventional spray bottle. While this is not a preferred mode of use, some of the benefits stemming from the choice of absorbent and non-absorbent substrates are still retained. Accordingly, the methods for use will be similar to those described above, substituting the preferred dosing mechanism from the reservoir with an equivalent or slightly larger volume e.g., 1.0 to 1.5 times of cleaning composition delivered from the spray bottle.

The compositions of the present invention can contain several adjuvants such as perfume and dye. Use of dye may be especially advantageous when the mitt panels are made of a light color because it allows the user to see the product as it is dispensed and to dispense an appropriate amount of cleaning composition for a specific cleaning task. Dyes that are colored and become colorless as result of exposure to air can also be used to visually help users dose while limiting the potential for staining. In some cases, no dye is used, particularly if the mitts are colored. In one embodiment, for example, the tissue paper layer 37 in the front panel 24 can be colored a dark color such as blue and may not be visible until fluid is dispensed. To aid in seeing the fluid when it is initially dispersed the layers can be bonded to ensure direct contact between the two layers. These layers can be bonded by but not limited to any of the following bonding methods: thermal bonding, sonic bonding, adhesive bonding (using any of the number of adhesives including but not limited to spray adhesives, hot melt adhesives, latex-based adhesives, water-based adhesives, and the like), and directly applying nonwoven fibers onto a substrate. In a particular embodiment, the materials can be thermally bonded together in a pattern that directs the user in understanding the amount of fluid to be dispensed.

Heating/Cooling

The mitt 10 of the present invention may also include a heating and/or cooling element such as shown in FIGS. 26–45. The heating/cooling element may include an exothermic or endothermic system that provides a heating or cooling effect, respectively. The systems may include heating/cooling by, but not limited to, an anhydrous reactions, heats of solution, oxidation reactions, crystallization, corroding alloys, zeolite-liquid systems and/or heat of neutralization.

One embodiment of a heating/cooling element may include a solid-liquid or liquid-liquid heating/cooling system, such as an anhydrous reaction system, a heat of solution system, a zeolite system, an electrochemical system, etc. A solid-liquid heating/cooling system includes any system in which an exothermic or endothermic change occurs during the combination or mixing of two or more components where at least one component is substantially liquid in nature (e.g., water) and at least one component is substantially solid in nature (e.g., anhydrous salts). A liquid-liquid heating/cooling system includes any system in which an exothermic or endothermic change occurs during the combination or mixing of two or more components where two or more of the components of the system are in a substantially liquid form.

In one embodiment, the heating/cooling element may comprise a self-enclosed heating/cooling system. The heating/cooling system may include a substantially moisture impermeable outer layer 246, which may be at least partially flexible or deformable. For example, the moisture impermeable outer layer 246 may be a metallized film, foil laminate film, MYLAR®, a formed metal sheet or other water or moisture impermeable materials. The moisture impermeable outer layer 246 may also include a material having optimal thermal conductive parameters such as a metallized foil that permits greater thermal diffusivity and/or conductivity. The heating/cooling system may include at least two components of a solid-liquid or a liquid-liquid heating system housed within the moisture impermeable outer layer 246. The heating/cooling system, for example, may include a rupturable pouch 240 that contain(s) a first component of the heating/cooling system. The rupturable pouch may be formed from a metallized film or other material having a low moisture vapor transmission rate (MVTR) in order to minimize losses of the liquid component(s) contained within the pouch or entry of liquid or moisture into the pouch that may contaminate the solid component(s) contained within the pouch prior to activation of the heating/cooling element. The rupturable pouch 240 may include a frangible seal 242 to allow a user to rupture the seal by squeezing or otherwise applying pressure to the heating/cooling element and to release the first component from the rupturable pouch.

Figure 28:
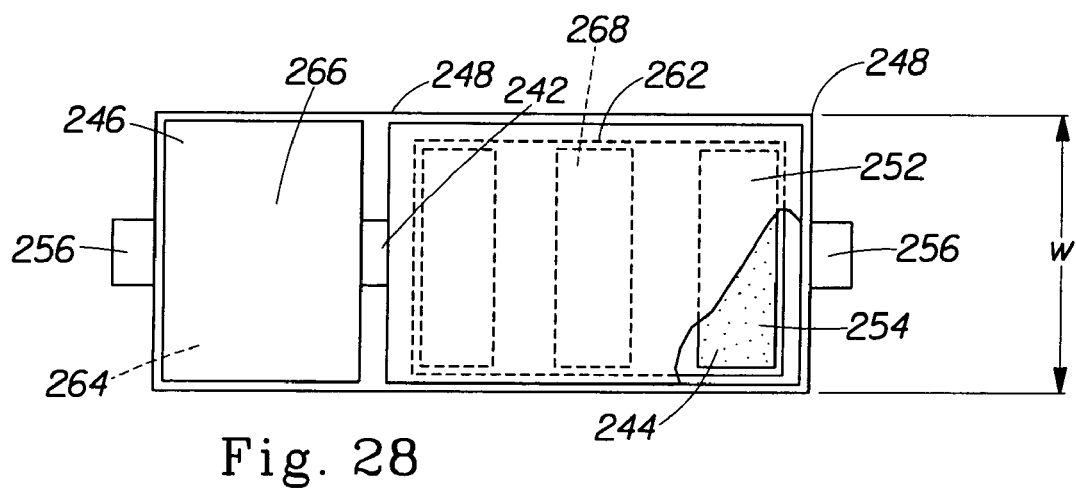
FIG. 28 is a top view of a temperature changing element of one embodiment of the present invention.
Figure 29:
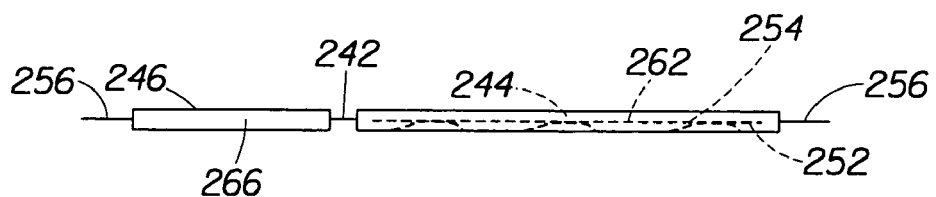
FIG. 29 is a side view of a temperature changing element of one embodiment of the present invention.
Figure 30:
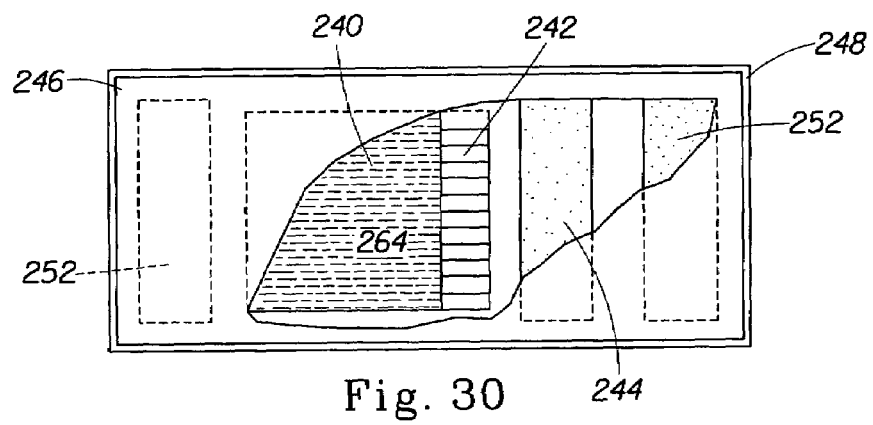
FIG. 30 is a top view of a temperature changing element of one embodiment of the present invention.
Figure 31:
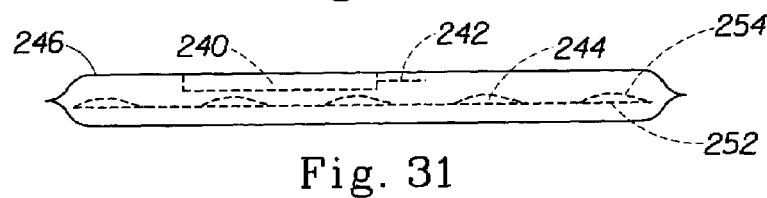
FIG. 31 is a side view of a temperature changing element of one embodiment of the present invention.

Alternatively, the rupturable pouch may include weakened portions in the pouch material such as scores, perforations and the like, pull tabs, may include metal shavings or other items that may puncture the rupturable pouch upon the application of pressure, or may include any other means of rupturing a pouch known in the art. The heating/cooling element may also include a second component 244 of the heating/cooling system. The second component 244 may, for example, be contained loosely within the water impermeable outer layer 246 or, if a solid component, be contained within one or more porous, liquid permeable compartments 254 such as shown in FIGS. 28–31, 36, and 37. The liquid permeable compartments 254 may be formed by a porous material such as a porous cellulosic material (e.g., wet-laid or air-laid), a porous polymeric film such as a polyethylene film which has been needle-punched or vacuumed-formed, a polymeric mesh material such as a woven nylon mesh material such as Nitex™ supplied by Sefar America Inc., Depew, N.Y., etc. Preferably, the pore size of the porous material is smaller than the particles of the solid second component(s) 244. The heating/cooling element may include one or more compartments that house the solid-second component(s) 244 located-within the moisture impermeable outer layer 246. The solid second component(s) 244 may be packed within the one or more compartments of the heating/cooling element at a component volume in the range from about 60% to about 95% of the available compartment space in order to keep the solid second components in close proximity to each other. Tightly packing the solid second component(s) in one or more compartments can prevent the solid second component(s) from shifting in the heating/cooling element and can also prevent "saddle-bagging" of a flexible heating/cooling element. Further, keeping the solid second component(s) in a packed state within one or more compartments can promote even heating/cooling in the heating/cooling element via a defined and repeatable amount of component per unit volume, can reduce the surface area exposure and thereby reduce the rapid surface convective losses of the heating/cooling element, and can better meter the rate that the heat produced or consumed by the exothermic or endothermic system due to forced conduction through the packed bed. In some embodiments, the pouch may further distribute any liquid component(s) across the surface of the solid second component(s) 244 through wicking and/or capillary action. Additionally, or in the alternative, a liquid distribution layer such as the layer 262 may be provided in proximity to the solid second component(s) 244 of the solid-liquid system to distribute any liquid component(s) across the surface of the solid second component(s) 244 through wicking and/or capillary action such as shown in FIGS. 28 and 29. This may be especially useful in embodiments where the solid second component(s) are contained in a porous sheet that will not readily wick the aqueous solution across its surface or in embodiments where the solid second components are contained loosely within the water impermeable outer layer 246. The liquid distribution layer, for example, may include a cellulosic material such as paper towel layers such as Bounty® sold by the Procter & Gamble Company of Cincinnati, Ohio, capillary channel fibers, hydrophilic woven and non-woven materials, apertured formed films or any other distribution materials known in the art. Further, absorbent, wicking or capillary action materials such as cellulosic materials, superabsorbent polymers and/or other hydroscopic materials may be interspersed within the particles of the solid second component(s) in order to allow for a more even dispersion of the liquid component(s) throughout the solid second component(s) allowing for a more and full usage of the component(s). This may be especially useful in embodiments where the solid second component(s) are mixed with additives such as encapsulated phase change materials such as Thermasorb Series® available from Frisby Technologies, Winston-Salem, N.C. or polyethylene powders that are somewhat hydrophobic. Further, the addition of cellulosic materials may be beneficial in embodiments where another additive such as guar or xanthan gum is added to one or more of the component(s) to help tailor the temperature profile but may also affect the rate at which the reaction occurs due to a viscosity change in an aqueous solution liquid component. Further, the addition of cellulosic materials may also be beneficial where reactive materials such as magnesium sulfate or calcium chloride, in a packed form, may form a thin crystal sheet across the areas where the water first comes in contact with them. This may impede the progress of a liquid component to areas of the packed bed that are below the crystal surface.

Another embodiment of a heating/cooling element includes a solid-liquid and/or liquid-liquid heating/cooling system such as shown in FIGS. 28, 29, 32–35 and 38–41 in which multiple components of the system can be housed in adjacent chambers separated by a rupturable barrier 242 such as a frangible seal or other rupturable barrier such as described above. The heating/cooling element, for example, may include a water impermeable outer layer 246 formed into a pouch having two or more chambers that separately house at least a first component and a second component of the system prior to activation. Upon compression of one or more chambers of the heating/cooling element, the rupturable barrier 242 may burst and allow the first and second component(s) to come into contact with each other.

Figures 46, 47:
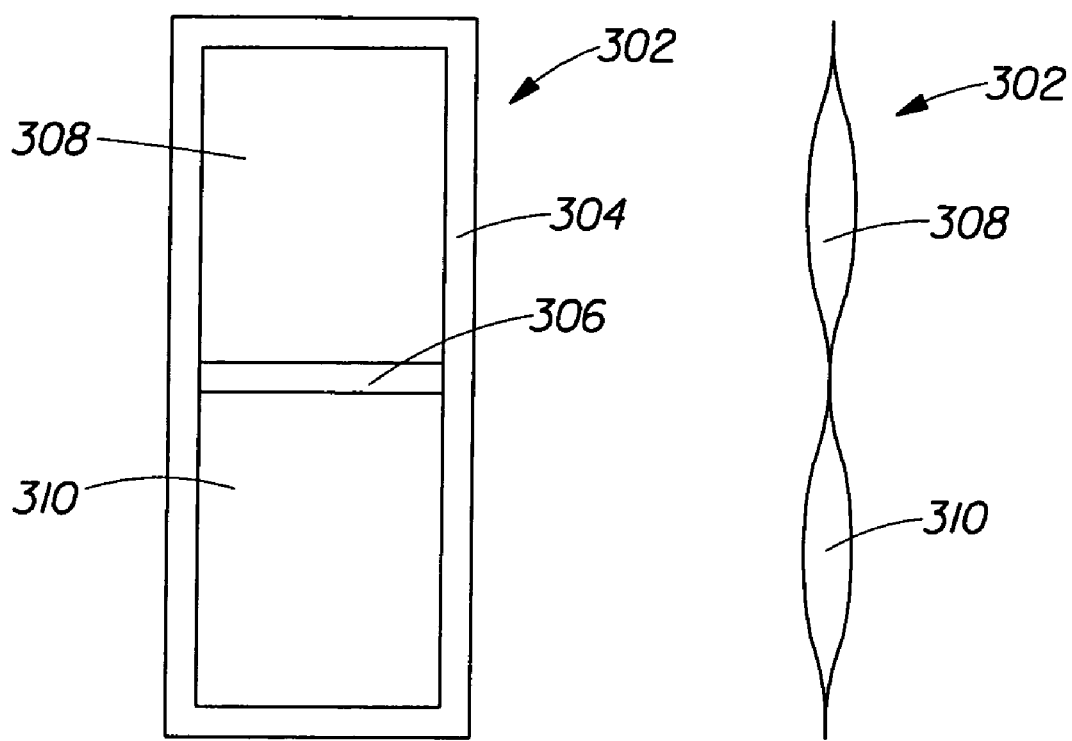
FIG. 46 is a plan view of one embodiment of a rupturable two component heating or cooling reservoir suitable for use in accordance with the present invention.
FIG. 47 is an elevational view of the rupturable heating or cooling reservoir of FIG. 46.

In one embodiment such as shown in FIG. 46, the heating element may include a pouch 302 having a permanent or strong seal 304 extending about at least a portion of the periphery of the pouch 302 (e.g., the pouch may include two or more pieces of film sealed around four sides, may include a film folded over itself and sealed around three sides, etc.). The pouch may include multiple chambers 308 and 310 that are separated by one or more frangible seals 306. In the embodiment shown in FIGS. 40 and 41, for example, the pouch may include a first chamber 268 and a second chamber 266 separated by a frangible seal 242. The first chamber 268 may contain a first component and the second chamber 266 may contain a second component. The first and second components may include a solid component (e.g., anhydrous salt, electrochemical alloys) and a liquid-component (e.g., water), a liquid component and a solid component or a liquid component and a second liquid component. Applying pressure to one or more of the chambers such as squeezing, pressing, kneading, etc. may rupture the frangible seal 242 and mix the components of the first and second chambers together to release or absorb energy from the environment.

Figure 32:
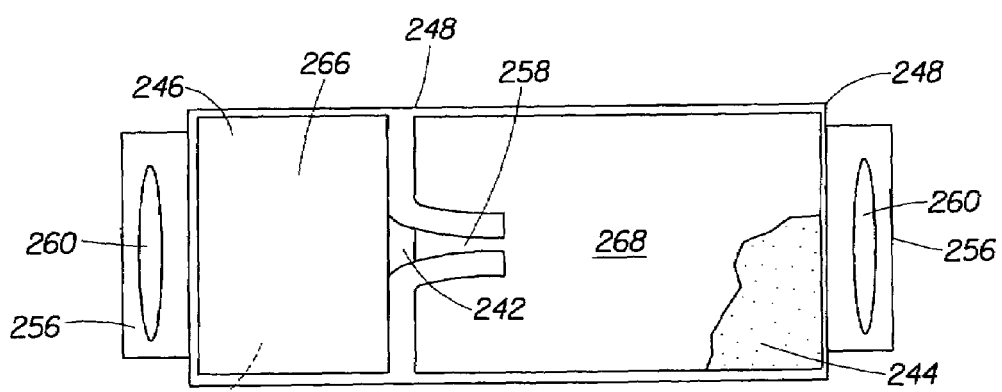
FIG. 32 is a top view of a temperature changing element of one embodiment of the present invention.
Figure 40:
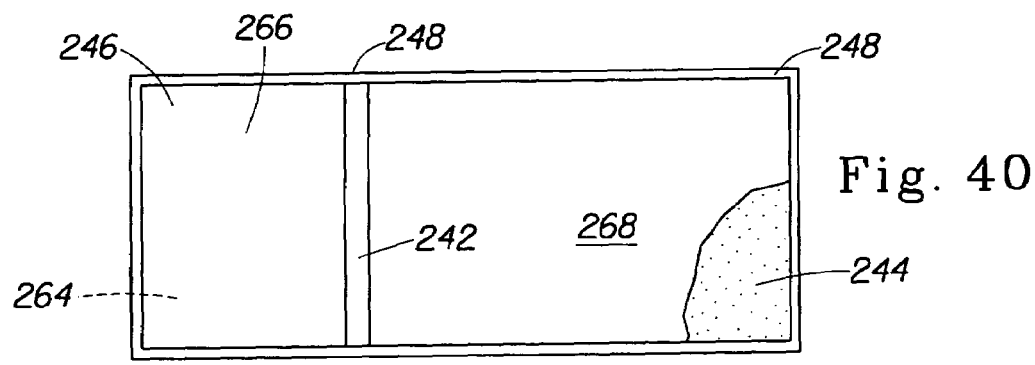
FIG. 40 is a top view of a temperature changing element of one embodiment of the present invention.
Figure 41:
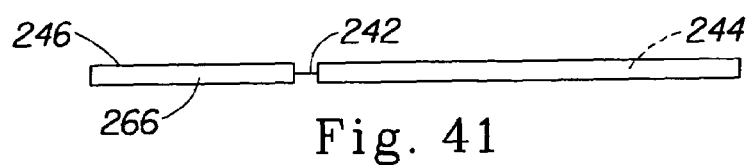
FIG. 41 is a side view of a temperature changing element of one embodiment of the present invention.

FIGS. 28, 29, 32, and 33, for example, show further embodiments of a heating/cooling element including a first component 264 housed in a first chamber 266 and a second component 244 housed in a second chamber 268 separated by a frangible seal 242. In these embodiments, a frangible seal 242 separates the first chamber 266 from the second chamber 268. The frangible seal 242 may extend a portion of the width W of the heating/cooling element such as shown in FIGS. 28, 29, 32 and 33 or may extend the entire width of the heating/cooling element between the first and the second chambers 266 and 268 such as shown in FIGS. 40 and 41. In one embodiment, the frangible seal may be designed narrowly such as shown in FIGS. 28, 32, and 34 to minimize the backflow of the first component 264 into the first chamber 266 after activation. Alternatively, or in addition, the heating/cooling element may also include a channel 258 such as shown in FIG. 32 that further restricts the backflow of the liquid component 264 into the first chamber 266 after activation. As shown in FIGS. 28, 29, 36 and 37, the heating/cooling element may also include a solid component housed in multiple compartments 252 and may be held in place by porous pouch 254. Alternatively, a solid component may be contained loosely within a chamber (e.g., the second component 244 shown in FIGS. 32–35 and 40–41 may be a solid component contained loosely within the second chamber 268. The heating/cooling element may further comprise one or more attachment tabs 256 for attaching the heating/cooling element to structure of the applicator, such as the mitt 10.

Figure 33:
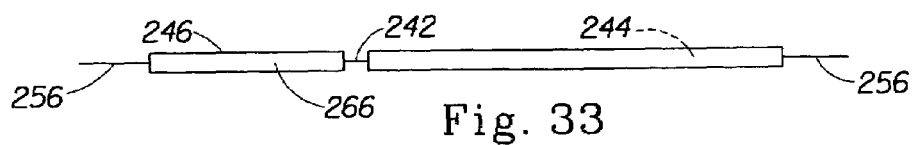
FIG. 33 is a side view of a temperature changing element of one embodiment of the present invention.
Figure 34:
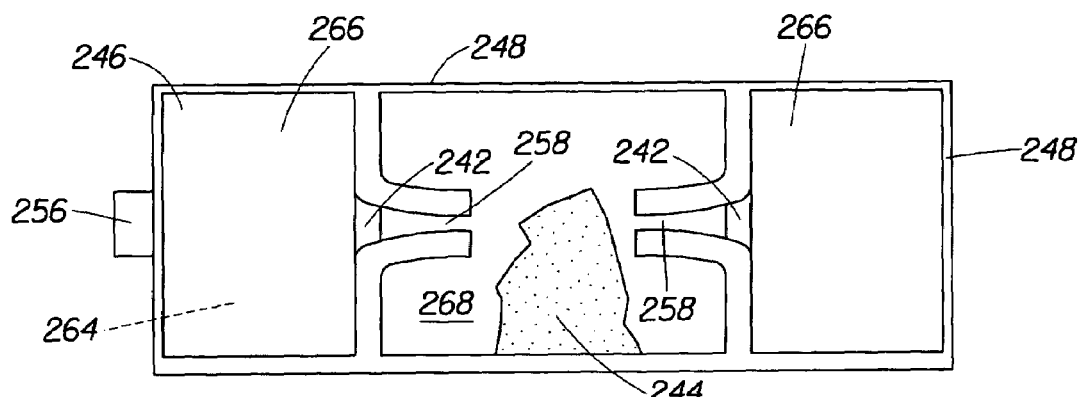
FIG. 34 is a top view of a temperature changing element of one embodiment of the present invention.

FIGS. 32 and 33 show yet another embodiment of a heating/cooling element that may be used in a solid-liquid or a liquid-liquid heating/cooling system. In this embodiment, a first liquid component can be housed in a first chamber 266 and a second liquid component or a solid component can be housed in a second chamber 268. The frangible seal 242 may extend across all or a portion of the width W of the heating cooling element, and channel 258 may extend into the second chamber 268 in order to prevent a backflow of the components into the first chamber 266 after activation.

Figure 35:
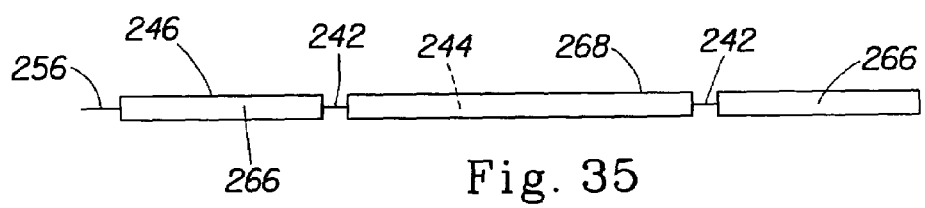
FIG. 35 is a side view of a temperature changing element of one embodiment of the present invention.

FIGS. 34 and 35 shows a temperature-changing element with at least two channels 258 that may be used for a substantially one-way flow-of-fluid components into the chamber 268. This allows for delivery of the fluid component to multiple locations within the chamber 268, which may be especially useful in larger packages or packages that may have varying orientations during activation such that wicking the liquid component(s) may become increasingly difficult.

Figure 36:
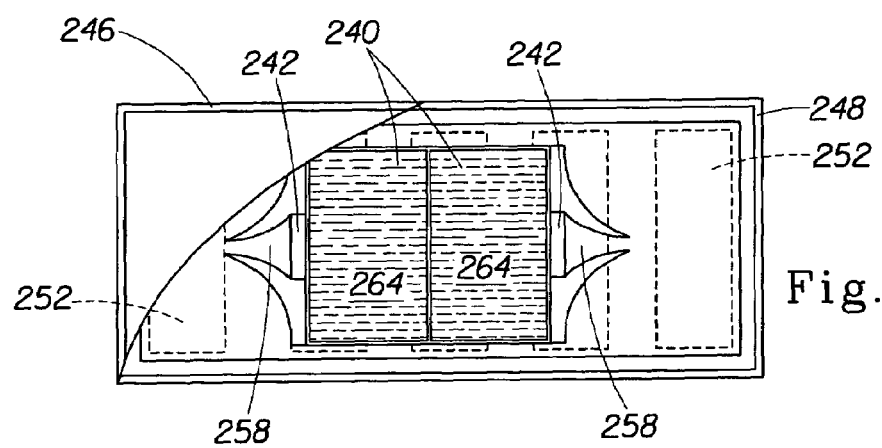
FIG. 36 is a top view of a temperature changing element of one embodiment of the present invention.
Figure 37:
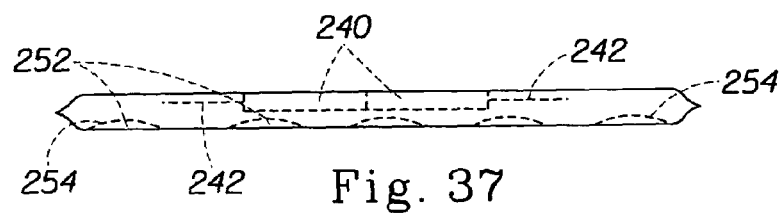
FIG. 37 is a side view of a temperature changing element of one embodiment of the present invention.

FIGS. 36 and 37 show a temperature-changing element in which a container 240 can be located above the reactant containing compartments 252. The figure also shows multiple exit channels 258 for the container 240. The compartments 252, for example, may be made of discrete packets in which one side is a porous material 254 and the other is a fluid impermeable; film such as polyethylene. In the specific embodiment the porous material 245 may be attached to the exterior package. This configuration disassociates the fluid bag from the heat generator and allows for the centralization of the fluid bag.

Figure 38:
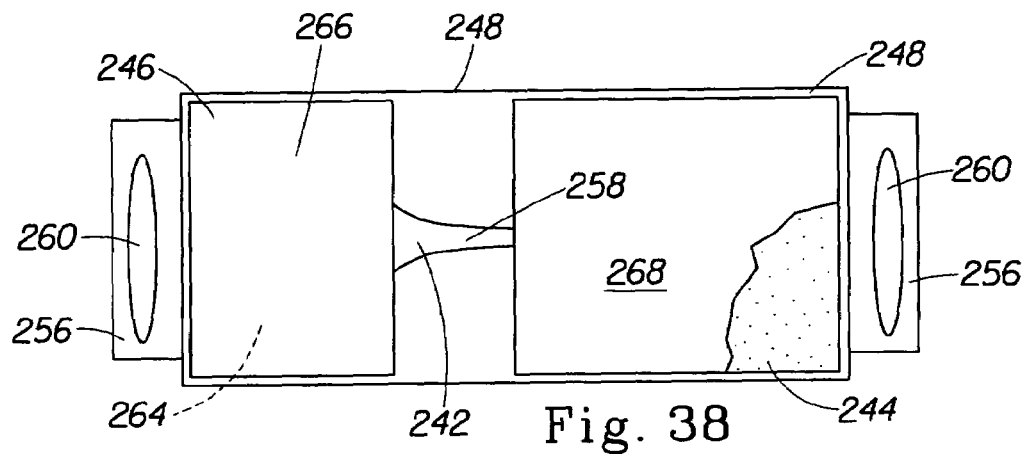
FIG. 38 is a top view of a temperature changing element of one embodiment of the present invention.
Figure 39:
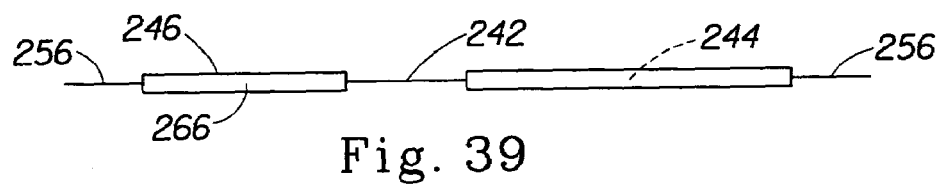
FIG. 39 is a side view of a temperature changing element of one embodiment of the present invention.

FIGS. 38 and 39 show an alternative embodiment of a temperature-changing element where the exit channel 258 is located within the seal area 248 to allow for the full use of the heating chamber. This may be beneficial for filling operations, for example, where channels extending into the chamber 268 may be an obstruction.

An exothermic solid-liquid heating system can include solid components such as calcium oxide, calcium carbonate, calcium sulfate, calcium chloride, cerous chloride, cesium hydroxide, sodium carbonate, ferric chloride, copper sulfate, magnesium sulfate, magnesium perchlorate, aluminum bromide, calcium aluminum hydride, aluminum chloride, sulfur trioxide (alpha form), zeolites (e.g., Carbsorb® 500 Series natural zeolite based on the mineral chabazite), mixtures thereof and other solid components of solid-liquid exothermic systems known in the art and combinations there of. An endothermic solid-liquid cooling system can include solid components such as sodium sulfate*$10H_2O$, sodium bicarbonate, potassium perchlorate, potassium sulfate, potassium chloride, potassium chromate, urea, vanillin, calcium nitrate, ammonium nitrate, ammonium dichromate, ammonium chloride and other solid components of endothermic systems known in the art. These solid components may be in an anhydrous form and may be used such as in a powder, granular or prilled condition. These compounds are generally hydroscopic and dissolve in or react with a liquid component, such as water, and give off or absorb heat.

Further exothermic solid-liquid systems can include an electrochemical reaction including solid components such as iron, magnesium, aluminum, or combinations thereof that react in the presence of salt and water. In these embodiments, the liquid component may include a salt-water solution or may include water if salt is included with the so id component(s) 244.

Yet another solid-liquid or liquid-liquid exothermic system includes systems that use of heat of neutralization to give off heat using acid and base components such as citric acid having a pH of about 3 or 4 and calcium hydroxide having a pH of 12 in approximately a 2 to 1 ratio, respectively.

Figure 42:
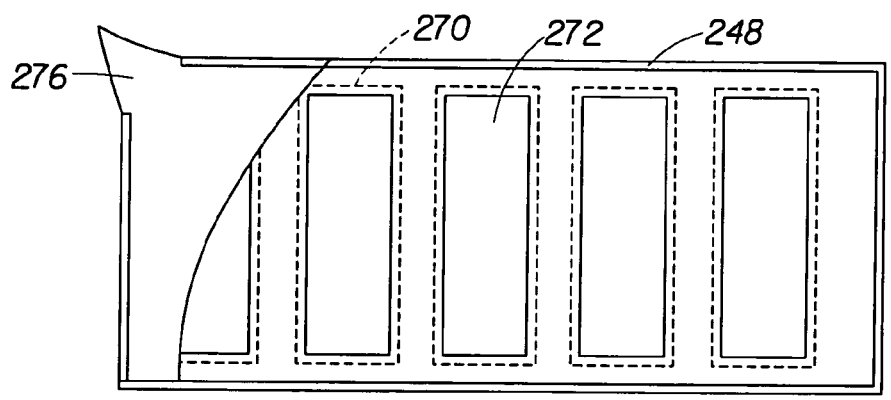
FIG. 42 is a top view of a temperature changing element of one embodiment of the present invention.
Figure 43:
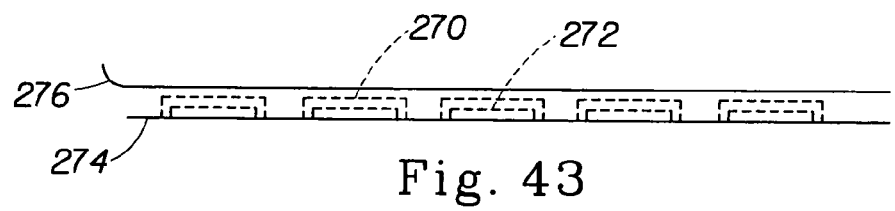
FIG. 43 is a side view of a temperature changing element of one embodiment of the present invention.

In another embodiment as shown in FIGS. 42 and 43, of a heating element may include a solid-gas heating system. A heating element may utilize the heat generated by supplying suitable amounts of water, salt, vermiculite, activated carbon and/or air to oxidize iron powder. For example, the heating element may include a porous bag 270, such as a fabric, an apertured film, etc., may allow oxygen-containing atmospheric gas to permeate into chamber that contains the solid component 272. The solid component 272, for example, may be filled with a uniform mixture of inorganic porous materials, iron powder, inorganic salts and water. The porous bag may further include a wetting agent and be capable of generating heat when exposed to the atmospheric air. This heating element may be formed by filling a mixture consisting of expanded inorganic porous materials such as vermiculite, iron powder, inorganic salts such as ammonium chloride and water containing a wetting agent into a porous fabric bag having air-permeability and sealing the bag. An example of solid-gas components is described in detail in U.S. Pat. No. 6,096,067 entitled "Disposable Thermal Body Pad" issued to The Procter and Gamble Company on Aug. 1, 2000, which is incorporated by reference.

FIGS. 42 and 43, for example, show a heating element including the solid component 272 of the solid/gas system. Thermal packs may further comprise a plurality of heat cells 272 spaced apart which provide controlled and sustained temperature and which reach their operating temperature range quickly. The heat cells can be embedded between the first 270 and the second 274 sides and fixedly attached within each thermal pack. The laminate structure may provide for oxygen permeability to each of the plurality of heat cells. Oxygen permeable layers such as known in the art, for example, may be located on the first side 270 of the laminate structure. The plurality of heat cells may have an oxygen activated, heat generating chemistry containing a mixture of powdered iron, powdered activated charcoal, vermiculite, water and salt. The second side of the structure may have an oxygen impermeable layer 274. The first side may further include an oxygen impermeable release layer 276 that can be removed to activate the heating system.

Figure 44:
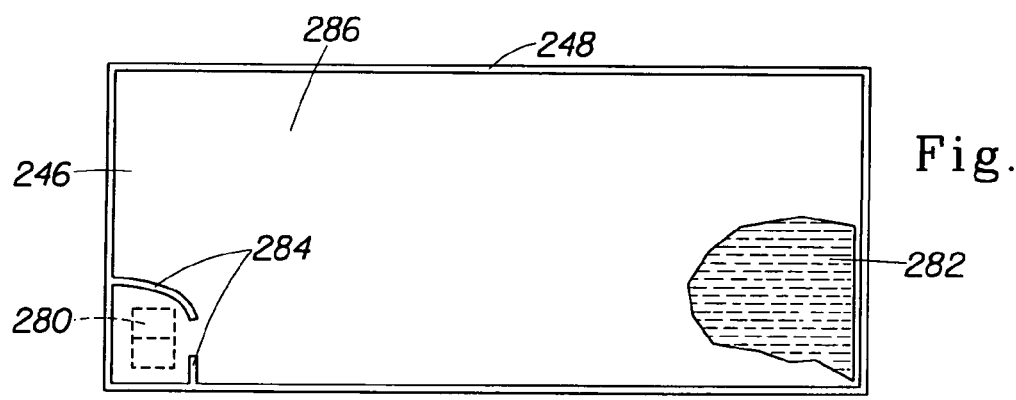
FIG. 44 is a top view of a temperature changing element of one embodiment of the present invention.
Figure 45:
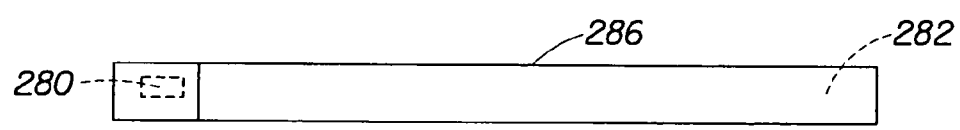
FIG. 45 is a side view of a temperature changing element of one embodiment of the present invention.

In another embodiment, FIGS. 44 and 45, of a heating element may include the use of aqueous salt solution(s) supercooled so that the heat packs can be carried in the supercooled condition and activated with internal release of heat when desired. Sodium acetate, sodium thiosulfate and calcium nitrate tetrahydrate are examples of suitable salts.

FIGS. 44 and 45, for example, show a heating element comprising of the supercooled salt 282 in a pouch 286 with activator 280. To activate crystallization of solution 282 one can use the scraping of two metal pieces, the addition of additional crystals that comprise the solution, or any other activation method known in the art. As shown in FIG. 44, the activator 280 may be located in a corner of the pouch with restraining seals 284 holding it in an easily identifiable location. The solution 282, for example, may be 1:1 ratio by weight of sodium acetate and water nixed at art elevated temperature and cooled to ambient temperature in a super saturated state prior to activation.

A mitt 10 of the present invention may include one or more heating/cooling elements such as the ones described above or other heating/cooling elements known in the art. For example, a liquid-liquid heating element is disclosed in International Published Application No. WO 99/41554 entitled "Liquid Heat Pack" filed on behalf of Sabin et al. and published on Aug. 19, 1999, which is incorporated by reference. The heating/cooling element may be used to heat a substrate of the mitt such as the front panel 24 and/or the back panel 26, or may be used to heat a product in a reservoir 30 and/or on or in another portion of the mitt 10 such as on or in the front panel 24 and/or the back panel 26. Thus, a heating/cooling element may be located adjacent to a reservoir 30, a distribution channel 44 of a reservoir 30, or a dispensing location of a reservoir 30. A heating/cooling element may also be located adjacent to one or more substrates of the mitt 10, for example between the front outer surface 31 and the front inner surface 32, between the back outer surface 33 and the back inner surface 34, or adjacent to one or more of the front outer surface 31, the front inner surface 32, the back outer surface 33 and the back inner surface 34.

In order to heat or cool a product within a reservoir 30, the heating/cooling element such as the heating/cooling pouch 302 may be located in intimate contact with the reservoir 30 such as shown in FIG. 51 to allow for efficient conductive heat transfer. This may be accomplished by the reservoir 30 and the heating/cooling pouch 302 in contact adjacent to each other when the mitt is combined, or the reservoir 30 and the heating/cooling pouch 302 may be adhered together with an adhesive or other bonding method known in the art. If it is desirable to activate both the reservoir 30 and the heating/cooling pouch 302 simultaneously, the reservoir 30 may be located directly over the portion of the heating/cooling pouch 302, such as one or more of the compartments 308 and 310 that contains a liquid component of the heating/cooling system. If it is desirable to activate the reservoir 30 and the heating/cooling pouch 302 sequentially or at different intervals, such as to heat/cool the product in the reservoir or to heat/cool a substrate of the mitt 10 before or after the product is dispensed from the reservoir 30, the fluid-containing reservoir can be located away from the activation portion of the heating/cooling pouch. For example, the compartment 266 of the heating/cooling element shown in FIGS. 28 and 29 may be offset laterally from the reservoir 30 such that the compartment 264 is offset from the reservoir 30 but the compartment 268 directly underlies the reservoir 30. In this embodiment, the heating/cooling element may be activated by pressing on the compartment 266 to rupture the frangible seal 242 and to expel the liquid first component 264 from the compartment 266 into the compartment 268 that contains a second component 244 of the heating/cooling system. The liquid first component 264 may react or combine into solution with the second component 244 in an exothermic or endothermic event. Then, when the product in the reservoir 30 has been heated/cooled, the reservoir 30 may be pressed to dispense the product.

In some embodiments, it may also be desirable that the product exit from the reservoir 30 onto the heating/cooling pouch 302. For example if the mass of the product released is small, the temperature of the product may change in temperature quickly as it is applied to a cooler surface. If the product is released onto the heating/cooling pouch 302, however, the heating/cooling pouch may be pressed against the target surface as the product is applied. Thus, the actual contact of the heating pouch 302 to the surface may provide an additional conductive heating/cooling effect.

The reservoir 30 and the heating/cooling pouch 302 may also be combined into a single pouch 326 as shown with a plan view in FIG. 48. The product reservoir portion 318 would have an exit location 316, which may include a frangible seal or other rupturable barrier 314 or other dispensing element known in the art such as a pull tab, a perforated tear strip, a tab that may be cut off, etc. The heating/cooling pouch 302 may also have a distribution channel region to control the product dispensing rate and direction such as shown in FIGS. 7, 9, 20 and 21. The outer perimeter of the pouch and the seal between the product reservoir portion 318 and one of the heat generating components 320 can be permanent seals 312. The exothermic or endothermic component portions of the pouch are shown as compartments 320 and 322 and are separated by a frangible seal or other rupturable barrier 324. To place the compartments of the pouch in position similar to those previously mentioned, the pouch can be folded between the product reservoir portion 318 of the pouch and the adjacent exothermic or endothermic component compartment 320 of the pouch 326 such as shown in FIG. 50. Thus, for simultaneous activation of the heating/cooling element and release of a product, compartment 320 can be filled with a liquid first component and compartment 322 can be filled with a liquid or solid second component. For sequentially activating the heating/cooling element and releasing the product from the product reservoir portion, compartment 320 can be filled with a solid or liquid second component and compartment 322 can be filled with a liquid first component. Sequentially activating the heating/cooling element and releasing the product from the reservoir portion can also be accomplished with the same orientation as previously mentioned for simultaneous activation, but where the seal strengths of the frangible seal 324 located beween the compartments 320 and 322 and the frangible seal 314 of the product reservoir portion 318 are different. In this embodiment, one seal can activate at a lower squeeze force than the other, and the user would merely squeeze less to burst one of the frangible seals and then squeeze harder to burst the other. The heating/cooling pouch 302, and the product reservoir pouch 308 and combination product/heating cell are preferably made of the similar materials and manufacturing methods as the reservoir 30.

Alternatively, a heating/cooling element such as the pouch 302 may be located internally in the reservoir 30 to allow for a combination of conductive and convective heat transfer such as described and illustrated in U.S. Pat. No. 6,484,514, issued Nov. 26, 2002 to Joseph, et al.

The mitt 10 and/or the heating/cooling element may further include one or more insulation layers. The insulation layer(s) may provide for more efficient conductive heat transfer by insulating sides and/or portions of the heating/cooling element to reduce heat transfer in areas where it is not desired. The insulation layers may also protect the consumer and/or materials of the mitt 10 from damage caused by hot and/or cold temperatures.

Manufacturing Process:

A manufacturing process suitable for manufacturing applicators in accordance with the present invention is schematically illustrated in FIGS. 15 and 16.

Figure 56:
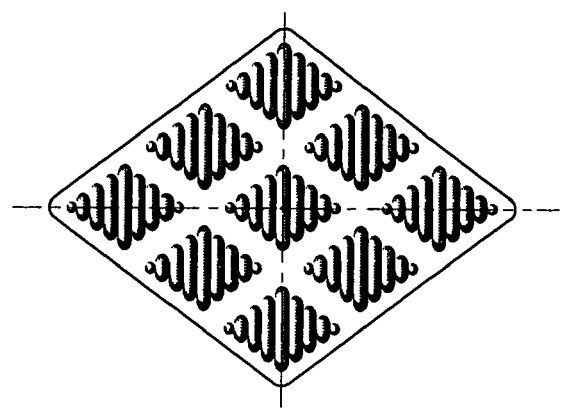
FIG. 56 is a top plan view of an embossing pattern for texturing films, nonwovens, papers and other materials.

As shown in FIG. 15, the process 100 begins with the feeding of a first web 102 from a supply roll 104. The first web 102 corresponds to the front panel 24 of FIG. 2. A glue applicator 106 applies a thin layer of adhesive 107 to the upper surface of the first web 102 in a suitable pattern for substantially uniform coverage, such as a spiral pattern as shown more clearly in FIG. 16. The adhesive is used to establish a bond between the first web 102 and the second web 108, which is fed from a supply roll 111, to form a composite web. The second web 180 corresponds to the tissue layer 37 shown in FIG. 2. Webs 102 and 108 may also be embossed with a pattern such as shown in FIG. 56 to further bond the layers together as well as to provide a unique appearance and an additional scrubbing surface area. Alternative embossing patterns can be used to change the softness, scrubbing ability and porosity of these two layers.

Once the first and second webs are secured to form a composite web, at least one reservoir 114 (corresponding to the reservoir 30 of FIG. 2) is placed in an appropriate location in relation to the web dimensions so as to be located within the dimensions of the finished applicator. Any suitable apparatus 116, such as a "pick and place" apparatus, may be utilized to place the reservoirs 114 upon the traveling composite web. Beads of adhesive 113 from an adhesive applicator 112 may be utilized to secure the reservoirs 114 in place.

Next, the third web 118 corresponding to the barrier layer 25 of FIG. 2 is applied, first being fed from a supply roll 121 through a pair of opposing rolls 119 that may perform an "elasticizing" operation to selectively strain the web to impart elastic-like properties, as described above. The web 118 is then applied to the composite web over the reservoirs 114, and is held in a tensioned condition via the use of any suitable apparatus 122, such as a "vacuum conveyor". The web is preferably stretched by at least 30%, and preferably at least 50%, to obtain the desired level of rugosities or stretched from about 0% to about 5% for no rugosities. The composite web then passes through a sealing/bonding apparatus 123, such as a pair of compression rolls (with cavities as necessary to avoid prematurely rupturing the reservoir 114), which bonds the composite web together with the barrier layer in a stretched or unstretched condition. As best seen in FIG. 16, the cross-direction tension on the composite web is then released and the contraction of the third web causes the first and second webs to corrugate or pleat to form the plurality of rugosities 125, corresponding to the rugosities 50 of FIG. 11. In embodiments in which no rugosities are formed, the tension in the web may be nearly the same for all the layers such that the finished web may lay flat with little or no curl.

Finally, the fourth web 127 corresponding to the back panel 26 of FIG. 2 is unwound from supply roll 133, optionally coated with a friction-enhancing substance from applicator 128, and then applied to the composite web. As mentioned earlier, friction-enhancing elements can be added in various forms such as panels, strips and beads, in addition to coatings. Consequently, such elements could alternatively be added to one or more of the webs joined to define the internal cavity as described, such as by adhesive, spray coating, heat sealing or other lamination techniques as known in the industry. A suitable apparatus 132, such as a continuous rotary heat sealing apparatus, an ultrasonics sealer, high pressure compression sealer, etc., may be used to join the fourth web to the remainder of the composite web by forming a peripheral seal around the edge of what will become the finished applicator, such as a mitt, in the desired outline shape. A rotary die cutting apparatus 134 then severs the finished applicator from the excess material of the rest of the web to form finished applicator or mitt 136. Finished applicators may then be folded, if desired, via the use of folding boards or other suitable apparatus (not shown) and packaged as desired.

Processing conditions for the above process may be determined in accordance with procedures known in the art for establishing suitable operating conditions such as seal temperatures, nip pressures, line speeds, and the like.

EXAMPLE 1

An applicator made in accordance with the present invention may include a glass cleaning mitt, such as described in detail in copending U.S. application Ser. No. 10/089,355 entitled "Semi-enclosed Applicator for Distributing a Substance onto A Target Surface" and filed by Gruenbacher et al on Oct. 9, 2000, which is incorporated by reference. The glass cleaning mitt can provide a flexible structure for distributing glass cleaning substance onto a target glass surface. Such an applicator might include a first fluid-containing reservoir having a predetermined amount (e.g., in the range from about 5 cc's to about 20 cc's) of a liquid cleaning product such the CINCH® brand product as available from The Procter & Gamble Company, Cincinnati, Ohio. The mitt itself may include a front panel layer comprising a polypropylene spunbonded nonwoven material to provide a substrate for spreading the cleaning substance and scrubbing the surface with the cleaning solution. For example, a spunbonded non-woven may be provided having a basis weight in the range from about 10 gsm to about 100 gsm, more preferably from about 15 gsm to about 55 gsm, and most preferably from about 25 gsm to about 45 gsm in order to provide sufficient durability and strength to provide a resilient glass cleaning product. A spunbonded nonwoven is commercially available from BBA Nonwoven of Simpsonville, S.C., under the Celestra name. This material is preferably substantially free of surfactants or other treatments that might leave residual material on the surface being cleaned.

A reservoir 30 may have a frangible seal connected to a distribution channel that provides fluid communication with one or more distribution apertures located in a region or application surface of the mitt corresponding to the position of a user's fingers in use. The reservoir 30 and distribution channel 44 shown in FIG. 19, for example, show one possible arrangement for a glass cleaning mitt. The reservoir itself can be located on the mitt near a cuff region such that the frangible seal 40 is located below the palm of the wearer's hand as shown in FIG. 18 such as described above.

The reservoir and/or the distribution channel can be located between a layer of absorbent material such as tissue layer 37, and a barrier layer, such as the barrier film layer 25. The absorbent layer may wick and assist in spreading the product throughout the surface of the mitt during application, while the barrier layer keeps the product from contacting the user. The tissue layer 37 may have a basis weight in the range from about 10 gsm to about 30 gsm. For example the basis weight of the tissue layer 37 may be about 20 gsm. In one embodiment, the tissue layer may be a single ply of CelluTissue 7020, a product of the Ceull Tissue Corporation of East Hartford, CT about 20 gsm. In another embodiment, the tissue layer 37 may include a single ply of Bounty® tissue available from the Procter & Gamble Company of Cincinnati, Ohio. An additional absorbent layer such as tissue layer 17, which may be similar in material and construction to the tissue layer 37, may also be located between the barrier film layer 25 and the reservoir 30 and/or the distribution channel 44 to help direct the product towards a particular portion of the mitt, such as toward the portion of the mitt that corresponds to the fingertips of a wearer during use. A pressure sensitive adhesive such as one made by Ato Findlay of Wauwatosa, Wis. under the designation of product H2031, may provide adhesion for combining layer 24 to tissue layer 37, layer 37 to layer 25 and/or tissue layer 17 to layer 25. The adhesive may be applied as lines with spacing of about 3 mm to about 4 mm apart, for example, with a basis weight of about 5 gsm. The back panel 26 of the mitt may comprise a substantially absorbent material such as a multiple-ply layer, e.g., four plies, of Bounty® paper towel product discussed earlier. The multiple-ply layer of substantially absorbent material may be used to provide a distinct surface for removing and absorbing residual glass cleaning product and dirt left on the glass after cleaning with the nonwoven side of the mitt. Further, friction enhancing elements, such as the strips of friction-enhancing elements 182 shown in FIG. 22 or other friction-enhancing elements described above, may be located on the inner surface of the front panel or the back panel of the mitt. In one embodiment, the friction-enhancing elements 182 can comprise non-slip coatings of a material such as a hotmelt made by Ato Findlay of Wauwatosa, Wis. under the product designation 195–338. The strips shown in FIG. 22, for example, are positioned in the top half of the mitt to provide contact with the fingers and/or the palm of the wearer's hand and to prevent the mitt from slipping on the wearer's hand during use. The basis weight of the friction enhancing element(s) may preferably be in the range from about 40 gsm to about 180 gsm, and more preferably in the range from about 90 gsm to about 130 gsm.

In another example, the glass cleaning composition of the invention may leave an opaque, translucent, white or other colored film or cream when applied to the surface. Such a film can be obtained via any method known in the art. For example, it is known that many water-insoluble silicones are milky in water. A composition consisting of such silicones and oxygenated glycol ether solvents will leave a milky film on the treated surface. Upon evaporation, the solid residue and can easily be buffed off using either external surface of the mitt. Other substantially water chemistries such as long chain surfactants, emulsifiers or other polymers can also be employed. Use of longer chain surfactants such as sodium hexadecyl sulfate are advantageous in that they can provide lubricity characteristics to the treated surface. As a result, users applying the product will not only derive the satisfaction of easily removing a milky residue and leaving surfaces streak-free, they will also experience the tactile benefit associated with a pushing the mitt across a smooth surface. Cleaning product formulations having low solids compositions can provide improved filming and streaking performance over identical compositions that use conventional paper towel technology. While not wishing to be limited by theory, it is believed that the use of a non-absorbent substrate layer for spreading cleaning fluid across the glass provides a benefit in that it ensures even distribution of product over the surface covered. Conventional glass cleaning processes employ absorbent paper towel for both the distribution of wet product, and the buffing step. As a result, cleaning composition is simultaneously spread and absorbed even though the user just wishes to spread product. Since the absorbent capacity of the traditional implement is limited, some parts of the glass are exposed to higher active levels than others. This inequity in product distribution can lead to streaks following the buffing step. Traditional glass spray users would have to use two separate substrates, in addition to the cleaner, just to get the same level of performance excellence achieved by the mitts. Optionally, other ingredients such as polymers for antifog or water sheeting benefits can optionally be used with the mitts of the present invention provided that filming and streaking performance is not excessively compromised.

The mitts can be used for cleaning glass surfaces including but not limited to, inside and outside windows, mirrors, television screens, tables, and car windows. They can also advantageously be used to clean other surfaces such as vinyl, Formica®, enamel, porcelain, wood, aluminum, steel, chrome, and the like. Applications include cleaning or refreshing countertops, indoor or outdoor furniture, upholstery, painted walls, wallpaper and floors.

EXAMPLE 2

An applicator made in accordance with the present invention may include a personal care mitt. For example, these mitts may be used for the purpose of, but not limited to, beautifying (i.e., improving the visual appearance and/or feel), cleaning, moisturizing, conditioning, or otherwise treating the skin, hair, or nails. Product applications include, but are not limited to, face and body cleansers, toners, lotions, moisturizers, ointments, cosmetics/make-ups, medicaments, and related topically applied treatments.

Figure 58:
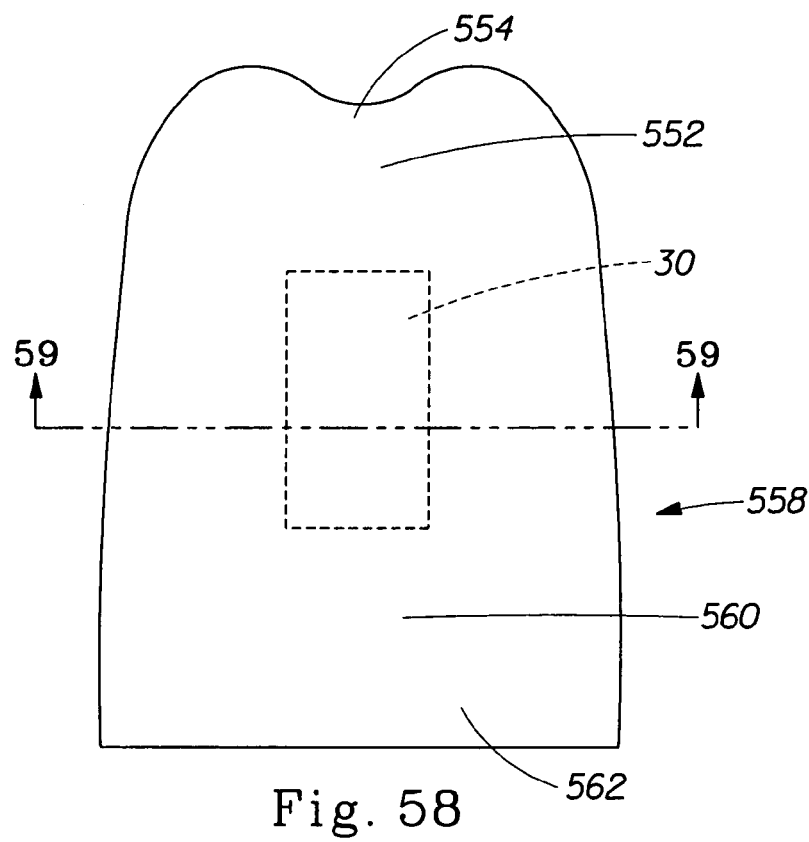
FIG. 58 is a plan view of a preferred embodiment of a semi-enclosed heating/cooling applicator in accordance with the present invention, in the form of a mitt.
Figure 59:
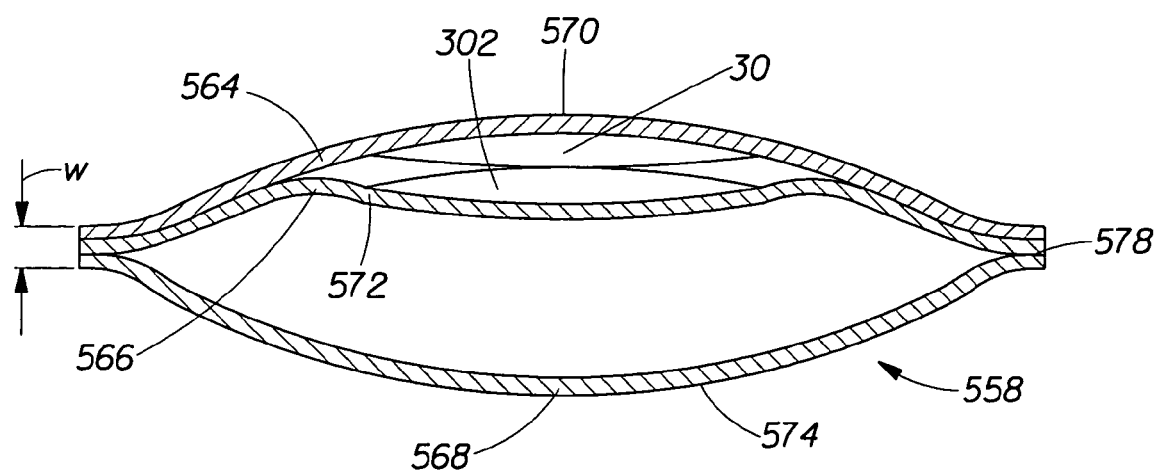
FIG. 59 is a cross-sectional view of the mitt of FIG. 58 taken along line 59—59.

As shown in FIG. 58, for example, a two-finger mitt 558 for applying a heated moisturizer to the face may be made in accordance with the present invention. In this embodiment, the mitt 558 may include a heat producing pouch 302 and a product dispensing pouch 30 that may be similar to that shown in FIG. 4. As shown in the cross-section FIG. 59, the top panel 564 may be constructed of a hydroentangled nonwoven having a basis weight of about 60 gsm that may include approximately 75% polyester and approximately 25% rayon. This structure may slow product release once the pouches have been ruptured by limiting product escape, and it may also provide an exfoliation benefit to the skin as outer surface 570 rubs across the face during application. As demonstrated in FIG. 48, the features of the product pouch 30 and heat pouch 302 may be combined into a single pouch 326 featuring separated compartments. The pouch may be folded between the product compartment 318 and reactant compartment 320 such that compartment 318 rests on compartment 320 when assembled into the mitt such as shown in FIG. 50. The pouch may be oriented in the mitt such that compartment 322 is closer to the finger tips than the compartment 320. In one particular embodiment, the compartment 320 may contain about 1 gram of $H_2O$ and the compartment 322 may contain about 1 gram of $MgSO_4$. A frangible seal 324 may be sealed under conditions such that it would rupture with less force than the frangible seal 314. Thus, when squeezed by the user, the product would not be released from the compartment 318 until the heat-producing reactants are allowed to mix. Because of the pouch arrangement and orientation, the product from the pouch 318 may be expelled onto compartment 322. Thus, because the heating area, the location of product expelled, and location of the user's fingers, the heat cell may heat the product and the user's skin as it is pressed and rubbed against the face. The barrier layer 566 may be a 5 mm thick open-cell polyurethane foam to prevent product from reaching the fingers and to also insulate the fingers from uncomfortable levels of heat. Furthermore, the barrier layer may prevent the tactile properties of the product released from compartment 318 from being noticed by the user. Finally, the backsheet 568 may be constructed of 20 GSM carded polyethylene nonwoven. The cross machine direction of the nonwoven, for example, may be oriented such that it is perpendicular to the length of the users fingers when placed on the hand. This may allow the mitt to accept a variety of finger sizes since the strength in the cross-machine direction is less than that of the machine direction of the nonwoven; thus, the backsheet can be stretched to accommodate the user's fingers. To use the applicator, the user may press the applicator on pouch 318 to release the product and simultaneously activate the heating pouch. The user may then apply the product to the face by rubbing the mitt against the skin.

In preferred embodiments, compositions of the present invention may be suitable for application to the skin, hair, or nails of humans or animals, which means that the composition and its components are suitable for use in contact with skin, hair, and nails without undue toxicity, incompatibility, instability, allergic response, and the like within the scope of sound medical judgment. Such products are comprised of a single or plurality of ingredient components, and may include a topically active component or combination of active components. These components may include, but are not limited to, conventional ingredients such as alcohols, colorants/pigments, emollients, emulsifiers, oils, polymers, waxes, and the like depending on the product type, and can be routinely chosen by one skilled in the art for a given product type. The CTFA Cosmetic Ingredient Handbook, Second Edition (1992) describes a wide variety of non-limiting cosmetic and pharmaceutical ingredients commonly used in the skin care industry, which are suitable for use in the composition of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, methyl lactate witch hazel distillate), anti-acne agents, anti-caking agents, anti-foaming agents, anti-fungal agents, anti-inflammatory agents, anti-microbial agents (e.g., iodopropyl butyl-carbamate), anti-oxidants, anti-wrinkle agents, binders, biological additives, buffering agents, bulking agents, chelating agents, chemical additives, colorings/colorants, cosmetic astringents, cosmetic biocides, denaturants, desquamation actives, drug astringents, external analgesics, film formers or materials, e.g., polymers, for aiding the film-forming properties or substantivity of the composition (e.g., copolymer of eicosene and vinyl pyrrolidone), opacifying agents, pH adjusters, reducing agents, sequestrants, skin bleaching and lightening agents (e.g., hydroquinone, kojic acid, ascorbic acid, magnesium ascorbyl phosphate, ascorbyl glucosamine), skin coloring or tanning agents, skin-conditioning agents (e.g., humectants, including miscellaneous and occlusive), skin-soothing and/or healing agents (e.g., panthenol and derivatives (e.g., ethyl panthenol), aloe vera, pantothenic acid and its derivatives, allantoin, bisabolol, and dipotassium glycyrrhizinate), skin-treating agents, sunscreens, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Preferred Properties of Product a) Viscosity

Products suitable for use in the present invention may cover a broad range of viscosities, so long as the product either readily flows or can otherwise be dispensed or discharged from the reservoir by a squeezing action or external pressure applied on the reservoir by the user. In particular, they may range from low viscosity liquids (e.g., water) to high viscosity liquids, emulsions, mousses, gels, or pastes, on the order of several thousand to several hundred thousand centipoise. While not wanting to be limiting, products with a shear-thinning or thixotropic behavior are particularly well-suited to the present invention, benefiting from the shear stresses produced on the product by the application of external pressure to the reservoir and/or the act of rubbing dispensed product from the applicator onto a target surface.

b) Melt Point, Solidification Point, or Glass Transition Temperature

Compositions or components characterized by melt point or softening point temperatures less than about 200° F. but greater than the temperature of the target application surface may be especially well-suited to benefit from the heating embodiment of the present invention. For example, semi-solid or solid fat or wax components of an animal, plant, mineral, or petroleum nature that are rigid or hard at body temperature can be transformed to a more soft or fluid state by the heating embodiment, thus further extending the range of usable product types. Semi-solid or solid products that would normally be either unusable or applied unevenly or with great difficulty at a given temperature can, with the present invention, be made usable and applied with greater ease and uniformity. Similarly, compositions or components characterized by solidification point or freezing point temperatures greater than about 30° F. but less than the temperature of the target application surface may be especially well-suited to benefit from the cooling embodiment of the present invention. For example, liquid or semi-liquid components that are very fluid or low in viscosity at ambient temperature can be transformed to a firmer, more structured or thickened state by the cooling embodiment. This may enable a more controlled, uniform or otherwise desirable application of product to the target surface, or provide a means for certain products to be formulated with little or no conventional structuring or thickening agents. Polymers characterized by glass transition temperatures in the previously stated ranges would also benefit from the aforementioned heating and cooling embodiments.

Applicator Surface Temperature

For some applications, surface temperature of the applicator need only be limited by the operating capabilities of the chemical reactant composition and/or service limits of the surrounding applicator materials. However, for applications where skin contact is directly involved, it is preferable to design the chemical reactant composition and surrounding applicator materials and construction such that the skin-contacting surface temperature does not exceed a threshold of pain or discomfort. For heating, the preferred range is between body temperature and approximately 120° F., for a period less than or equal to 20 minutes, and more preferably for a period between 1 and 5 minutes. The skin, pores, and underlying circulation of blood is thereby stimulated during application, providing a soothing or comforting sensation, and further aiding the application and absorption of product into the skin. For cooling, colder temperatures are known to cause pores to restrict. Such pore restriction is commonly used at the end of a beauty care regiment.

Avoidance of Product & Temperature Exposure to Fingers/Hand

The present invention is particularly useful in preventing the exposure of product and/or significant temperature change (produced by the chemical reactant pouch) to the fingers or hands of the user. The ability to prevent product exposure to the fingers or hands during use is particularly advantageous in mitigating undesirable tactile or skin feel properties or absorption of product onto non-target skin. With regard to tactile/feel properties, there are many product compositions or ingredient components, especially many active ingredients, having undesirable tactile properties, such as greasiness, tackiness or stickiness, or slipperiness. Representative examples include, but are not limited to, petrolatum or petroleum jelly (greasy), castor oil or sunscreen (e.g., octocrylene) (oily/greasy), tocopheryl acetate or gums (sticky/tacky), and non-volatile organo-substituted polysiloxanes (e.g., nonvolatile dimethicone fluid) (slippery). By using the present invention, such compositions or ingredients may be applied and used on the body or face without undesirable feel or residue imposed on the fingers or hand. With regard to absorption of product onto non-target skin, the present invention can prevent undesirable color, odor, or other activity from occurring on the fingers or hands. This other activity, for example, could be from skin lightening/bleaching or tanning actives remaining on the fingers or hands. However, it should be understood that suitable compositions or components of the present invention are not required to be of the aforementioned characteristics.

Multi-Functional Sides

The applicator of the present invention can be constructed to provide more than one functional side for use. For example, multiple steps or benefits of a skin treatment process can be accomplished with a single applicator of the present invention. One side may be used to perform a function that is independent, sequential, or complimentary to a second side. The mitt may even be everted to provide a total of four functional sides. Such functions include, but are not limited to, cleansing, scrubbing, exfoliation of dead skin cells, absorbing or picking up substances from the target surface, or depositing substances to the target surface. Depending on the application, these functions can be accomplished by proper selection of substrate material types and properties, or additional texture imposed by patterns or embossing on the substrate. The substrates may be synthetic and/or natural, woven and/or non-woven, and have absorption properties ranging from hydrophobic to hydrophilic.

Product Integrity

The product reservoir of the present invention is particularly well suited to protecting and maintaining the integrity of the preferred compositions or components. This product integrity may take the form of protection from microbiological insults, oxidation, evaporation, or moisture. Protection from oxidation is especially valuable in sustaining the efficacy of many active ingredients (e.g., Vitamin A).

Massaging Feature

Additional skin stimulation or surface abrasion may be provided from the applicator with the inclusion of a massaging structure or feature positioned behind the outer substrate without impeding the dispensing feature of the present invention. For example, this may take the form of a rigid pleated, corrugated, or ribbed structure, rigid raised or recessed surface protrusions, void spaces or perforations within an otherwise solid flat structure, rotating or rolling balls/cylinders/rods, and three-dimensional patterns embossed, engraved, or otherwise formed in a solid material. Examples of suitable rigid or solid materials include, but are not limited to, plastics, metal, ceramics, and composites. Material may be selected based on such factors as hardness or chemical resistance suitable for the desired use.

EXAMPLE 3

Another example of an applicator made in accordance with the present invention is a rubber, vinyl, and plastic protectant mitt provided as a flexible structure for distributing cleaning, protecting, and shining formulations onto a target surface. Such an applicator may include a first fluid-containing reservoir having a predetermined amount, such as in the range from about 12 cc's to about 25 cc's of a protectant product. A protectant product is defined for the purposes of this application as a formulation that prevents drying, cracking, fading and/or discoloration caused by at least one or a combination of UV radiation, high temperature, ozone, dust and dirt. An exemplary protectant product that may be used in the present invention is an Armor-All® Protectant as available from The Armor All Products Corp., Oakland, Calif. The front panel 24 may be comprised of a synthetic woven, synthetic knit, nonwoven, apertured film, macroscopically expanded three-dimensional formed film, absorbent or fibrous absorbent material, foam, or laminates and/or combinations thereof. The nonwovens may be made by, but not limited to, one of the following methods: spunlace, spunbond, meltblow, carded, air-laid, and hydroentangled. One such material sufficient in durability and strength to provide a cleaning surface is a spunbond polypropylene nonwoven such as from BBA Nonwoven of Simpsonville, S.C. Other structures such as hydroentangled materials comprising cellulose, rayon and polyester may also be used. One such set of materials are made by Dexter Corporation of Windsor Locks, Conn. and sold under the trade name Hydraspun®. One skilled in the art will understand that a wide range of materials can be used as long as the material of interest provides the required durability to complete the cleaning task.

A reservoir and distribution channel may also be provided for the reservoir 30 such as described above. In such a protectant mitt, the reservoir can be located between a layer of tissue 37 or other absorbent material and a second layer of tissue 17 or other absorbent or located between a layer of tissue 37 or other absorbent material and a barrier layer 25, where the absorbent wicking layer(s) would assist in spreading the fluid throughout the front panel 24 while the barrier layer keeps the fluid from contacting the user. The barrier layer can be textured by any means known in the art, including but not limited to, embossing, ring-rolling, and incremental staining, and may also be rendered extensible. The barrier layer can be combined with another "softness enhancing" material that provides additional comfort, softness and tactile feel to the user's hand on the front inner surface 32. Such materials can include, but are not limited to, fibrous (natural, synthetic, or combination thereof) or foamed materials.

On the back side of the mitt, a substantially absorbent material such as the Bounty® discussed earlier might preferably be utilized to provide a distinct surface for removing and absorbing residual product and dirt left on the plastic, vinyl, or rubber after cleaning with the front panel 24 of the mitt. The mitts can have a barrier film 27 on the back inner surface 34. As described above for barrier layer 25, this material can also be textured by any method known in the art and/or rendered extensible.

The mitts can be used for cleaning rubber, plastic, and vinyl surfaces including but not limited to, vinyl and other plastic car interior surfaces (i.e. dashboards, door panels, trim, consoles, plastic seats, etc.), and vinyl and other plastic car exterior surfaces (i.e. bumpers, trim, vinyl tops, moldings, etc.), rubber automobile tires, as well as, other vinyl and plastic surfaces such as indoor and outdoor furniture, luggage, and the like. As in the glass surface cleaning example described above, the mitts are ideally suited for cleaning curved or other surfaces with jagged edges or tough to reach areas and can be stored individually, or placed and stacked in containers, folded or unfolded. The combination of easy storage and ability to clean tough to reach areas such as car dashboards, consoles, and trim, makes them ideal for use in the car (glove compartment storage), where conventionally applied protectants are awkward, ineffective and potentially hazardous.

EXAMPLE 4

A baby cleaning mitt, for example, may include a first reservoir situated to wet an outer surface of the mitt and a second reservoir situated to wet a substrate that is initially on the inside of the mitt. In this example, the outside of the mitt may be wetted with a cleaning solution to clean the baby. One side of the mitt can be kept dry allowing the baby's skin to be patted dry. The mitt can then be everted and, in one embodiment, sealed shut with a layer of pressure sensitive adhesive that can be applied to the outer cuff region of the mitt such when the mitt is everted the cuff can be pressed shut and held tightly closed by the adhesive. Closing the everted mitt may reduce odors and may also reduce the chance of loose bowel movement falling out of the mitt. The everted mitt now also exposes two new surfaces where one or both surfaces can have a reservoir for applying an additional substance to the baby's skin, such as a lotion that moisturizes and prevents diaper rash. In this case, the everted and sealed shut mitt has become a two-sided wipe with the ability to apply additional substances if needed. The reservoirs for the inside surfaces can be located in a region that prevents pre-mature bursting or can have a higher burst force level so that they don't burst when the person is initially performing the cleaning task.

EXAMPLE 5

Another example might be a mitt suitable for Pet Care applications. For example, the mitt could include a front panel having an odor absorbing nonwoven structure such as an activated carbon cloth to absorb pet odors and a back panel including a different nonwoven with a bursting pouch containing a conditioner or possibly an odor neutralizing liquid such as FEBREZE®, a product marketed by The Procter & Gamble Company. Suitable odor neutralizing liquids useful herein are described in the following U.S. Patents, which are incorporated by reference herein: U.S. Pat. Nos. 5,783,544; 5,714,137; 5,593,670; 5,939,060; and 5,942,217. The mitt may allow the pet owner to rub around the pet's face without worrying about the need to control a spray or stream of liquid product. Another pet care mitt application may include a pet hair removal mitt in which the mitt includes bristles on the front panel and/or the back panel. These bristles can be created by injection molding or thermoforming a separate part that is bonded to the front panel or the back panel, or forming the bristles directly onto the front panel and/or the back panel using techniques such as those used to make mechanical fasteners such as described in U.S. Pat. No. 5,058,247 filed by Thomas, which is incorporated by reference. The reservoir may include a liquid or lotion product that wets the panel surface and is dispersed onto the pet or other target surface being cleaned making it easier to remove the hair with the bristles from a shedding pet or from a surface such as carpet, upholstery and furniture.

EXAMPLE 6

Figure 52:
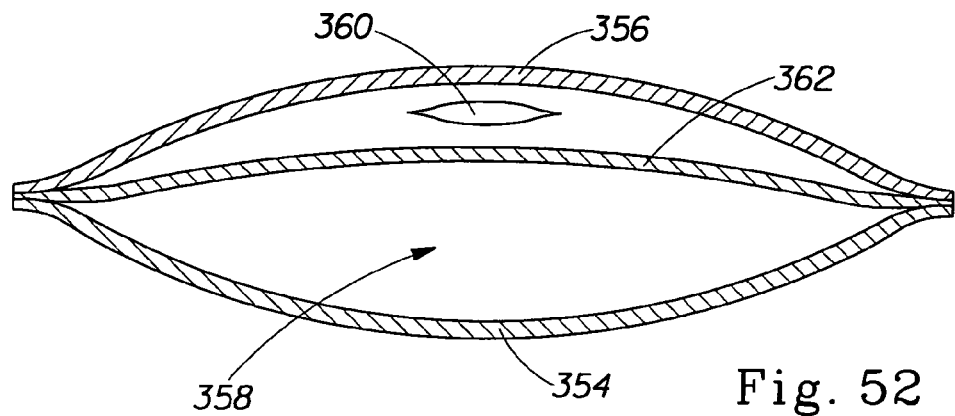
FIG. 52 is a cross-sectional view of a mitt described for use dusting and polishing furniture.

As shown in FIG. 52, a dusting/polishing mitt such as for use with furniture may be made in accordance with the present invention. The dusting/polishing mitt may include a dusting side 354 and an applicator side 356 that may apply a product such as a furniture polish. The dusting side 354 may include a treated or untreated polyester nonwoven material such as sold by the Procter & Gamble Company of Cincinnati, Ohio under the SWIFFER® name or may be any other known dry or impregnated dusting material. The applicator side 356 may, for example, comprise a composite of two layers with a rupturable reservoir contained within the composite. The applicator side 356 may be sealed to the dusting side 354 to form a mitt shape with one end left open for creating an opening 358 into which a hand may be inserted. The applicator side 356 may, for example, comprise a 58.5 gsm hydroentabled nonwoven fabric comprised of cellulose, rayon and polyester fibers made by the Dexter Corporation of Windsor Locks, Conn. A rupturable dosing pouch 360 may be located beneath one or more layers of the applicator side 356 and may contain, for example, about 10 cc's of Pledge furniture polish made by S.C. Johnson of Racine, Wis. Beneath the dosing pouch, a barrier layer 362, such as a 1 mil LDPE film, may be embossed to provide good hand feel on the inside of the pouch, while also providing a moisture barrier to protect the hand. The multiple layers of the applicator side may be bonded together such as by intermittently using a spiral hot melt glue applied at a weight of about 4 gsm. The dusting side 354 of the dusting/polishing mitt may be used to remove loose dust, and the applicator side 356 may be used to dispense furniture polish to the target surface as needed. The user could alternate between the dusting side 354 and the applicator side 356 allowing one mitt to be used to polish and dust an entire home or room. Alternatively, the back panel 354 may be a buffing side to remove excess polish and/or to buff the target surface to a shine. A suitable buffing side 356 may be cotton, nonwoven and/or cellulose-based structures. A suitable nonwoven, for example, maybe an absorbent and soft hydroentangled nonwoven made by Dexter Corporation such as the same material described above with reference to the applicator side. Another suitable material may be the Bounty® material made by The Procter & Gamble Company described above.

EXAMPLE 7

Another example of a mitt of the present invention is a finger applicator mitt that fits on at least a part of one or more fingers. A finger mitt allows for precise control of the applicator that may be preferable for getting into tight spots and/or for better dosing control and dispensing accuracy. A finger mitt of the present invention may allow for application of facial lotions and creams, cosmetics, liquid foundation, toothpaste or other dentifrices, sunscreen, etc. A facial lotion applicator, for example, may allow a consumer to precisely control the product application without fear of getting the product in an eye.

Figure 13:
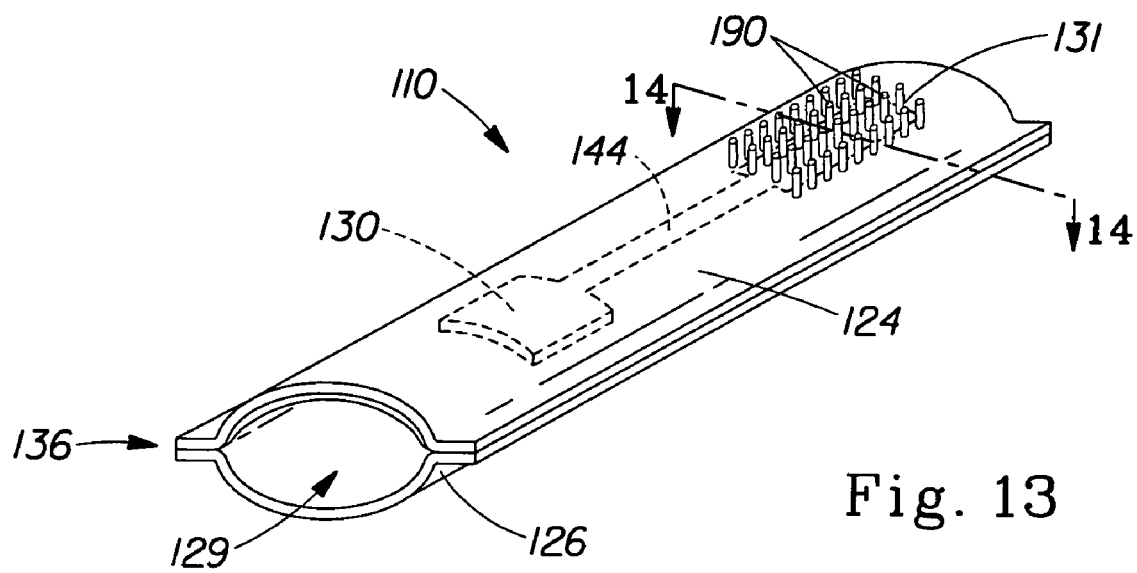
FIG. 13 is a perspective view of an exemplary finger mitt applicator made in accordance with the present invention.
Figure 14:
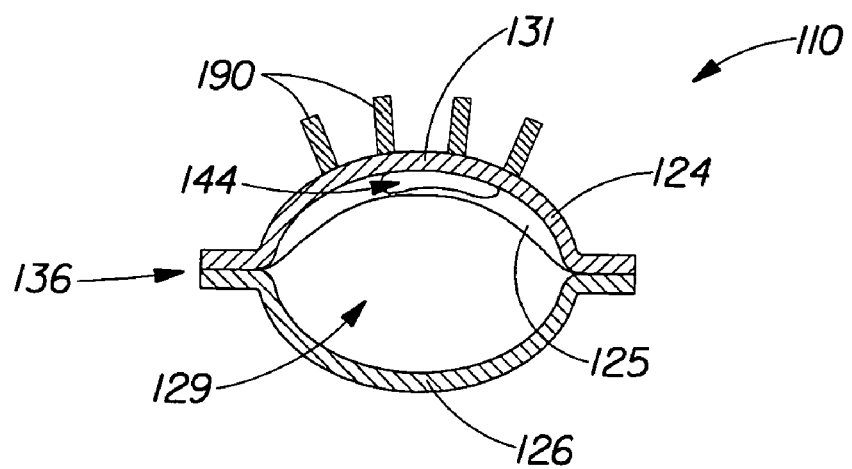
FIG. 14 is a cross-sectional view of the finger mitt applicator of FIG. 13, taken along line 14—14.

The finger mitt may have a similar construction as the hand mitts but can be sized to only fit on part of one or more fingers. FIGS. 13 and 14, for example, show a finger mitt 110 for dispensing toothpaste on the edge of the finger as needed. A cylindrical hollow interior 129 into which at least a portion of a user's digit could be inserted is illustrated, having a front panel 124 with optional outwardly extending bristles 190 on front outer surface 131 for a toothbrush or scrubbing application. A reservoir 130 similar to that shown and discussed herein with respect to FIGS. 3 and 7 is shown in phantom. The reservoir 130 shown includes a frangible seal and a distribution channel 144 to dispense a product to an end of one or more fingers. This same mitt could also be used to dispense a variety of other lotions, creams, or liquids to a specific location.

These smaller mitts would preferably be formed of a substrate such as front panel 124 for applying the product, a rupturable reservoir 130, a barrier layer 125 to keep product from contacting the skin, and a second substrate to create the internal cavity for the finger. The layers may be sealed at the perimeter 136 to create the opening 129 for inserting one or more fingers. Optionally, the second substrate can also be designed to absorb a liquid product as described above. Mitts could also be designed to go onto the foot, toes, or a reusable molded applicator part that may be used as an applicator device. The barrier layer and/or the substrates can also be made at least partially extensible, and can include a friction enhancing element as described herein to better fit and stay on the finger. Other alternatives and modifications will be apparent to those skilled in the art without departing from the scope of the present invention.

A suitable soft substrate such as an open or closed cell polyethylene foam could be used as the applicator substrate or front panel 124 to provide a very soft and smooth application surface for applying the product. Bristles (e.g. 190) or abrasive coatings can also be applied to either substrate to provide additional scrubbing or cleaning capability. One method of attaching bristle-like fibers to the substrate includes using a hot melt screen printing process such as is known in the art, where the adhesive pattern printed is elongated in a direction generally perpendicular to the substrate cleaning bristles extending upwardly from the substrate.

EXAMPLE 8

Figure 53:
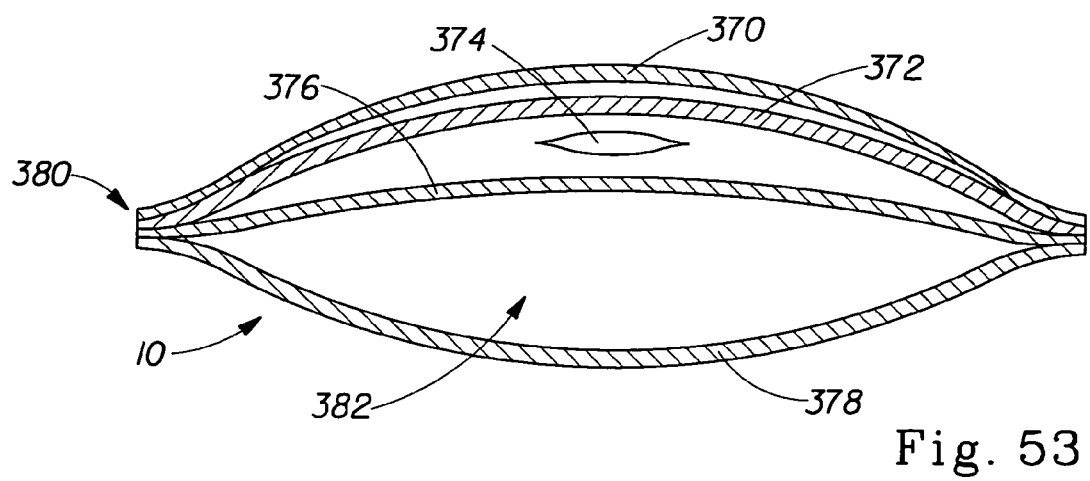
FIG. 53 is a cross-sectional view of the mitt in FIG. 57 taken along line 53—53.
Figure 54:
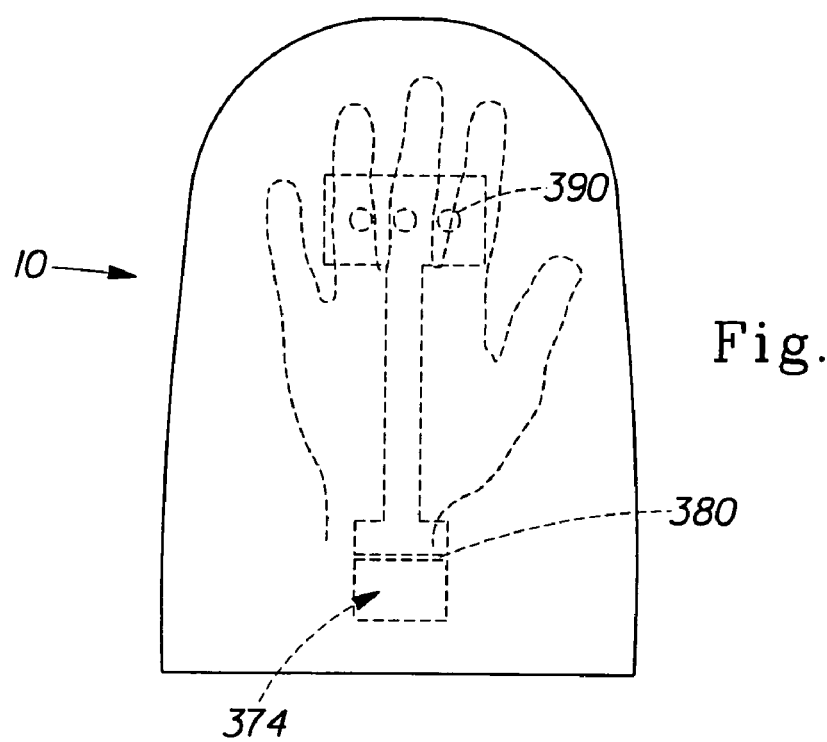
FIG. 54 is a top plan view of mitt described for body cleansing.

A body cleansing mitt 10 may be constructed by having a wet side and a dry side in a mitt form such as shown in FIG. 53. The wet side, for example, may include a 60 gsm spun-bond linear low density polyethylene (LLDPE) nonwoven 370 laminated to a tissue layer 372, such as a single ply of Bounty® tissue made by The Procter & Gamble Company of Cincinnati, Ohio. A dosing pouch 374 containing about 15 cc's of a no-rinse body cleansing solution similar to those used in baby wipes may be disposed underneath the tissue layer 372. Underneath the dosing pouch, a barrier film 376, such as a 1 mil thick polyethylene film, may form the inside layer of one side of the mitt. The other side of the mitt may be used for drying the skin after application. The dry side 378 can include a substantially absorbent layer such as a 60 gsm hydroentangled web comprised of paper, PET, and Rayon fibers or combinations thereof. The dry side of the mitt may be sealed at the edges 380 to the wet side of the mitt in a horseshoe shape leaving an opening 382 for a hand to be inserted between the two sides. FIG. 54 shows a top plan view of a mitt 10 with the reservoir of a dosing pouch 374 shown below the palm of a typical user's hand. The frangible seal may be located below the palm to prevent the reservoir from being dispensed inadvertently during use. The product may be dispensed from the apertures 390 near the fingers of the wearer's hand. The mitt may be formed by bonding the LDPE nonwoven layer, the absorbent layer, and barrier film together, such as by using a spiral glue pattern of a hot melt adhesive such as a Findley H2031 hot melt adhesive at a basis weight of 4 gsm between each layer to be combined. The adhesive bonding between the layers can be accomplished without significantly impacting the porosity or fluid flow of the product through the layer(s). Alternatively, any heat sealing technique such as ultrasonics, radio frequency, conduction, hot air convection, ultra high pressure, or the like could be used to combine these materials.

The body cleaning mitt may be used by a consumer to clean a body surface with the wet side and then use the dry side to either remove any wetness left on the skin or possibly apply a semi-dry-form of deodorant or perfume. Alternatively a separate dispensing pouch could be located on the dry side that contains a lotion or semi-liquid deodorant and/or anti-perspirant could be located between the inside surface of dry side 378 and an optional additional barrier film bonded to dry side 378.

EXAMPLE 9

Figure 55:
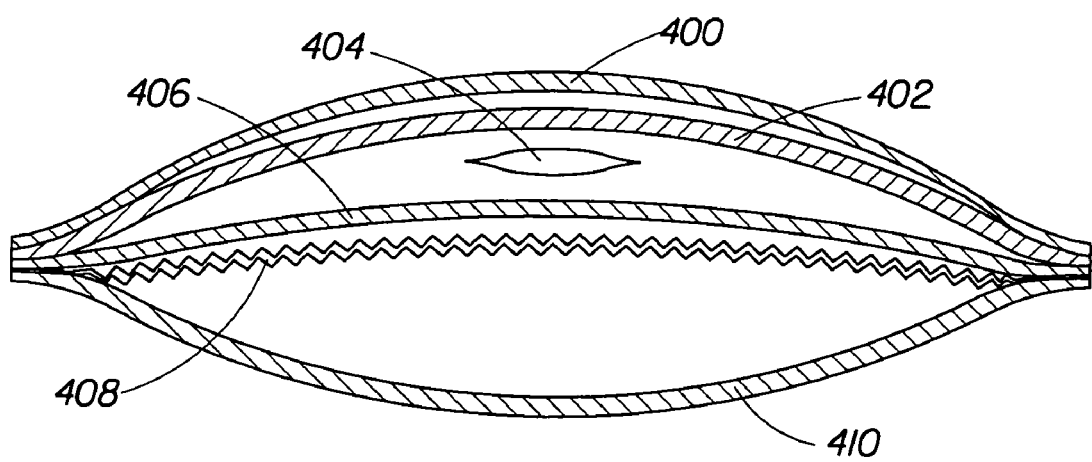
FIG. 55 is a cross-sectional view of a lotion applicator.

A body lotion mitt may also be constructed to have an applicator side and a retaining side that serves to keep the mitt on the hand of the user for ease of application such as shown in FIG. 55. The applicator side may comprise a nonwoven material, such as a 60 gsm LLDPE nonwoven 400, as a soft skin contact layer. The applicator side may further include a flow restriction layer 402 to limit or control product flow to the skin contact layer. One possible material that may be used as the flow restriction layer is a 100 mesh hydropertured 1 mil film manufactured by Tredegar of Terre Haute, Ind. with a nominal hole size of 100 microns. The hydroapetured film, for example, can also be embossed to a level in the range from about 0.01 inches to about 0.08 inches deep with a pattern such as the checkerboard pattern as shown in FIG. 56. Embossing the film may provide greater thickness and may prevent the user from feeling the rupturable pouch and potentially a sharp edge. Underneath the apetured film, the rupturable pouch 404 may contain a product such as about 10 cc's of Oil of Olay's Total Effects Cream® available from the Procter & Gamble Company of Cincinnati, Ohio. The pouch may be designed similar to the design shown in FIG. 2 and may be designed to empty the entire contents of the pouch between a barrier layer 406 and the flow restriction layer 402 upon squeezing. The flow restriction layer 406 may be used to control dosage and thus the amount of the product applied to the skin. The barrier layer 406 may, for example, comprise a 1 mil LDPE film. Beneath the barrier layer 406, single or multiple layers of a film 408 may be embossed to provide a soft cushion-like feel and to make the mitt feel more substantial. For example, three layers of a 1 mil LDPE film may be embossed with a pattern such as the pattern shown in FIG. 56. Each layer may be embossed to a thickness of about 0.04 inches resulting in a total thickness of about 0.12 inches. Alternatively, nonwovens, embossed paper, PET batting material, or other materials could be used to create a soft cushion like feel. An additional layer of film or nonwoven may be used as the back panel 410 to help retain the mitt on the fingers or hand. For example, the back panel 410 may be a 1 mil low density polyethylene film. The user may make a fist once to rupture the pouch and then the flow restriction layer can control the product release such that the product can be dispensed slowly to cover the entire body. In one embodiment, a high coefficient of friction coating, such as a Findley Hot Melt 195-338 or a body adhesive could be applied to the film 154 to create a non-slip surface for the user to grasp.

EXAMPLE 10

Figure 57:
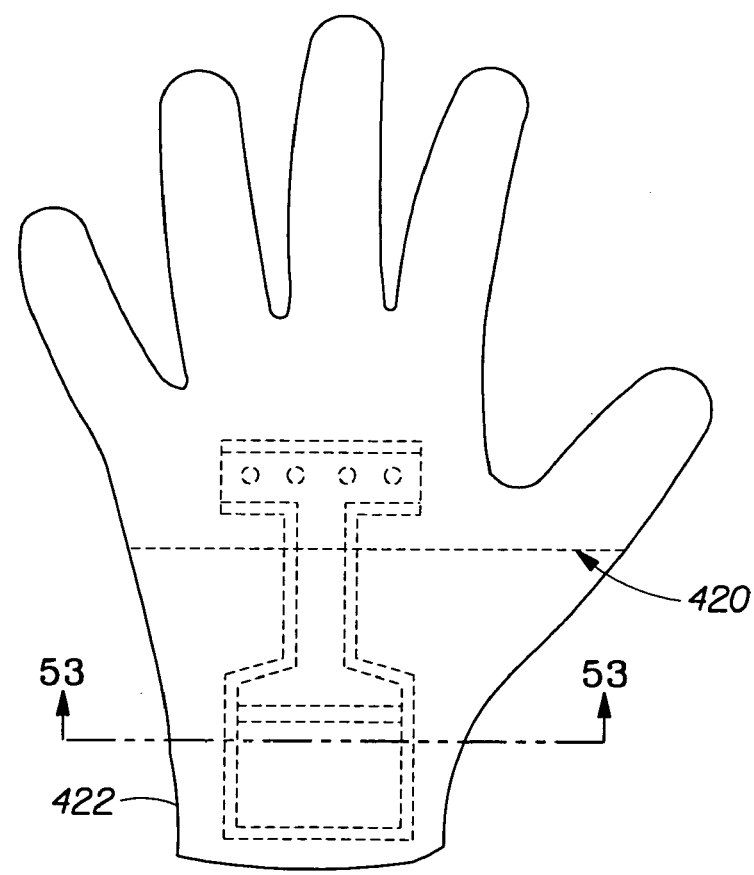
FIG. 57 is a top plan view of one embodiment of a glove of the present invention.

A weed killing glove may also be made in accordance with the present invention such as shown in FIG. 57 with individual fingers and a thumb. The weed killing glove may enable a user to dispense a herbicide such as ROUND UP® herbicide made by Monsanto Corporation onto the surface of a glove. The user may kill weeds by touching the weeds with the glove surface without the risk of an overspray killing surrounding grass, flowers, trees, etc. In this embodiment, for example, a glove may allow for more dexterity than a mitt and may allow for the dexterity and control required to touch individual weeds. Alternatively, a finger mitt that fits over one, two or three fingers may provide the dexterity and control desired. FIG. 53 shows a cross-section of one embodiment of a mitt or glove near the cuff region 422. The glove may be include an applicator side 370 having a protective barrier layer 376 to prevent the herbicide from contacting the hand. The applicator side may include a porous material 370, such as a 34 gsm polypropylene non-woven, bonded to an absorbent distribution layer 372, such as a 21 gsm tissue layer, for controlling the wicking of the fluid to the finger-tips. Two or more absorbent distribution layers 372 may be positioned from the palm to the top of one or more fingers to increase the herbicide distributed to this region such as shown as the region above line 420 in FIG. 57. Beneath the absorbent distribution layers, a rupturable dosing pouch 374 may be located such that the reservoir is located beneath the palm such as shown in FIG. 57. The dosing pouch 374 may be designed similar to the dosing pouch shown in FIG. 24 to direct fluid to the fingertips of the wearer. The next layer can be a barrier layer 376 that may be a 1 mil LDPE film blended with ethylene vinyl acetate to provide good grip. The film may be embossed to deliver a thicker layer as well as to provide better hand feel. The embossing may also create a web that does not drape around the hand and thus keeps the hand cooler. The barrier layer 376 may be sealed around the perimeter 380 in a hand pattern to the back layer, which may include a material similar to the barrier layer 376. An opening 382 may be left between the film layers to allow the hand to be inserted.

EXAMPLE 11

A light duty multiple surface mitt may be made using an anti-bacterial cleaning solution such as 409® cleaning solution made by Clorox Corporation of Oakland, Calif. or Windex® anti-bacterial solution made by S.C. Johnson of Racine, Wis. in the reservoir 30. The mitt may, for example, be constructed generally the same as the glass cleaning mitt described earlier in Example 1, but with an anti-bacterial cleaning formula instead of the glass cleaning formula. The mitt nay have a wet side and a dry side allowing the user to clean bathroom surfaces, sinks, counters, toilets, tables, kitchen surfaces, etc. The dry side may be used to wipe the surface dry leaving a streak-free surface with no sticky residue left behind. An additional layer of polyethylene film can be optionally located on the inside of the drying side to provide additional protection for the hand.

EXAMPLE 12

Figure 61:
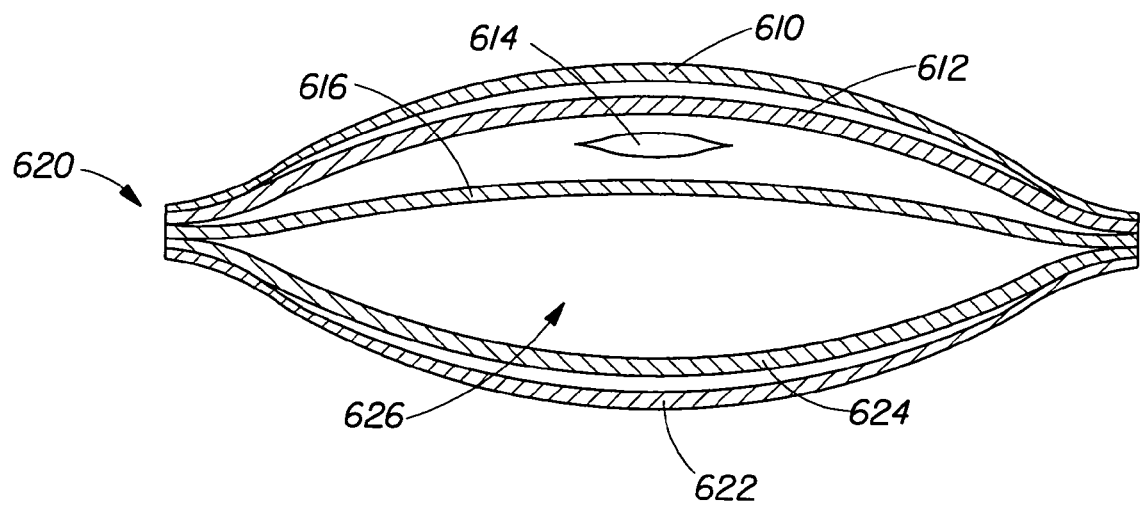
FIG. 61 is a cross-sectional of a bathroom cleaning mitt with barrier layers on both sides of hand.

A heavy duty bathroom shower/tub mitt may include a more durable wet side for scrubbing with a cleaning side and a rinsing side to allow the consumer to rinse the surface with water. See, e.g., FIG. 61. The wet side may comprise an air-laid 40 gsm PET non-woven 610 made by Steams Technical Textiles (Cincinnati, Ohio) with a chemical binder to provide scrubbing. The PET fibers may be open and loose providing good loft and thickness for the substrate and thus more room for mechanical entrapment of dirt and grime. Beneath the scrubbing PET layer a tissue material such as a single ply of Bounty® tissue 612 may be used to wick the fluid across the mitt surface and to prevent product run-off. Beneath the tissue layer may be a dosing pouch containing about 15 cc of liquid Comet Bathroom® cleaner made by the Procter & Gamble Company of Cincinnati, Ohio. The next layer may be a 1 mil low density polyethylene (LDPE) barrier film 616 blended with ethylene vinyl acetate (EVA) to provide good grip. The film may be embossed to deliver a thicker layer as well as provide better hand feel. The embossing also creates a web that does not drape around the hand and thus keeps the hand cooler. The barrier film 616 may then be sealed around the perimeter 620 in a horseshoe pattern to the rinsing back side. The back side may be a 80 gsm hydroentangled nonwoven 622 comprising of cellulose, rayon and PET fibers. This structure has good wet strength and is very absorbent providing a sponge like performance. The 80 gsm nonwoven may be laminated to a 1 mil polyethylene embossed film 624 to provide a moisture barrier and thus prevent the hand from getting wet when rinsing the surface. An opening 626 is left between the film layers 616 and 624 to allow the hand to be inserted. In use the user may use the wet scrubbing side to dose cleaner onto the scrubbing substrate as needed using the dosing pouch. After all of the target surfaces are cleaned, the user then wets the absorbent rinsing side with tap water and proceeds to rinse off the cleaner. This same basic mitt design could also be applied to an oven cleaning mitt where there is a scrubbing substrate suitable for oven and stove surfaces, a formula that dissolves and lifts baked foods, grease, and food products and an absorbent back side that removes the cleaning solution and food to leave a clean, streak free surface.

EXAMPLE 13

A wet/dry mitt may be used for cleaning such as for a baby clean-up application. The mitt may comprise a 40 gsm hydroentangled cellulose, rayon, PET non-woven bonded to a 1 mil LDPE embossed film with a 5 cc rupturable pouch located in-between. The product inside of the rupturable pouch may be a fluid or lotion such as used in typical baby wipes. The embossed film may be sealed to a dry-side in a horseshoe shape as described in previous examples with an opening left for inserting the hand. The dry side may be another layer of the 40 gsm hydroentabled non-woven. The wet/dry mitt may also be used for menses removal and clean-up.

EXAMPLE 14

Figure 62:
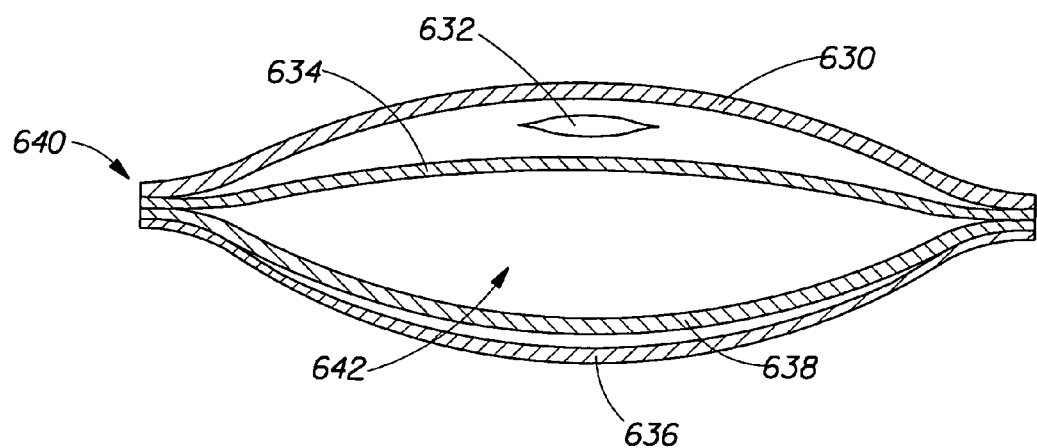
FIG. 62 is a cross-sectional of a flushable wet and dry mitt.

A flushable wet and dry mitt or wipe can be made such as shown in FIG. 62. The front panel 630 can be constructed of a 48 gsm carded non-woven comprising mostly of cellulose with little binder so that it breaks up in the toilet easily. Underneath the front panel, a rupturable sachet 632 may be made from Polyhydroxy Alkanoate (U.S. Pat. No. 5,498,692 assigned to Procter & Gamble) as the barrier pouch material. This pouch can be made rupturable by either a weakened region or by printing a contaminant (ink, polybutylene, etc.) in a seal region such that the pouch controllably ruptures at a given pressure. This biodegradable material will breakdown in a septic system while maintaining it's integrity for shipping and handling as well as a reasonable shelf-life to prevent liquid contained within from evaporating. The liquid inside the sachet 632 may, for example, be 3 ml of a cleaning solution consisting of water, ethanol, perfume, and surfactant. Other biodegradable polymers that provide a sufficient moisture barrier may also be used as the pouch material. For example, one biodegradable polymer that could be used as the pouch material is Bionolle manufactured by Showa Highpolymer Corporation in Japan. Beneath the rupturable pouch, a 25 micron thick polyvinyl alcohol film 634 (Groflex TK5034) from Nordenia Corporation (Gronau, Germany) may be used. The polyvinyl alcohol film (PVA) acts as a temporary barrier to allow one side to stay wet and the other side to remain dry for a short period of time. Various grade of PVA film can be used to deliver different rates as to when the film would dissolve in water and lose it's temporary liquid barrier property. For a clean-up product to be used at the toilet, it is ideally desired for the film to remain a barrier for between 10 and 200 seconds and most preferably between 30 and 60 seconds. Beneath the PVA film, the back panel 636 can be an absorbent paper based product to dry the surface being cleaned before being flushed. This flushable wet and dry wipe or mitt could be used for cleaning up babies after bowel movement, cleaning of the surfaces of toilets, feminine hygiene for menses clean-up and general body cleansing. A mitt could be formed by using an additional layer of PVA 638 and sealing the perimeter 640 in a horseshoe shape with an opening left on one side to allow the hand to fit inside 642. Alternatively the perimeter 640 could be sealed in any shape (rectangle, triangle, pentagon, etc.) with one side left open for inserting hand. Alternatively, the front and back panels can be comprised of any material that is flushable and is durable enough for cleaning and/or drying the surface desired.

While particular embodiments of the present invention have been illustrated and described, it will be obvious to those skilled in the art that various changes and modifications may be made without departing from the spirit and scope of the invention. One skilled in the art will also be able to recognize that the scope of the invention also encompasses interchanging various features of the embodiments illustrated and described above. Accordingly, the appended claims are intended to cover all such modifications that are within the scope of the invention.

The invention claimed is:

1. A semi-enclosed applicator for distributing a product having a first temperature onto a target surface, said applicator comprising:
   (a) a first side having a first external surface:
   (b) a second side;
      wherein said first side and said second side are joined to form an internal cavity therebetween;
   (c) an opening for accessing said internal cavity:
   (d) a rupturable reservoir located proximate to said first side; said rupturable reservoir comprising said product; and,
   (e) a heating and/or cooling element located proximate to said rupturable reservoir;
      wherein said product is released from said rupturable reservoir through said first external surface of said first side upon rupture;
      wherein said heating and/or cooling element changes said first temperature of said product; and
      wherein said product is applied to said target surface.

2. The applicator of claim 1, wherein said heating and/or cooling element is in contacting engagement with said reservoir.

3. The applicator of claim 1, wherein said product is selected from the group consisting of face cleansers, body cleansers, toners, lotions, moisturizers, ointments, cosmetics/make-ups, medicaments, and related topically applied treatments.

4. The applicator of claim 1, wherein said product comprises components selected from the group consisting of alcohols, colorants/pigments, emollients, emulsifiers, oils, polymers, and waxes.

5. The applicator of claim 1, wherein said product has shear-thinning or thixotropic properties.

6. The applicator of claim 1, wherein said product is selected from the group consisting of petrolatum, petroleum jelly, castor oil, sunscreen, octocrylene, tocopheryl acetate, gums, and non-volatile organo-substituted polysiloxanes.

7. The applicator of claim 1, wherein said applicator contains a massaging structure disposed upon the first external surface.

8. The applicator of claim 7, wherein said massaging structure is selected from the group consisting of a rigid pleated structure, corrugated structure, ribbed structure, rigid raised surface protrusions, recessed surface protrusions, void spaces within an otherwise solid flat structure, perforations within an otherwise solid flat structure, rotating or rolling balls, rotating or rolling cylinders, rotating or rolling rods, three-dimensional patterns embossed in a solid material, three dimensional patterns engraved in a solid material, and three-dimensional patterns formed in a solid material.

9. The applicator of claim 1, wherein said rupturable reservoir is provided with a frangible seal having a resistance to bursting.

10. The applicator of claim 1, further comprising a barrier layer disposed proximate to said first side, said barrier layer being substantially impervious to said product.

11. The applicator of claim 1, wherein said heating/cooling element includes an exothermic or endothermic system that provides a heating or cooling effect.

12. The applicator of claim 11, wherein said exothermic or endothermic system includes an anhydrous reactions, heats of solution, oxidation reactions, crystallization, corroding alloys, zeolite-liquid systems and/or heat of neutralization.

13. The applicator of claim 2, wherein said heating/cooling element comprises an anhydrous salt.

14. The applicator of claim 1, wherein said first side comprises a synthetic woven, synthetic knit, nonwoven, apertured film, macroscopically expanded three-dimensional formed film, absorbent or fibrous absorbent material, foam, or laminates and/or combinations thereof.

15. The applicator of claim 14, wherein said first side comprises a nonwoven.

16. The applicator of claim 1 wherein said rupturable reservoir is ruptured by an application of force.

17. The applicator of claim 1 wherein said rupturable reservoir comprises a chamber.

18. The applicator of claim 1 wherein said rupturable reservoir comprises a dispensing aperture.

19. The applicator of claim 1 wherein said rupturable reservoir comprises a plurality of chambers.

* * * * *

UNITED STATES PATENT AND TRADEMARK OFFICE
CERTIFICATE OF CORRECTION

PATENT NO. : 7,021,848 B1 Page 1 of 1
APPLICATION NO. : 10/089351
DATED : April 4, 2006
INVENTOR(S) : Gruenbacher It is certified that error appears in the above-identified patent and that said Letters Patent is hereby corrected as shown below:

Column 15, Line 7    Delete "oh", Insert --or--

Column 15, Line 42    Delete "it", Insert --if--

Column 15, Line 51    Delete "pane", Insert --panel--

Column 28, Line 13    Delete "so id", Insert --solid--

Signed and Sealed this

First Day of August, 2006

JON W. DUDAS
*Director of the United States Patent and Trademark Office*